US012053316B2

(12) United States Patent
Antoniades et al.

(10) Patent No.: US 12,053,316 B2
(45) Date of Patent: Aug. 6, 2024

(54) RADIOMIC SIGNATURE OF ADIPOSE

(71) Applicant: Oxford University Innovation Limited, Oxford (GB)

(72) Inventors: Charalambos Antoniades, Oxford (GB); Alexios Antonopoulos, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 696 days.

(21) Appl. No.: 17/276,846

(22) PCT Filed: Sep. 18, 2019

(86) PCT No.: PCT/GB2019/052632
§ 371 (c)(1),
(2) Date: Mar. 17, 2021

(87) PCT Pub. No.: WO2020/058712
PCT Pub. Date: Mar. 26, 2020

(65) Prior Publication Data
US 2022/0110598 A1    Apr. 14, 2022

(30) Foreign Application Priority Data

Sep. 18, 2018 (GR) .............................. 20180100430
Oct. 29, 2018 (GR) .............................. 20180100490
(Continued)

(51) Int. Cl.
*G06T 7/11*       (2017.01)
*A61B 6/00*       (2024.01)
(Continued)

(52) U.S. Cl.
CPC ............ *A61B 6/5217* (2013.01); *A61B 6/032* (2013.01); *A61B 6/037* (2013.01); *A61B 6/5235* (2013.01);
(Continued)

(58) Field of Classification Search
CPC ....... A61B 6/032; A61B 6/037; A61B 6/5217; A61B 6/5235; G06T 2207/10081;
(Continued)

(56) References Cited

U.S. PATENT DOCUMENTS 9,811,904 B2    11/2017    Lambin et al.
2011/0257505 A1    10/2011    Suri
(Continued)

FOREIGN PATENT DOCUMENTS

CN    106999122 A    8/2017
EP    2 793 164 A1    10/2014
(Continued)

OTHER PUBLICATIONS

Chun-Qiang Lu,"Diabetes risk assessment with imaging: a radiomics study of abdominal CT," Dec. 6, 2018, European Radiology (2019) 29,pp. 2233-2239.*
(Continued)

*Primary Examiner* — Omar S Ismail
(74) *Attorney, Agent, or Firm* — Thomas|Horstemeyer, LLP

(57) ABSTRACT

A method for characterising a region of interest comprising adipose tissue using medical imaging data, e.g. based on computer tomography (CT) of a subject is disclosed. The method comprises calculating the value of a radiomic signature of the region of interest using the medical imaging data. Also disclosed is a method for deriving a radiomic signature indicative of adipose tissue dysfunction. The method comprises obtaining a radiomic dataset and using (Continued)

the radiomic dataset to construct a radiomic signature of a region of interest comprising adipose tissue. Also disclosed are systems for performing the aforementioned methods.

25 Claims, 9 Drawing Sheets

(30) Foreign Application Priority Data

| Nov. 5, 2018 | (GB) | 1818049 |
|---|---|---|
| Nov. 7, 2018 | (GR) | 20180100510 |
| Dec. 10, 2018 | (GB) | 1820044 |
| Dec. 20, 2018 | (GB) | 1820855 |

(51) Int. Cl.

| A61B 6/03 | (2006.01) |
|---|---|
| G06T 7/00 | (2017.01) |
| G06T 7/40 | (2017.01) |
| G16H 10/60 | (2018.01) |
| G16H 30/20 | (2018.01) |
| G16H 30/40 | (2018.01) |
| G16H 50/20 | (2018.01) |
| G16H 50/30 | (2018.01) |
| G16H 50/70 | (2018.01) |

(52) U.S. Cl.
CPC .............. *G06T 7/0012* (2013.01); *G06T 7/11* (2017.01); *G06T 7/40* (2013.01); *G16H 30/20* (2018.01); *G16H 30/40* (2018.01); *G16H 50/20* (2018.01); *G16H 50/30* (2018.01); *G16H 50/70* (2018.01); *G06T 2207/10081* (2013.01); *G06T 2207/20084* (2013.01); *G16H 10/60* (2018.01)

(58) Field of Classification Search
CPC . G06T 2207/20064; G06T 2207/20081; G06T 2207/20084; G06T 7/0012; G06T 7/11; G06T 7/40; G06T 7/42; G06T 7/45; G16H 10/60; G16H 30/20; G16H 30/40; G16H 50/20; G16H 50/30; G16H 50/70
See application file for complete search history.

(56) References Cited

U.S. PATENT DOCUMENTS

| 2013/0004040 | A1 | 1/2013 | Chen et al. |
| 2014/0114618 | A1 | 4/2014 | Fonte et al. |
| 2017/0337681 | A1 | 11/2017 | Lure et al. |
| 2017/0352157 | A1 | 12/2017 | Madabhushi et al. |
| 2018/0144472 | A1* | 5/2018 | Kullberg ............ G01R 33/4828 |
| 2018/0342058 | A1 | 11/2018 | Madabhushi et al. |
| 2019/0114767 | A1* | 4/2019 | Muehlberg ............ G06T 11/008 |
| 2021/0077009 | A1* | 3/2021 | Viswanath ............ A61B 5/4255 |
| 2021/0113146 | A1* | 4/2021 | Pogue .................... H04N 19/96 |
| 2021/0166389 | A1* | 6/2021 | Denzinger ............ A61B 6/504 |

FOREIGN PATENT DOCUMENTS

| EP | 2 958 049 | A2 | 12/2015 |
| EP | 3 409 187 | A1 | 12/2018 |
| GB | 2557263 | A * | 6/2018 | ............... A61B 6/03 |
| GB | 2557263 | A | 6/2018 |
| WO | 2011/163624 | A1 | 12/2011 |
| WO | 2015/054597 | A2 | 4/2015 |
| WO | 2015/061882 | A1 | 5/2015 |
| WO | 2016/024128 | A1 | 2/2016 |
| WO | 2018/078395 | A1 | 5/2018 |
| WO | 2019/051358 | A1 | 3/2019 |

OTHER PUBLICATIONS

Lina Yu,"iVAR: Interactive Visual Analytics of Radiomics Features from Large-Scale Medical Images," 2017 IEEE International Conference on Big Data,pp. 3916-3922.*
Klara J. Rosenquist,"Visceral and Subcutaneous Fat Quality and Cardiometabolic Risk," Nov. 9, 2012, JACC: Cardiovascular Imaging vol. 6,No. 7,2013,pp. 762-769.*
Joseph M. Company,"Epicardial fat gene expression after aerobic exercise training in pigs with coronary atherosclerosis: relationship to visceral and subcutaneous fat," Oct. 7, 2010,J Appl Physiol 109: 1904-1912, 2010,doi:10.1152/japplphysiol.00621.2010, pp. 1904-1910.*
Elisa Scalco,"Texture analysis of medical images for radiotherapy applications," Nov. 16, 2016,British Institute of Radiology,https://doi.org/10.1259/bjr.20160642,pp. 1-10.*
Fuquan Liu,"Development and validation of a radiomics signature for clinically significant portal hypertension in cirrhosis (CHESS1701): a prospective multicenter study," Sep. 27, 2018,EBioMedicine 36 (2018) ,www.ebiomedicine.com,pp. 151-157.*
Jiliang Rena,"Magnetic resonance imaging based radiomics signature for the preoperative discrimination of stage I-II and III-IV head and neck squamous cell," Jul. 2, 2018,European Journal of Radiology 106 (2018),pp. 1-5.*
Jingjun Wu,"Radiomics-based classification of hepatocellular carcinoma and hepatic haemangioma on precontrast magnetic resonance images," Mar. 11, 2019, BMC Medical Imaging (2019) 19:23,pp. 1-10.*
Examination Report for GB No. 1820855.3, dated Dec. 19, 2022, pp. 1-4.
Gastroenterology, vol. 154, No. 6, Suppl. 1, Kurowski J A et al., "Radiomic Texture Analysis Shows Differential Expression Within Visceral Adipose Tissue Regions on MRI Reflecting Severity of Pediatric Crohn's Disease", S448.
Examination Report for GB No. 1820855.3, dated Apr. 21, 2022, pp. 1-8.
International Preliminary Report on Patentability for WO 2020/058712 (PCT/GB2019/052632), dated Mar. 23, 2021, pp. 1-7.
International Search Report and Written Opinion for WO 2020/058712 (PCT/GB2019/052632), dated Dec. 5, 2019, pp. 1-30.
UK Search Report for GB 1820855.3, dated Jun. 21, 2019, pp. 1-5.
UK Search Report for GB 1818049.7, dated May 3, 3019, pp. 1-5.
UK Search Report for GB 1820044.4, dated Jun. 17, 2019, pp. 1-5.
Yu Lina et al: "iVAR: Interactive visual analytics of radiomics features from large-scale medical images", 2017 IEEE International Conference on Big Data (Big Data), IEEE, Dec. 11, 2017 (Dec. 11, 2017), pp. 3916-3923.
Rosenquist Klara J et al: "Visceral and Subcutaneous Fat Quality and Cardiometabolic Risk", JACC: Cardiovascular Imaging, Elsevier, Amsterdam, NL, vol. 6, No. 7, May 8, 2013 (May 8, 2013), pp. 762-771.
Chinese Office Action for Application No. 2019800746446, dated Oct. 20, 2023, pp. 1-25 (Translation Included).

* cited by examiner

Figure 2a  Principal components of ScAT radiomic features

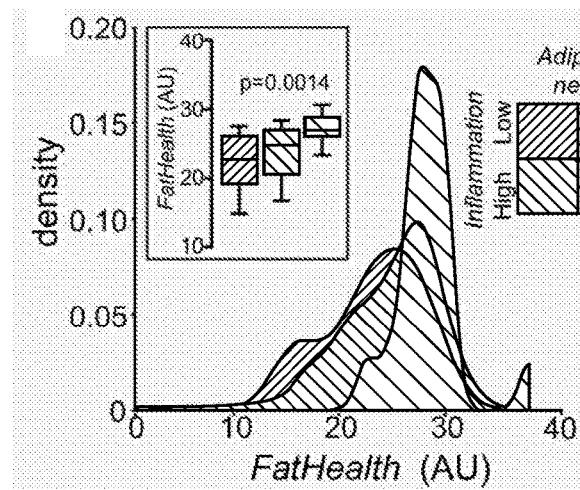
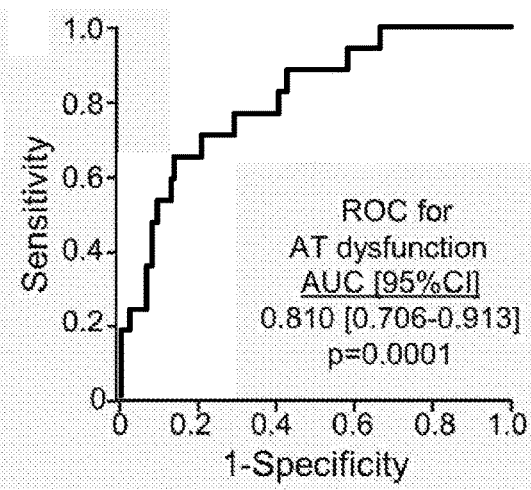
Figure 5a  Figure 5b
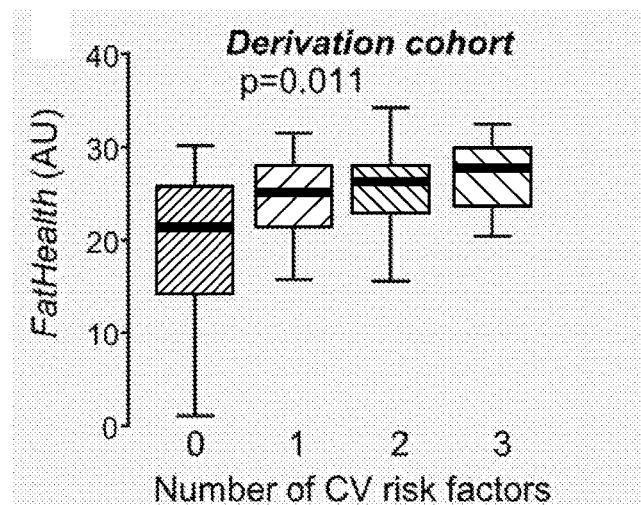
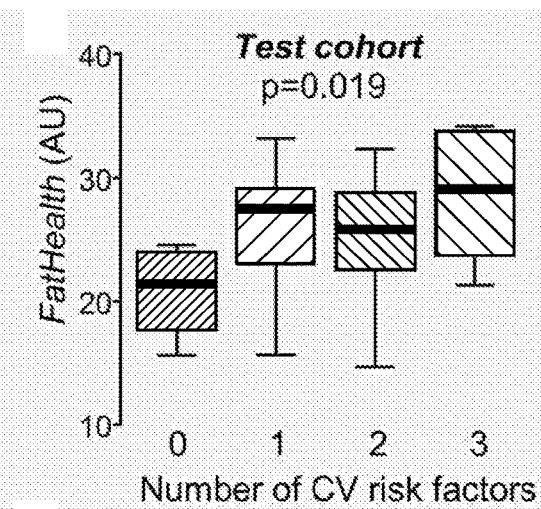
Figure 5c  Figure 5d
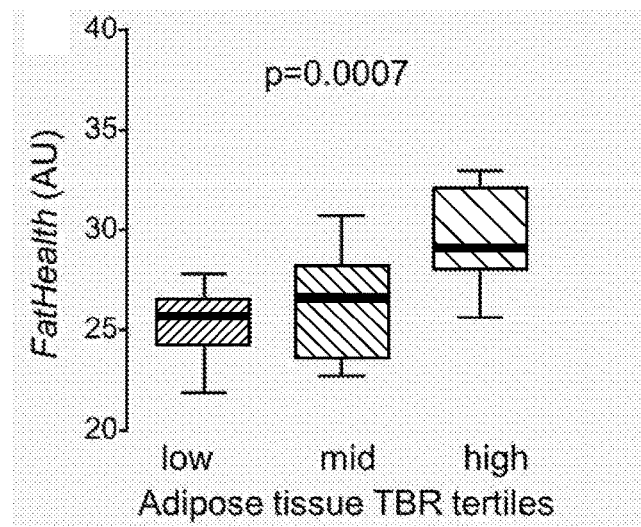
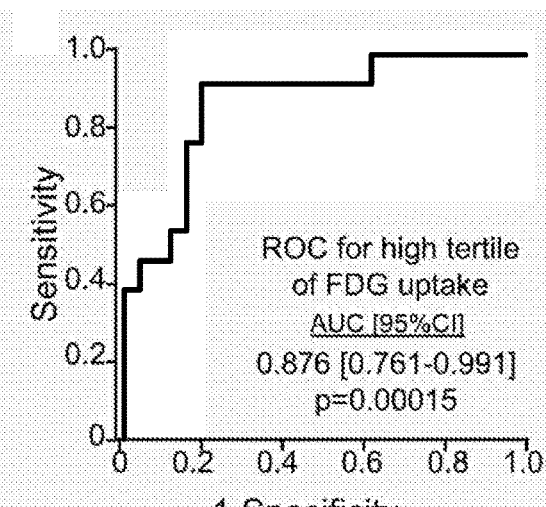
Figure 5e  Figure 5f

RADIOMIC SIGNATURE OF ADIPOSE

CROSS-REFERENCE TO RELATED APPLICATIONS

This application is the National Stage of International Application No. PCT/GB2019/052632, filed Sep. 18, 2019, which claims priority to GR 20180100430, filed Sep. 18, 2018, GR 20180100490, filed Oct. 29, 2018, GB 1818049.7, filed Nov. 5, 2018, GR 20180100510, filed Nov. 7, 2018, GB 1820044.4, filed Dec. 10, 2018, and GB 1820855.3, filed Dec. 20, 2018, which are entirely incorporated herein by reference.

FIELD OF THE INVENTION

The invention relates to methods of characterising adipose tissue, in particular using a radiomic signature, and systems for the same. The invention also relates to methods of deriving such signatures, and systems for the same.

BACKGROUND

Even though adipose tissue dysfunction is central in the pathogenesis of diabetes, obesity and related vascular disease risk, there is currently a lack of means to study its biology other than by performing invasive biopsies.

Techniques are known for imaging adipose tissue (see, for example, Wang, H., Chen, Y. E. & Eitzman, D. T. Imaging body fat: techniques and cardiometabolic implications. Arteriosclerosis, thrombosis, and vascular biology 34, 2217-2223, doi:10.1161/ATVBAHA.114.303036 (2014); Christen, T. et al. Increased glucose uptake in visceral versus subcutaneous adipose tissue revealed by PET imaging. JACC. Cardiovascular imaging 3, 843-851, doi:10.1016/j.jcmg.2010.06.004 (2010); Ran, C. et al. PET Imaging of Human Brown Adipose Tissue with the TSPO Tracer [(11) C]PBR28. Molecular imaging and biology: MIB: the official publication of the Academy of Molecular Imaging, doi: 10.1007/s11307-017-1129-z (2017)). In particular, computerised tomography is now used for the imaging of human adipose tissue, for example to quantify fat volumes.

However, although a volumetric approach can be used to reliably describe and quantify body adiposity, it is only indirectly and poorly linked to features of adipose tissue biology. Adipose tissue dysfunction plays a central role in the development of insulin resistance and obesity-related vascular disease. However, fat expansion in of itself does not always lead to insulin resistance development, which depends on aspects of adipose tissue biology, such as adipocyte hyperplasia or hypertrophy, adipogenesis capacity, adipose tissue inflammation and fibrosis. As a consequence, adipose tissue biological phenotypes cannot be accurately captured by simple volumetric quantification of body adiposity.

The average radiodensity of visceral or subcutaneous fat has been recently proposed as a simple metric of adipose tissue quality, which is independently associated with cardiovascular risk in clinical cohorts (see Rosenquist, K. J. et al. Visceral and subcutaneous fat quality and cardiometabolic risk. JACC. Cardiovascular imaging 6, 762-771, doi: 10.1016/j.jcmg.2012.11.021 (2013)). Other methods such as PET/CT imaging can be used to study adipose tissue metabolic activity (for example by quantifying 18F-FDG uptake), but PET is limited by its availability, cost and high radiation exposure.

As yet, there is no way of adequately phenotyping adipose tissue biology by non-invasive means. Therefore, there is an unmet need for non-invasive methods for the detection of adipose tissue dysfunction and assessment of the obesity-related metabolic burden.

SUMMARY OF THE INVENTION

According to a first aspect of the invention, there is provided a method for characterising a region of interest (for example its phenotype, e.g. composition and/or texture) comprising adipose tissue. The method may be used for identifying or diagnosing adipose tissue dysfunction, or for identifying phenotypic characteristics of adipose tissue dysfunction. The method may comprise calculating the value of a radiomic signature of the region of interest using medical imaging data. The radiomic signature may be calculated on the basis of measured values of a plurality of radiomic features of the region of interest. The measured values of the radiomic features may be calculated from the medical imaging data.

The radiomic signature may provide a measure of the texture of the region of interest or of the adipose tissue. At least one of the radiomic features may provide a measure of the texture of the region of interest or adipose tissue. For example, at least one of the radiomic features may be a texture statistic.

The radiomic signature (i.e. its value) may be indicative of, or associated with (e.g. statistically significantly associated with), adipose tissue dysfunction, in particular of the adipose tissue of the region of interest. Alternatively, the radiomic signature may be indicative of, or associated with a surrogate marker of adipose tissue dysfunction, for example metabolic disorder associated with adipose tissue dysfunction, a phenotypic characteristic of adipose tissue dysfunction, or a gene expression profile associated with adipose tissue dysfunction.

The radiomic signature (i.e. its value) may be predictive of the likelihood of the subject developing a metabolic disorder, in particular a metabolic disorder associated with adipose tissue dysfunction, such as diabetes or insulin resistance.

The plurality of radiomic features may comprise at least two radiomic features selected from the radiomic features of clusters 1 to 5, wherein the at least two radiomic features are each selected from different groups, and wherein:

group 1 consists of Large Dependence Low Gray Level Emphasis, Sum Average, Joint Average, High Gray Level Emphasis, Short Run High Gray Level Emphasis, Autocorrelation, and High Gray Level Run Emphasis;

group 2 consists of Total Energy HHL, Energy HHL, Size Zone Non Uniformity HHH, Size Zone Non Uniformity HLH, Size Zone Non Uniformity LHH, Gray Level Non Uniformity Normalized HHL (GLDM), Inverse Variance HHL, Gray Level Non Uniformity Normalized HHL (GLSZM), Size Zone Non Uniformity LHL, Run Length Non Uniformity HHH, Size Zone Non Uniformity HLL, Dependence Non Uniformity HHL, Gray Level Non Uniformity Normalized HHH (GLDM), Inverse Difference Moment HHH, Inverse Difference HHH, Uniformity HHH, Informational Measure of Correlation 2, Inverse Variance HHH, Total Energy LHL, Size Zone Non Uniformity, Sphericity, Size Zone Non Uniformity LLH, Run Length Non Uniformity Normalized HHL, Gray Level Non Uniformity Normalized HHH (GLSZM), Dependence Non Uniformity Normalized HHL, Zone Percentage HHL, Small Dependence Emphasis HHL, Size Zone Non Uniformity Normalized HHL, Small Area Emphasis HHL, Correlation, Dependence Non Uniformity LHH, Total Energy LHH, Short Run Emphasis HHH, Run Length Non Uniformity Normalized HHH, Dependence Non Uniformity LHL, Inverse Difference LHH, Inverse Difference Moment LHH, Small Dependence Emphasis HHH, Dependence Variance HLH, Run Percentage HHH, Zone Percentage HHH, Inverse Difference LHL, Dependence Non Uniformity HLH, Inverse Variance LHH, Large Dependence Emphasis HLH, Run Length Non Uniformity Normalized HLH, Short Run Emphasis HLH, Dependence Non Uniformity Normalized HLH, Difference Variance, Long Run Emphasis HLH, Energy LHL, Contrast (GLCM), Run Percentage HLH, Joint Entropy LHH, Difference Entropy, Small Dependence Emphasis HLH, Size Zone Non Uniformity Normalized HLH, Small Area Emphasis HLH, Difference Entropy LHH, Difference Average, Run Variance HLH, Inverse Difference Moment, Inverse Difference, Inverse Variance, Run Entropy LHH, Entropy LHH, Zone Percentage HLH, Sum Entropy LHH, Inverse Difference Moment Normalized, Inverse Difference Normalized, Small Dependence Low Gray Level Emphasis, Energy LHH, Joint Entropy LHL, Small Area Low Gray Level Emphasis, Strength, Dependence Non Uniformity LLH, Run Length Non Uniformity HHL, Gray Level Non Uniformity Normalized LHL (GLDM), Busyness, Dependence Non Uniformity Normalized LHH, Small Dependence Emphasis LHH, Coarseness, Zone Percentage LHH, Dependence Non Uniformity Normalized LHL, Run Length Non Uniformity HLH, Small Dependence Emphasis LHL, Joint Entropy, Small Area Emphasis LHL, Size Zone Non Uniformity Normalized LHL, Short Run Emphasis HLL, Run Length Non Uniformity LHH, Run Length Non Uniformity Normalized HLL, Large Dependence Emphasis HLL, Long Run Emphasis HLL, Run Percentage HLL, Dependence Variance HLL, Dependence Non Uniformity HLL, Zone Percentage HLL, Dependence Non Uniformity, Dependence Non Uniformity HHH, Dependence Non Uniformity Normalized LLH, Low Gray Level Zone Emphasis, and Short Run Low Gray Level Emphasis;

group 3 consists of Dependence Entropy, Zone Entropy, Correlation, Informational Measure of Correlation 2, Zone Percentage HHH, Small Dependence Emphasis HHH, Run Percentage HHH, Dependence Non Uniformity Normalized LHL, Small Dependence Emphasis LHL, Zone Percentage HHL, Small Dependence High Gray Level Emphasis, Small Dependence Emphasis HHL, Dependence Non Uniformity Normalized HHL, Short Run Emphasis HHH, Run Length Non Uniformity Normalized HHH, Run Length Non Uniformity Normalized HHL, Size Zone Non Uniformity Normalized LHL, Small Area Emphasis LHL, Size Zone Non Uniformity Normalized HHL, Small Area Emphasis HHL, Zone Percentage HLH, Run Variance HLH, Small Dependence Emphasis HLH, Long Run Emphasis HLH, Size Zone Non Uniformity Normalized LLH, Small Area Emphasis LLH, Size Zone Non Uniformity Normalized HLH, Small Area Emphasis HLH, Run Percentage HLH, Run Length Non Uniformity Normalized HLH, Short Run Emphasis HLH, Large Dependence Emphasis HLH, Zone Percentage LHH, Small Dependence Emphasis LLH, Small Dependence Emphasis LHH, Dependence Non Uniformity Normalized HLH, Zone Percentage LLH, Dependence Variance HLH, Dependence Non Uniformity Normalized LLH, Dependence Non Uniformity Normalized LHH, Inverse Difference LHL, Inverse Difference Moment HHH, Inverse Difference HHH, Uniformity HHH, Gray Level Non Uniformity Normalized LHL (GLSZM), Gray Level Non Uniformity Normalized HHH (GLDM), Gray Level Non Uniformity Normalized HHL (GLDM), Joint Entropy LHL, Inverse Difference Normalized, Inverse Difference Moment Normalized, Long Run Emphasis HLL, Zone Percentage HLL, Inverse Difference, Inverse Difference Moment, Difference Average, Run Percentage HLL, Large Dependence Emphasis HLL, Contrast (GLCM), Short Run Emphasis HLL, Run Length Non Uniformity Normalized HLL, Inverse Variance, Inverse Variance HHL, Difference Entropy, Dependence Variance HLL, Inverse Difference Moment LHH, Difference Variance, Entropy LHH, Inverse Variance LHH, Inverse Difference LHH, Inverse Variance HHH, Sum Entropy LHH, Joint Entropy LHH, Gray Level Non Uniformity Normalized HHH (GLSZM), Gray Level Non Uniformity Normalized HHL (GLSZM), Difference Entropy LHH, and Run Entropy LHH;

group 4 consists of Mean LLL, Median LLL, and Energy LLL; and group 5 consists of Run Entropy.

The at least two radiomic features may comprise at least two of Large Dependence Low Gray Level Emphasis, Total Energy HHL, Dependence Entropy, Mean LLL, and Run Entropy. The at least two radiomic features may consist of five radiomic features, the five radiomic features may consist of Large Dependence Low Gray Level Emphasis, Total Energy HHL, Dependence Entropy, Mean LLL, and Run Entropy.

The at least two radiomic features may be selected from the radiomic features of clusters A to C, wherein the at least two radiomic features are each selected from different clusters, and wherein:

cluster A consists of the radiomic features of groups 1 to 3;

cluster B consists of the radiomic features of group 4; and cluster C consists of the radiomic features of group 5.

The plurality of radiomic features may comprise at least two radiomic features selected from the radiomic features of clusters A to C, wherein the at least two radiomic features are each selected from different clusters, and wherein:

cluster A consists of Large Dependence Low Gray Level Emphasis, Run Entropy, Dependence Entropy, Cluster Shade, Skewness, Run Variance HLH, Voxel Number, and Gray Level Non Uniformity;

cluster B consists of Mean LLL, Median LLL, Joint Average, Median, Complexity, Long Run High Gray Level Emphasis, Sphericity, Kurtosis, and Coarseness HHH; and cluster C consists of Major Axis, Small Dependence High Gray Level Emphasis, Minor Axis, Energy LLL, Maximum 2D Diameter Row, Long Run Low Gray Level Emphasis, Total Energy HHL, Dependence Non Uniformity Normalized HHH, Contrast (GLCM), Surface Volume Ratio, Sum Entropy, Size Zone Non Uniformity Normalized HHH, Cluster Prominence LHH, Contrast LLH (GLCM), and Energy LHL.

The plurality of radiomic features may comprise at least two radiomic features selected from Large Dependence Low Gray Level Emphasis, Run Entropy, Dependence Entropy, Cluster Shade, Skewness, Run Variance HLH, Voxel Number, Gray Level Non Uniformity, Mean LLL, Median LLL, Joint Average, Median, Complexity, Long Run High Gray Level Emphasis, Sphericity, Kurtosis, Coarseness HHH, Major Axis, Small Dependence High Gray Level Emphasis, Minor Axis, Energy LLL, Maximum 2D Diameter Row, Long Run Low Gray Level Emphasis, Total Energy HHL, Dependence Non Uniformity Normalized HHH, Contrast (GLCM), Surface Volume Ratio, Sum Entropy, Size Zone Non Uniformity Normalized HHH, Cluster Prominence LHH, Contrast LLH (GLCM), and Energy LHL.

The at least two radiomic features may comprise at least three radiomic features. The at least two radiomic features may comprise at least four radiomic features. The at least two radiomic features may comprise at least five radiomic features.

The medical imaging data may comprise attenuation values for each of a plurality of voxels corresponding to at least the region of interest.

At least one of the plurality of radiomic features may be calculated from a wavelet transformation of the attenuation values.

The method may further comprise identifying the region of interest from or using the medical imaging data. The region of interest may be identified using manual contouring. The region of interest may be identified as including only voxels of the medical imaging data having an attenuation value falling within a given range of attenuation values. The given range may be from about −190 to about −30 Hounsfield Units.

The method may further comprise segmenting the region of interest. The method may further comprise calculating the values of the radiomic features from the segmented region of interest.

The method may further comprise predicting the risk of the subject developing a metabolic disorder based at least on at least the calculated value of the radiomic signature. The metabolic disorder may be diabetes or insulin resistance.

The method may further comprise determining or diagnosing whether the subject has adipose tissue dysfunction, or a phenotypic characteristic of adipose tissue dysfunction (e.g. fibrosis or inflammation) based on at least the calculated value of the radiomic signature.

The radiomic signature may comprise a weighted sum of the plurality of radiomic features. The radiomic signature may be linearly related to the weighted sum of the radiomic features.

According to a second aspect of the invention, there is provided a method for deriving a radiomic signature. The radiomic signature may be indicative of adipose tissue dysfunction. The radiomic signature may be suitable for identifying or diagnosing adipose tissue dysfunction. The method may comprise using a radiomic dataset to construct a radiomic signature indicative of adipose tissue dysfunction. The radiomic signature may be calculated on the basis of a second plurality of radiomic features. The dataset may comprise the values of a first plurality of radiomic features obtained from medical imaging data of a region of interest comprising adipose tissue for each of a plurality of individuals. The plurality of individuals may comprise a first group of individuals identified as having (in particular at the time when the medical imaging data were collected or recorded) adipose tissue dysfunction and a second group of individuals identified as not having (in particular at the time when the medical imaging data were collected or recorded) adipose tissue dysfunction. The second plurality of radiomic features may be selected from amongst the first plurality of radiomic features, in particular to provide a radiomic signature indicative of adipose tissue dysfunction as determined from or using the dataset, for example using a machine learning algorithm.

Each of the individuals may be identified as having or not having adipose tissue dysfunction based at least in part on a marker of adipose tissue dysfunction. The radiomic dataset may further comprise the marker of adipose tissue dysfunction.

The marker may be or may comprise, or may be indicative of, the presence or absence of a metabolic disorder associated with adipose tissue dysfunction, for example diabetes or insulin resistance, for each of the plurality of individuals (i.e. information distinguishing whether each of the individuals has or does not have the metabolic disorder).

The marker may comprise a phenotypic characteristic of adipose tissue associated with adipose tissue dysfunction, for example fibrosis or inflammation.

The marker may comprises a surrogate marker of a phenotypic characteristic of adipose tissue associated with adipose tissue dysfunction, such as selected gene expression profiles. In particular, the surrogate marker may be or may comprise gene expression profiles that are markers of phenotypic characteristics of adipose tissue dysfunction.

The method may further comprise identifying a first subset of the first plurality of radiomic features that are not collinear with each other, as determined from the dataset. The second plurality of radiomic features may comprise at least two radiomic features that are each selected to be, or to be collinear or highly correlated with (as determined from the dataset), different radiomic features belonging to the first subset.

The method may further comprise using a feature selection algorithm (e.g. a machine learning feature selection algorithm) to identify a second subset of radiomic features from amongst the first subset that the radiomic signature should be calculated on the basis of (i.e. optimal features). In other words, the second subset of radiomic features are predicted to maximise the accuracy (e.g. optimise or maximise the association of the radiomic signature with adipose tissue dysfunction) of the radiomic signature, e.g. when the radiomic signature is calculated on the basis of the second subset of radiomic features (and is optimised). The second subset of radiomic features may maximise the association of a preliminary radiomic signature with adipose tissue dysfunction (when the preliminary radiomic signature is calculated on the basis of the second subset of the radiomic features), as determined from the dataset. The at least two radiomic features may be selected to be, or to be collinear with (as determined from the dataset), different radiomic features belonging to the second subset. The at least two radiomic features may comprise all of the radiomic features belonging to the second subset, or collinear equivalents thereof that are collinear with the radiomic features, as determined from the dataset. In other words, the at least two radiomic features may comprise each of, or radiomic features that are collinear with each of, the radiomic features belonging to the second subset.

Each of the at least two (or second plurality of) radiomic features may be selected to be stable, as determined from the dataset. All unstable radiomic features may be removed from the first plurality of radiomic features prior to selecting the second plurality of radiomic features.

A radiomic feature may be identified as being unstable if an intraclass correlation coefficient (for example scan-rescan and/or multiple delineation) for the radiomic feature is less than a stability threshold, for example as determined from the dataset. The stability threshold may be at least about 0.9.

The method may further comprise identifying a plurality of clusters of the first plurality of radiomic features, for example of the first subset of radiomic features, by performing a cluster analysis (e.g. using a clustering algorithm, in particular a machine learning clustering algorithm), for example a correlation cluster analysis. The second plurality of, or at least two, radiomic features may each be selected from, or be selected to be collinear with radiomic features from, different clusters. The cluster analysis may identify the clusters based on the strength of the correlations between the radiomic features. The intra-cluster correlations may be stronger than the inter-cluster correlations. For example, the radiomic features within each cluster may be correlated with each other to a greater degree than they are correlated with radiomic features in other clusters.

The cluster analysis may be a hierarchical cluster analysis, a k-means cluster analysis, a distribution-based cluster analysis, or a density-based cluster analysis. In particular, the cluster analysis may be a hierarchical cluster analysis. The cluster analysis, for example the cluster algorithm, may identify the clusters based on a distance between the radiomic features, for example the squared Euclidean distance between the radiomic features, for example in a correlation plot. The cluster algorithm may identify the clusters based on the distance between the features in correlation space, where the distance between each pair of features corresponds to the degree to which those features are correlated, i.e. the closer the two features are in correlation space the more correlated they are with one another.

The method may comprise identifying a plurality of clusters of radiomic features. Each cluster may comprise a subset of the plurality of radiomic features. Each cluster may include an original radiomic feature with which each of the other radiomic features in that cluster is selected to be collinear, for example as determined or calculated from the dataset. The at least two radiomic features may each be selected from different clusters.

Each of the original radiomic features may be selected to be not collinear with any of the original radiomic features of any of the other clusters, for example as determined or calculated from the dataset.

Each of the radiomic features in each cluster may be selected to be collinear with all of the other radiomic features in the same cluster, for example as determined or calculated from the dataset.

Each of the original radiomic features may be selected to be significantly associated with the clinical endpoint, for example as determined or calculated from the dataset.

Each of the original radiomic features may be selected to be the most strongly associated with the clinical endpoint of all the radiomic features in its cluster, for example as determined or calculated from the dataset.

The at least two radiomic features may be selected to be not collinear with each other, for example as determined or calculated from the dataset.

The method may comprise identifying a plurality of groups of radiomic features. Each group may comprise a subset of the first plurality of radiomic features. Each group may include an original radiomic feature (e.g. one of the first subset) with which each of the other radiomic features in that group is selected to be collinear, for example as determined or calculated from the dataset. The second plurality of radiomic features, for example the at least two radiomic features, may each be selected from different groups.

Each of the original radiomic features may be selected to be not collinear with any of the original radiomic features of any of the other groups, for example as determined or calculated from the dataset.

Each of the radiomic features in each group may be selected to be collinear with all of the other radiomic features in the same group, for example as determined or calculated from the dataset.

The second plurality or the at least two radiomic features may be selected to be not collinear with each other, for example as determined or calculated from the dataset.

Two radiomic features may be identified as collinear with each other if they are correlated to an extent at least equal to a correlation threshold, as determined from the dataset. The correlation threshold may be calculated using Spearman's rho coefficient. The correlation threshold may be at least about $|rho|=0.75$, for example at least about $|rho|=0.9$. Two radiomic features may be identified as being highly correlated with each other if they are correlated to degree of at least about $|rho|=0.75$.

The radiomic signature may be constructed to be associated with adipose tissue dysfunction, as determined from the dataset. For example, the radiomic signature may be constructed to be significantly associated with adipose tissue dysfunction. The radiomic signature may be identified as being significantly associated with adipose tissue dysfunction if it is associated with adipose tissue dysfunction above a significance threshold. The significance threshold is at least about $\alpha=0.05$. The association of the radiomic signature with AT dysfunction may be calculated based on or using a receiver operating characteristic (ROC) curve analysis, in particular using an area under the curve (AUC) measurement (i.e. the C-statistic).

The step of constructing the radiomic signature may comprise refining the contributions of each of the second plurality of radiomic features to the radiomic signature to increase the association of the radiomic signature with adipose tissue dysfunction, as determined from the dataset.

The dataset may be divided into a training cohort dataset and a validation cohort dataset, and the step of constructing the radiomic signature may comprise deriving the signature using data for at least the training cohort and validating the signature using data for the validation cohort.

The step of constructing the radiomic signature may be performed using a machine learning algorithm. The method may comprise using a machine learning algorithm to select the second plurality of radiomic features from amongst the first plurality of radiomic features, in particular from amongst the first subset, to provide a radiomic signature that is indicative of adipose tissue dysfunction, as determined from the dataset.

The step of constructing the radiomic signature may be performed using multi-fold cross-validation. The step of constructing the radiomic signature may be performed using recursive feature elimination, for example with a random forest algorithm. The step of constructing the radiomic signature may be performed using logistic regression.

For example, the step of constructing the radiomic signature may comprise identifying a subset of the radiomic features that are to be included in the signature, for example using a feature selection machine learning algorithm. The feature selection may be performed using recursive feature elimination, for example using a random forest algorithm. The step of constructing the radiomic signature may then comprise refining or optimising the radiomic signature based on the subset of radiomic features identified in the feature selection step (e.g. the second subset), for example using logistic regression, again optionally using a machine learning algorithm. For example, a second machine learning algorithm (e.g. a radiomic signature optimisation algorithm such as a logistic regression algorithm) may be used to refine or optimise the radiomic signature calculated using the subset of radiomic features, for example using multi-fold cross-validation. In other words, the second machine learning algorithm refines or optimises a radiomic signature calculated on the basis of the subset of radiomic features.

The radiomic signature may comprise a weighted sum of the second plurality of radiomic features. The radiomic signature may be linearly related to the weighted sum of the second plurality of radiomic features.

The step of constructing the radiomic signature may comprise adjusting the relative weightings of each of the second plurality of radiomic features to increase the association of the radiomic signature with adipose tissue dysfunction, as determined from the dataset.

The radiomic signature may be constructed to provide a measure of the texture of the region of interest.

At least one of the second plurality of radiomic features (e.g. one of the at least two radiomic features) may provide a measure of the texture of the region of interest. For example, at least one of the second plurality of radiomic features may be a texture statistic. For example, each of the second plurality of radiomic features may provide a measure of the texture of the region of interest (i.e. each of the radiomic features may be texture statistics).

The method may further comprise configuring a system for calculating the value of the radiomic signature for a patient, specifically for a region of interest of a patient comprising adipose tissue. For example, the method may further comprise configuring a system for characterising a region of interest of the patient or subject by calculating the value of the derived radiomic signature for the patient or subject. The system may be configured to calculate the value of the derived radiomic signature using or based on medical imaging data of at least a region of interest of the patient or subject. The system may be configured to calculate the value of the derived radiomic signature using or based at least on the values of the second plurality of radiomic features of the region of interest of the patient or subject.

The method may therefore be for deriving a radiomic signature and configuring a system for characterising a region of interest (comprising adipose tissue) of a patient using the derived radiomic signature.

The system may be configured to receive the medical imaging data or values of the second plurality of radiomic features as an input. The system may be configured to output (e.g. display) the calculated value of the radiomic signature or a value based on the calculated value of the radiomic signature. The system may be configured to output an indication of whether the patient has adipose tissue dysfunction. The system may be configured to output an indication of the risk of the patient developing a metabolic disorder. The system may be a computer system.

The method may comprise providing instructions for configuring a system for calculating the value of the derived radiomic signature for a patient or subject.

The method may further comprise calculating the value of the derived radiomic signature for a region of interest of a patient or subject. For example, the method may further comprise characterising a region of interest of a patient or subject by calculating the value of the derived radiomic signature. The value of the derived radiomic signature may be calculated based on or using medical imaging data of at least the region of interest of the patient or subject. The value of the derived radiomic signature may be calculated using or based at least on the values of the second plurality radiomic features of the region of interest of the patient or subject. The region of interest of the patient comprises adipose tissue.

The method may therefore be for deriving a radiomic signature and characterising a region of interest using the derived radiomic signature.

The medical imaging data may be radiographic data. The medical imaging data may be computed tomography data.

The adipose tissue may be subcutaneous adipose tissue. The adipose tissue may be visceral adipose tissue. The adipose tissue may be thoracic adipose tissue.

The adipose tissue may comprise or consist of non-cardiovascular adipose tissue (i.e. non-cardiac or non-vascular adipose tissue). For example, the adipose tissue may comprise or consist of non-epicardial, -pericardial, or -perivascular adipose tissue. For example, the adipose tissue may comprise a majority (i.e. more than about 50% by volume) of non-cardiovascular adipose tissue. For example, the adipose tissue may comprise substantially non-cardiovascular adipose tissue. For example, the adipose tissue may comprise less than about 10% (by volume) cardiovascular adipose tissue, in particular less than about 5% cardiovascular adipose tissue.

Alternatively, the region of interest may be remote from (i.e. not adjacent to or attached to) the cardiovascular system. For example, the region of interest may be remote from the cardiovascular organs, such as the heart, and blood vessels, in particular arteries and veins. The adipose tissue may be not cardiac or vascular adipose tissue. For example, the adipose tissue may be not epicardial, pericardial, or perivascular adipose tissue.

The radiomic signature of the invention may also be calculated on the basis of further radiomic features of the region of interest in addition to the at least two radiomic features referred to above. For example, the radiomic signature may comprise other radiomic features in addition to the at least two radiomic features. Thus, it may be said that the radiomic signature is calculated on the basis of a plurality of radiomic features, and the plurality of radiomic features may comprise the at least two radiomic features.

The methods of the invention may also comprise the step of calculating the radiomic features from the medical imaging data.

According to a third aspect of the invention, there is provided a system configured to perform any of the methods as described above. The system may be a computer system. The system may comprise a processor configured to perform the steps of the method. The system may comprise a memory loaded with executable instructions for performing the steps of the method.

According to a fourth aspect of the invention, there is provided use of a radiomic signature for any of the above-described purposes, for example to characterise a region of interest, to detect adipose tissue dysfunction, or to predict the risk of developing a metabolic disorder. The radiomic signature may be calculated on the basis of measured values of a plurality of radiomic features of the region of interest.

The medical imaging data may be radiographic data. The medical imaging data may be computed tomography data.

BRIEF DESCRIPTION OF THE FIGURES

The invention will now be described with reference to the appended figures, in which:

FIG. 2 illustrates aspects of a principal component analysis of adipose tissue radiomic features. FIG. 2(a) is a scree plot of the percentage of variation explained by the first 86 principal components, accounting for 99.5% of variation in Arm 1 (843 radiomic features from 225 patients).

FIG. 3 illustrates aspects of unsupervised hierarchical clustering of patients and radiomic features.

FIG. 5 illustrates that a radiomic signature of a region of interest comprising adipose tissue, in this case a subcutaneous region, may be used as a radiomic biomarker of adipose tissue health and metabolic risk. FIG. 5(a) shows the association of a radiomic signature of the invention (referred to as "FatHealth") with adipose tissue differentiation/inflammation phenotype, based on the expression levels of FABP4 and TNFA. FIG. 5(b) plots logistic regression for classification of dysfunctional adipose tissue by the radiomic signature (FatHealth). Association between the number of cardiometabolic risk factors (i.e. smoking, hypertension, diabetes) and FatHealth in the derivation and test cohorts of the Arm 1 patients is illustrated using box and whisker plots in in FIGS. 5(c) and (d), respectively. FIG. 5(e) illustrates external validation of the radiomic signature (FatHealth) against 18-fluorodeoxyglucose uptake by subcutaneous adipose tissue in PET/CT imaging, and FIG. 5(f) illustrates the diagnostic accuracy of the radiomic signature for high adipose tissue inflammation (defined as tissue-to-background ratio in the highest tertile). AUC: area under the curve; TBR:target-to-background ratio.

DETAILED DESCRIPTION

Figure 1:
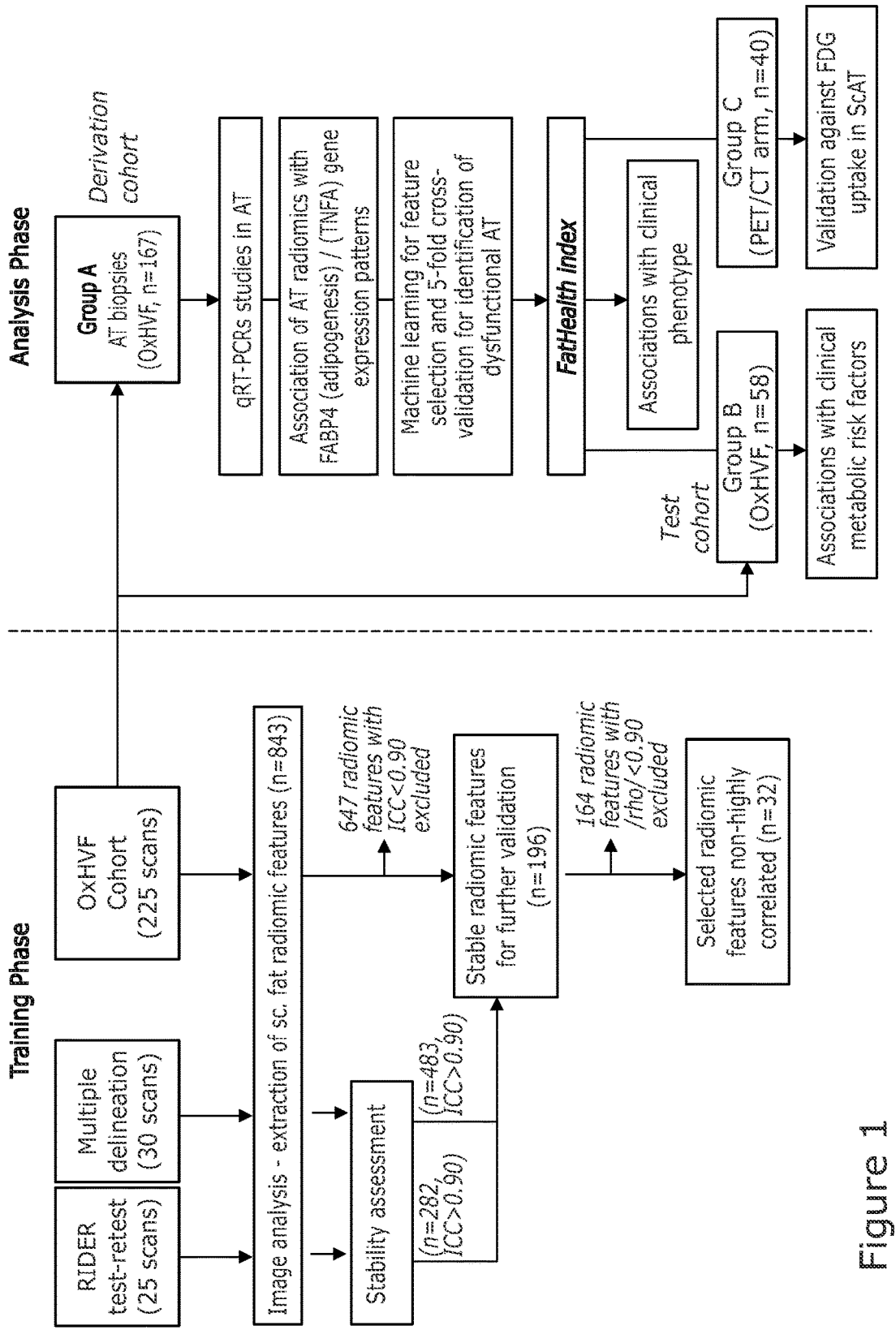
FIG. 1 summarises a method of deriving a radiomic signature. The analysis phase included a total of 225 patients undergoing coronary artery bypass grafting. Non-contrast enhanced Computed Tomography (CT) images were used to link adipose tissue radiomic features with tissue biology. Only stable radiomic features (i.e. those radiomic features that showed an intra-class correlation coefficient (ICC)≥0.90 in the training phase) were included in the analysis. Radiomic features associated with adipose tissue biology were internally validated using a machine learning algorithm with five-fold cross-validation. The top radiomic features were then externally validated in Arm 2 as biomarkers of adipose tissue inflammation against $^{18}$F-FDG positron emission tomography/computed tomography (PET/CT) imaging and in Arm 3 as biomarkers of vascular disease progression. AT: adipose tissue, ScAT: subcutaneous adipose tissue.

The inventors have discovered that a radiomic signature (otherwise known as a "score" or "index") calculated on the basis of two or more radiomic features of a region of interest (ROI) comprising adipose tissue is independently linked with distinct biological phenotypes of adipose tissue (AT) that are associated with AT dysfunction. In general, as used herein, "associated" may be taken to mean "statistically associated", for example "statistically significantly associated". In particular, the radiomic signature is able to differentiate the expression of gene markers of characteristics of AT dysfunction, such as adipocyte differentiation and adipose tissue inflammation. The radiomic signature of the invention is therefore preferably calculated on the basis of two or more radiomic features of a region of interest comprising AT and provides a tool for characterising the region of interest, in particular fat or adipose, and for non-invasive detection or identification of adipose tissue dysfunction.

The radiomic signature of the invention may be used on its own to characterise the region of interest to provide diagnostic or prognostic information, or it may be combined with existing models and risk factors, such as age, sex, hypertension, dyslipidemia, smoking, diabetes mellitus, body mass index, homeostatic model assessment insulin resistance (HOMA-IR) index, and/or subcutaneous fat volume.

The invention exploits the finding that specific imaging patterns in adipose tissue (e.g. related to tissue texture and radiodensity) are linked with distinct biological phenotypes and gene markers of adipose tissue characteristics or phenotypes indicative of AT dysfunction, such as adipocyte differentiation and adipose tissue inflammation. The radiotranscriptomic approach of the invention offers a means to non-invasively detect, identify, or diagnose adipose tissue dysfunction, something which until now has been feasible only via invasive means such as fat biopsies. The radiomic signature of the invention may be used to assess adipose tissue health or to identify adipose dysfunction, capturing the effect of risk factors on adipose tissue biology, which is of value in the field of endocrinology and diabetes. The radiomic signature may therefore be used as a metric of, or to predict, metabolic risk, for example cardiometabolic risk. For example, the radiomic signature of the invention may be used to classify patients according to their metabolic risk, i.e. their risk of developing a metabolic disorder, such as diabetes (diabetes mellitus), in particular type-II diabetes. The radiomic signature of the invention may be used to assess the response to treatment interventions. For example, the radiomic signature may be calculated before a round of treatment for a metabolic disorder and then subsequent to the round of treatment and the difference in the signature used to assess the response to the treatment.

The radiomic signature of the invention exploits the finding that the texture (i.e. the spatial non-uniformity or variability) of fat is linked to features of metabolic risk and adipose tissue dysfunction beyond simple fat volume measurements. The radiomic signature of the invention may therefore be constructed to provide a measure of the texture of the region of interest. The radiomic signature of the invention may therefore also be referred to as a texture index, for example a subcutaneous texture index (STI) if the ROI is a subcutaneous region.

The region of interest (ROI) is a region or volume of an individual's (i.e. a patient's) body comprising adipose tissue. The ROI may therefore be a region or volume of AT or may comprise or consist of AT. The adipose tissue may be subcutaneous adipose tissue (ScAT), visceral (or abdominal) adipose tissue or thoracic adipose tissue. In particular, the adipose tissue may be subcutaneous adipose tissue, which is the least affected by the biology of adjacent organs. Subcutaneous tissue, also called the hypodermis, is tissue located adjacent to and under the skin. Tissue is a complex biological structure, and may comprise cells (e.g. adipocytes, neurons, etc.) and extracellular structures and materials (such as water) which may occupy the intercellular spaces. For example, subcutaneous adipose tissue generally comprises fibroblasts, adipose cells, and macrophages. Visceral adipose tissue, sometimes referred to as abdominal or intra-abdominal adipose tissue, is located within the abdominal cavity in-between the intra-abdominal organs. Thoracic adipose tissue is located within the thoracic (or chest) cavity.

Preferably, the ROI comprises or consists of non-cardiovascular adipose tissue. For example, the adipose tissue may comprise a majority (i.e. more than 50% by volume, based on the total volume of adipose tissue) of non-cardiovascular adipose tissue. For example, the adipose tissue may comprise substantially non-cardiovascular adipose tissue. For example, the adipose tissue may comprise less than 10% (by volume based on the total volume of adipose tissue) cardiovascular adipose tissue, in particular less than 5% (by volume) cardiovascular adipose tissue. Adipose tissue may be defined as all voxels in the ROI having a radiodensity within a given range, such as from about −190 HU to about −30 HU. Cardiovascular adipose tissue is adipose tissue associated with (i.e. adjacent, attached to, or a part of) the cardiovascular system. In particular, cardiovascular adipose tissue comprises cardiac (i.e. heart) adipose and vascular adipose. For example, cardiovascular adipose may refer to epicardial, pericardial and perivascular adipose tissue. Hence, the region of interest may not contain cardiovascular adipose tissue, in particular the region of interest may not contain epicardial, pericardial or perivascular adipose tissue, or may comprise adipose tissue other than epicardial, pericardial or perivascular adipose tissue. The ROI may therefore be not adjacent to (i.e. may be remote from or spaced apart from) the organs of the cardiovascular system (i.e. cardiovascular organs such as the heart or major blood vessels such as arteries and veins). Cardiovascular adipose tissue is affected by the underlying health of the cardiovascular system, in particular by the phenotype of the organ tissue to which it is attached, for example myocardium or vascular tissue. Thus, the signature of the invention is a more reliable indicator of metabolic health, and of adipose tissue dysfunction related to metabolic health, if the ROI comprises or consists of non-cardiovascular adipose tissue, which reflects metabolic health and the health of the adipose itself more directly than cardiovascular adipose.

The invention exploits a radiomic approach. Radiomics is a field of imaging in which a large amount of quantitative information is extracted from imaging data using data-characterization algorithms. The resulting features, referred to as radiomic features, range from simple volumetric, shape-related or first order statistics (such as mean or median attenuation), to second and higher order statistics that describe the texture of a segmented volume or region and the spatial relationship of voxels with similar or different attenuation values. Such features can identify imaging patterns of significant clinical value that cannot be recognized by the naked eye and have the potential to maximize the diagnostic yield of non-invasive AT phenotyping.

The signature of the invention is derived and calculated on the basis of radiomic features, for example those extracted from medical imaging data. In particular, the medical imaging data from which the radiomic features are extracted correspond to a region of interest (ROI), and optionally also to other tissue adjacent or surrounding the ROI, such as the skin. The medical imaging data typically comprise radiodensity (or attenuation) values, usually expressed in Hounsfield Units (HU), for a plurality of voxels of the relevant region, in this case the ROI, and optionally also the adjacent tissues.

The medical imaging data are preferably computed tomography (CT) data, but other forms of medical imaging data (e.g. radiography data) that provide attenuation (or radiodensity) data for voxels of the imaged region may be used instead, such as three-dimensional computed laminography data. Typically, the medical imaging data used in the invention are three-dimensional imaging data. Throughout the following, where CT or another medical imaging technique is referred to, it should be understood that other suitable medical imaging techniques could alternatively be used.

The ROI may be identified by a person such as an operator, for example by manual contouring (delineation). The operator may identify the ROI through an inspection of the imaging data, for example the CT image. Alternatively, or in addition to identifying the spatial identification of the ROI using manual contouring, the ROI may be identified by applying a radiodensity (or attenuation) mask to the data and identifying the ROI as including only those voxels having a radiodensity falling within a given or predetermined range. For example, the ROI may include only those voxels having a radiodensity in the Hounsfield Unit range of about −190 HU to about +30 HU and optionally also located within the contoured region identified by the operator. In particular, the ROI may be defined as all voxels having a radiodensity in the Hounsfield Unit range of about −190 HU to about −30 HU. This range of attenuation values generally corresponds to the radiodensity of adipose tissue. However, other ranges could be used or included, for example about −30 to about +30 Hounsfield Units, which generally corresponds to the radiodensity of water.

The ROI may be segmented prior to calculating the radiomic features and the radiomic features calculated from the segmented data. The segmented volume or region corresponds to the ROI, and segmentation may remove data corresponding to voxels that are outside of the ROI. Segmentation may therefore be achieved by identifying the ROI, as described above, and then removing any voxels from the data that are identified as not being part of the ROI, for example those voxels corresponding to surrounding or adjacent tissue voxels. The segmented ROI may then be extracted and used to calculate the radiomic features.

Calculation of the radiomic features from the medical imaging data may be performed using a computer program, or software. Various commercially available software packages exist for this purpose, such as 3D Slicer (available at http://www.slicer.org; see Fedorov, A. et al. 3D Slicer as an image computing platform for the Quantitative Imaging Network. Magn Reson Imaging 30, 1323-1341, doi: 10.1016/j.mri.2012.05.001 (2012)). The radiomic features may be shape-related statistics, first-order statistics, or texture statistics (e.g. second and higher order statistics). Shape-related and first-order radiomic features may be calculated using the raw radiodensity (HU) values of the ROI voxels. For calculation of texture features (e.g. Gray Level Co-occurrence Matrix [GLCM], Gray Level Dependence Matrix [GLDM], Gray Level Run-Length Matrix [GLRLM], Gray Level Size Zone Matrix [GLSZM], and Neighbouring Gray Tone Difference Matrix [NGTDM], see Tables R1-R7), ROI voxel radiodensity or attenuation values are preferably discretized into a plurality of bins, preferably into 16 bins, preferably of equal width (e.g. width of ten HU), to reduce noise while allowing a sufficient resolution to detect biologically significant spatial changes in ROI attenuation. Discretization into 16 bins is recommended as the optimal approach to increase the signal-to-noise ratio of images for radiomic analysis. However, discretization into more or fewer than 16 bins is also possible. To enforce symmetrical, rotationally-invariant results, some or all of the radiomic features, in particular the texture statistics (GLCM etc.), may be calculated in all (orthogonal) directions (e.g. the four the directions of the four sides of a square pixel or voxel) and then averaged (e.g. using the mean or other average of the individually calculated values of the feature in each of the directions).

Some or all of the radiomic features, in particular those relating to first order and texture-based statistics, may also be calculated for three-dimensional wavelet transformations of the original image data resulting in a number of additional sets of radiomic features, for example as described by Guo et al. (Guo X, Liu X, Wang H, et al. Enhanced CT images by the wavelet transform improving diagnostic accuracy of chest nodules. J Digit Imaging 2011; 24(1): 44-9). Wavelet transformation decomposes the data into high and low frequency components. At high frequency (shorter time intervals), the resulting wavelets can capture discontinuities, ruptures and singularities in the original data. At low frequency (longer time intervals), the wavelets characterize the coarse structure of the data to identify the long-term trends. Thus, the wavelet analysis allows extraction of hidden and significant temporal features of the original data, while improving the signal-to-noise ratio of imaging studies. The data may be decomposed by a discrete wavelet transform into a plurality (e.g. eight) wavelet decompositions by passing the data through a multi-level (e.g. three level) filter bank. At each level, the data are decomposed into high- and low-frequency components by high- and low-pass filters, respectively. Thus, if a three level filter bank is used, eight wavelet decompositions result, corresponding to HHH, HHL, HLH, HLL, LHH, LHL, LLH and LLL, where H refers to "high-pass", and L refers to "low-pass". Of course, more or fewer than eight levels could alternatively be used to decompose the data. Such decompositions may be performed using widely available software, such as the Slicer Radiomics software package which incorporates the Pyradiomics library. Optionally, the radiomic features may all be calculated on the basis of the original (raw) data, i.e. with no wavelet transformation applied. Thus, where lists, groups or clusters of radiomic features are disclosed herein, it should be understood that these could be reduced to exclude those radiomic features that are calculated on the basis of wavelet transformations. Where a radiomic feature is calculated on the basis of a wavelet decomposition or transformation of the data this is denoted by a suffix indicating which wavelet decomposition the radiomic feature has been calculated on the basis of (e.g. HHH for high-pass, high-pass, high-pass). So, for example, "Skewness LLL" denotes the radiomic feature "Skewness" as calculated on the basis of the LLL wavelet decomposition. Where no suffix is present, the radiomic feature is calculated on the basis of the original (or raw) data.

Deriving a Radiomic Signature

The invention provides a method for deriving a radiomic signature for characterising a ROI (for example a region comprising or consisting of adipose tissue or fat), for example for detecting or identifying adipose tissue dysfunction or for predicting metabolic risk, e.g. the risk of developing a metabolic disorder or disease, such as diabetes. The radiomic signature is derived using medical imaging data for a plurality of individuals, and data indicative of, or associated with, adipose tissue dysfunction for each of the plurality of individuals (e.g. patients). In particular, the data indicative of adipose tissue dysfunction may comprise or consist one or more markers (e.g. a biomarker) of adipose tissue dysfunction, such as the presence or absence of a metabolic disorder, adipose tissue phenotypes associated with adipose tissue dysfunction, or any other information allowing an inference to be made as to whether an individual has or does not have adipose tissue dysfunction.

Figure 4A:
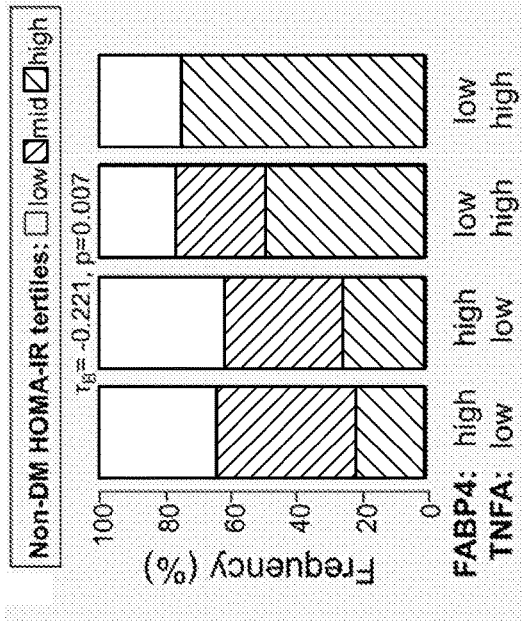
FIGS. 4(a) and (b) illustrate the association of adipose tissue gene expression profiles (FABP4 as a surrogate marker of adipocyte differentiation and TNFA as surrogate marker of inflammation) with diabetes and insulin resistance (HOMO-IR) in non-diabetics, respectively.

Adipose tissue dysfunction is a widely understood to mean the abnormal functioning of adipose, resulting, for example, in inflammation and fibrosis. As previously mentioned, adipose dysfunction plays a crucial role in the development of metabolic disorders such as insulin resistance and diabetes mellitus. The data indicative of adipose tissue dysfunction may therefore include information regarding the presence or absence (i.e. whether an individual has or does not have) of a metabolic disorder associated with adipose tissue dysfunction (such as diabetes or insulin resistance) for each of the individuals, which may be used as a marker for adipose dysfunction. In particular, the data may include measurements of one or more features of adipose tissue biology (i.e. adipose tissue phenotypes) that are associated with and/or are characteristic of adipose tissue dysfunction, such as adipocyte hyperplasia or hypertrophy, inflammation, adipogenesis (adipocyte differentiation), and/or fibrosis, and these may be used as a marker of adipose tissue dysfunction. Alternatively (or additionally), surrogate biomarkers of these features of adipose tissue biology, such as selected gene expression profiles may be used. In particular, gene expression profiles that are markers of characteristics of adipose tissue dysfunction may be used, for example the data may include gene expression profiles of FABP4 (fatty acid binding protein 4, associated with adipogenesis) and/or TNFA (tumor necrosis factor alpha, associated with inflammation). In particular, as demonstrated in the following Examples section and in FIGS. 4(a) and (b), both FABP4 and TNFA gene expression profiles may be used, with high TNFA expression combined with low FABP4 expression used as a surrogate marker of adipose tissue dysfunction and taken to indicate adipose dysfunction. In this context, "high" and "low" may be defined relative to the median value (or other average, such as mean) of the relevant gene expression, for example as measured for the plurality of individuals or other population. Therefore, "high" may include values above (and optionally also equal to) the median value and "low" may include values below (and optionally also equal to) the median value. Alternatively, other definitions of "high" and "low" are possible. For example, "high" may mean in the highest tertile or quartile, and "low" in the lowest tertile, or quartile. Typically, however, it will be the case that the upper limit of "low" will be below (or equal) to the average (e.g. mean or median) value and the lower limit of "high" will be above (or equal to) the average value. The individuals may therefore be classified according to their gene expression profiles and those with certain gene expression profiles, such as those described above, classified or identified as having adipose tissue dysfunction. The other individuals may be classified or identified as not having adipose tissue dysfunction. The plurality of individuals may each be identified as having or not having (in particular at the time when the medical imaging data were collected) adipose tissue dysfunction based on the marker, for example the value of the marker.

A stepwise approach may be followed to develop a radiomic signature. First, a plurality of radiomic features are calculated from the medical imaging data for each of the plurality of individuals, for example as described above. The radiomic features may comprise a selection or all of the radiomic features as defined in Tables R1-R7, and each of the radiomic features may be calculated based on the raw image data and/or on one or more wavelet transformations of the image data (or wavelet decompositions), as described above. Preferably, each of the radiomic features is calculated for the raw image data and for the aforementioned eight three-dimensional wavelet decompositions of the image data.

Unstable features may be removed from the plurality of radiomic features. A z-score transformation may be applied to the features (i.e. expressing the values of the radiomic features in terms of the number of standard deviations from the mean) and the stability analysis performed on the basis of the z-scores. The stability analysis may comprise calculating the scan-rescan stability of the radiomic features (i.e. the stability over multiple imaging data acquisitions or scans) and/or the stability over multiple or repeat region of interest delineations (e.g. segmentation or contouring). The multiple delineation stability analysis may comprise calculating the stability over multiple delineations, each performed by different operators or individuals. Preferably the stability analysis comprises performing both the scan-rescan stability and the multiple delineation stability and only features that are found to be stable according to both analyses are retained. The stability may be measured by the intraclass correlation coefficient (ICC) and unstable radiomic features may be identified as those having an intraclass correlation coefficient (ICC) in repeat imaging data acquisitions (e.g. imaging scans) and/or multiple delineation below a stability threshold. For example, the stability threshold may be at least about 0.9, for example about 0.9, so that all radiomic features having an ICC<0.9 are excluded. However, other stability thresholds may be used instead, such as 0.85 or 0.95. The scan-rescan ICC may be calculated for a plurality of repeat scans, for example two to ten scans, in particular two or ten scans. In other words, a stability analysis may be performed on the radiomic features and unstable radiomic features removed from the plurality of radiomic features. The stability analyses may be performed on the basis of the imaging data for the plurality of individuals, or may be performed using other data, for example reference data such as the RIDER dataset (RIDER: The Reference Image Database to Evaluate Therapy Response; obtained online from https://wiki.cancerimagingarchive.net/display/Public/RIDER+Collections; jsessionid=C78203F71E49C7EA3A43E0D213CE5555).

Collinearity of the retained radiomic features (i.e. the stable radiomic features) may then be reduced or eliminated by removing pairwise correlations, i.e. by removing at least one of each pair of identified collinear radiomic features. The removal of pairwise correlations may be performed in a stepwise manner. Collinear radiomic features may be identified as those that are correlated with each other to a degree at least equal to a given correlation threshold. The correlation threshold preferably applies to both positive and negative correlations, for example the correlation threshold may be expressed as a modulus. The pairwise correlations may be calculated using Spearman's rho coefficient and the correlation threshold may be at least about |rho|=0.75, for example about |rho|=0.75, so that all pairwise correlations at the level of |rho|≥0.75 are eliminated. Preferably, the correlation threshold may be at least about |rho|=0.9, for example about |rho|=0.9. As will be readily understood in the field, the correlation or collinearity is a measure of how closely two radiomic features vary together from one individual to the next and may be calculated on the basis of the measured radiomic feature values for the plurality of individuals.

For example, when a pair of collinear radiomic features is identified, one of the two features is preferably eliminated from the plurality of features. For example, the radiomic feature that is calculated from the data to be the less strongly associated with the AT dysfunction of the two may be eliminated and the radiomic feature that is most strongly associated with AT dysfunction may be retained, but this is not necessary and either could be retained or eliminated. For example, the collinear elimination step may be performed in an unsupervised way without taking into account AT dysfunction and the algorithm may eliminate the most redundant feature that contributes the least to the variation of the study population (e.g. the feature with the smaller variance as measured across the plurality of individuals). In one example, when a pair of collinear features is identified, the feature with the largest average (e.g. mean) absolute correlation (i.e. the average correlation value (or average modulus or square correlation value) with all other radiomic features) is removed. This may be performed in a stepwise manner until no collinear radiomic features remain.

The collinear elimination step may be performed using an algorithm or function (for example, the function claret::findCorrelation, R package, see Kuhn, M. & Johnson, K. Applied Predictive Modelling. (Springer, 2013)). For example, the function or algorithm may construct a pairwise correlation matrix containing pairwise correlations between the radiomic features. The function may then search through the correlation matrix and return a vector of integers corresponding to columns to remove to reduce pairwise correlations. The radiomic features to which these columns correspond may then be removed from the plurality of radiomic features. In deciding which columns to remove, the algorithm may first identify pairwise correlations between radiomic features. When two collinear radiomic features are identified, the algorithm then identifies the column corresponding to the feature with the largest mean absolute correlation for removal.

Regardless of how the collinear elimination step is performed, the end result is preferably the production of a reduced plurality of radiomic features in which each of the features is correlated with each of the other remaining features to a degree less than the correlation threshold. In other words, the method may involve the step of removing radiomic features to eliminate collinearity between the radiomic features so that none of the remaining radiomic features is collinear with any of the other remaining radiomic features. This may involve the calculation of pairwise correlations between radiomic features and removing at least one of any identified pair of collinear features.

The reduction of collinearity has the advantage that the redundancy of the radiomic features is reduced. Collinear features, i.e. those that tend to vary in the same way between individuals, are highly likely to be sensitive to the same or similar phenotypic aspects of the AT. Removing collinear features therefore ensures an increased diversity of information in the final signature, with each radiomic feature included in the final signature representing a different phenotypic characteristics of the AT.

The radiomic signature may then be constructed based on at least two of the remaining radiomic features that survive whichever of the steps described above are performed (e.g. stability analysis and/or collinearity elimination). For example the radiomic signature may then be constructed based on at least two of the reduced plurality of non-collinear radiomic features that survive the collinear elimination step. The reduced plurality of features that survive the collinear elimination step are otherwise known as the "original features". However, since the eliminated radiomic features are each strongly correlated with at least one of the original features, a signature in which one or more of the original features is replaced by one of the features that is collinear with the replaced original feature will generally perform similarly to a signature calculated on the basis of only the original features. For example, it is possible to swap one of the original features for one of the features calculated as being collinear with that original feature and the signature should perform similarly.

The process of constructing the radiomic signature may therefore involve the construction of "groups" of radiomic features (each group comprising one of the original features) in which each of the radiomic features in each group is collinear with at least the "original" feature in that group (i.e. the feature of that group that survived the collinear elimination step, e.g.). In this way, each original feature has associated with it its own group of collinear equivalents, which are radiomic features that are calculated to be collinear with that original feature from the data. These groups of collinear equivalents may be constructed for each of the original radiomic features, or only for a subset of the original radiomic features, such as those identified as maximising the association of the signature with AT dysfunction, for example by a feature selection algorithm (see below). The construction of these groups may be performed instead of the collinear elimination step. For example, instead of eliminating one of each pair of collinear features, the collinear features may be allocated to the same group. Alternatively, the pairwise elimination step may be performed as described above, and then, once the original features are identified, the eliminated features may be reintroduced by allocating them to the group of the original feature with which they are most strongly correlated or collinear with.

However, regardless of how the groups are constructed, the end result should be that each radiomic feature is allocated to the same group(s) as the original radiomic feature(s) that it is collinear with. If a radiomic feature is collinear with two "original" features, it is preferably allocated to the group of the original feature with which it is most collinear with, but it may be allocated to the groups of all the original features with which it is collinear.

The "original" radiomic feature in each group therefore represents a "partner" radiomic feature to each of the other radiomic features in that group, with each of the radiomic features in each group being collinear with its "partner" feature. The original radiomic feature may therefore be considered its own "partner" radiomic feature in this sense because it is perfectly collinear with itself.

Although the "original" features are, by definition, not collinear with each other, some of the original features will be more similar, or inter-correlated with each other, than others. The "original" radiomic features may therefore themselves be grouped or "clustered" into a plurality of clusters of similar, or correlated, features. As before, the degree of correlation between radiomic features is a measure of the extent to which two radiomic features tend to vary with one another between different individuals. The pairwise correlations may be calculated using Spearman's rho coefficient or other measures of correlation, such as Pearson's correlation coefficient. The clustering may be performed, for example, using a hierarchical clustering method (such as a hierarchical clustering algorithm) to sort the significant radiomic features into the plurality of clusters. The hierarchical clustering may be performed unsupervised, i.e. independently of the strength of the correlations of the radiomic features with AT dysfunction (or the marker thereof). In other words, the clustering may be performed on the strength of the correlations of the features with one another so that radiomic features are clustered together with those that they are most correlated with. Specifically, the intra-cluster correlations may be stronger than the inter-cluster correlations, i.e. the correlations between features within a cluster are stronger than those between features in different clusters. The final identification of the clusters may be performed by inspection of the correlation data by a person, e.g. an operator. For example, the operator may inspect a dendrogram representative of the hierarchical clustering of the radiomic features and/or a two-dimensional correlation plot (or heatmap) which plots the correlations of each of the radiomic features with each other radiomic features (and itself) and may identify the clusters based on this inspection of the radiomic feature inter-correlation data. In the correlation heatmap the radiomic features may be arranged along the x- and y-axes of the correlation plot in the order determined from the hierarchical clustering (i.e. with the features being located adjacent to the features with which they are most closely associated or correlated). This visual inspection may be used together with the hierarchical clustering to identify the appropriate clusters of radiomic features. Alternatively, the clusters may be identified through the hierarchical clustering or visual inspection alone.

The radiomic signature may advantageously be constructed based on at least two of the original features selected from different clusters, as identified in the cluster analysis. For example, the radiomic signature may be constructed based on at least one radiomic feature selected from each cluster. If collinear equivalents of the original features are included in the signature in place of the original features, the collinear equivalents preferably correspond to original radiomic features belonging to different clusters. Preferably, the radiomic signature comprises at least two of the original radiomic features (or their collinear equivalents) that are found to maximise the signature's accuracy for predicting the cardiac condition or myocardial disease. Other radiomic features may also be included in the signature, for example two or more radiomic features from any or all of the clusters may be included in the signature. However, in order to provide a signature more strongly associated with AT dysfunction, and therefore of enhanced diagnostic and prognostic usefulness, it is preferable to include at least two radiomic features, each from a different cluster. Again, this is because features from different clusters provide complementary phenotypic information relating to the ROI because they are correlated with one another only weakly. In particular, radiomic features from the different clusters are likely to be sensitive to different phenotypic characteristics of the ROI because they have been found not to vary in a similar manner to one another, which demonstrates that they are sensitive to different phenotypic characteristics of the ROI. The radiomic signature should therefore preferably be calculated on the basis of (the measured values of) at least two radiomic features, each selected from a different cluster. For example, the radiomic signature may comprise at least three radiomic features, each selected from a different cluster. Preferably, the initial radiomic signature may comprise one radiomic feature from each cluster.

The radiomic signature may be constructed based on at least two (or all) of the reduced plurality of features (e.g. the "original" features), or collinear equivalents thereof. For example, if the groups of collinear equivalents described above are constructed, the initial radiomic signature may be constructed from at least two radiomic features, each being selected from a different group.

The radiomic signature may be constructed using one or more machine learning algorithms. The machine learning algorithm may comprise a recursive feature elimination algorithm, for example a random forest algorithm, and may comprise multi-fold (e.g. 5-fold) cross-validation. Some (preferably all) of the remaining, or "original", radiomic features that survive the collinear elimination step may be input into the machine learning algorithm(s) to identify the optimum number of and identity of the radiomic features that maximises the association of the radiomic signature with AT dysfunction. As mentioned above, collinear equivalents may be used in place of, or in addition to, the original radiomic features and input into the machine learning algorithm(s). For example, the machine learning algorithm(s) may refine the contribution of each of the input radiomic features to the signature to improve the association of the radiomic signature with AT dysfunction (e.g. the marker of AT). In so doing, the machine learning algorithm may identify a subset of the radiomic features that maximise the signature's ability to distinguish or identify AT dysfunction and the radiomic signature may be calculated on the basis of at least that subset of radiomic features. In addition to the radiomic features, clinical profile characteristics (e.g. age, sex, diabetes mellitus, dyslipidemia, hypertension, HOMA-IR, body mass index and subcutaneous fat area) may also be input into the machine learning algorithm and may optionally also be included in the final signature.

In particular, the contributions of the radiomic features to the signature may be refined using a machine learning algorithm to increase or maximise the association of the signature with the cardiac condition or myocardial disease. For example, a plurality (preferably all) of the original radiomic features (i.e. those that survive the collinear elimination step) and/or collinear equivalents of the original radiomic features (e.g. those belonging to the same group) may be input into a first machine learning algorithm. The first machine learning algorithm may be used to identify the optimum number of and identity of the radiomic features that are to be included in the signature, in particular to maximize its accuracy for discriminating for AT dysfunction. In other words, the construction of the radiomic signature may comprise a feature selection step in which the radiomic features to be included in the signature are selected. In the feature selection step a feature selection algorithm (e.g. a machine learning algorithm) may select a subset of the radiomic features to be included in the final signature, in particular that are predicted to maximise the association of the final signature with AT dysfunction. This has the advantage of reducing the complexity optimising the final signature because it reduces the number of radiomic features that need to be considered. The first machine learning algorithm that performs this feature selection step may use recursive feature elimination, for example with a random forest algorithm. However, other algorithms could alternatively be used. The first machine learning algorithm may be constrained to require the resulting signature to comprise at least two radiomic features selected from different clusters identified in the cluster analysis step (e.g. using the clustering algorithm). For example, the machine learning algorithm may be constrained to require the resulting signature to comprise at least one radiomic feature selected from each of the clusters.

Once the number and identity of the radiomic features to be included in the signature are identified, a second machine learning algorithm may be used to optimise the contributions of each of the features identified by the first machine learning algorithm to the signature. In other words, the construction of the radiomic signature may comprise the step of refining or optimising the radiomic signature to increase or maximise its association with AT dysfunction using a second machine learning algorithm. The second machine learning algorithm may be a logistic regression algorithm. The signature may be derived or refined using the data for a training cohort and validated using data for a test cohort. For example, the signature may be constructed using internal cross-validation. The internal cross validation may be multi-fold, for example 5-fold.

Alternatively, the signature may be constructed from the radiomic features, for example from the "original" radiomic features, using a single machine learning algorithm, rather than in the two-step process described above. For example, a single machine learning algorithm could be used to identify the features to be included in the final signature and to refine or optimise the signature. For example, the number of radiomic features to be included in the final signature may be preselected or predetermined and input as a parameter into the machine learning algorithm, or may be left open and selected by the machine learning algorithm itself, which also refines and optimises the radiomic signature. In other words, the machine learning algorithm may include a feature selection function.

In general, the construction of the radiomic signature involves refining or optimising the radiomic signature, for example the contribution of each of each of the radiomic features to the signature, to improve the correlation or association of the signature with AT dysfunction based on the data. For example, the signature may comprise a weighted sum of the values of each of the radiomic features included in the initial signature, and the weighing of each of the radiomic features may be progressively optimised or refined. The coefficients by which each of the radiomic features is multiplied are generally referred to as beta ($\beta$) coefficients, and it is these beta coefficients that may be optimised or refined. The association of the radiomic signature with AT dysfunction may be calculated based on a receiver operating characteristic (ROC) curve analysis, in particular using an area under the curve (AUC) measurement (i.e. the C-statistic), as will be readily understood by those skilled in the art.

Preferably, it is the original features that survive the collinear elimination step that are input into the machine learning algorithm(s) and the machine learning algorithm(s) identifies a subset of these original features that maximise the signature's accuracy for classification of AT dysfunction. The radiomic signature is preferably then constructed from two or more radiomic features that belong to the groups of collinear equivalents corresponding to these original radiomic features, with the two or more radiomic features being selected from different groups.

This approach is advantageous because in order to provide a signature more strongly associated with AT dysfunction, and therefore of enhanced diagnostic and prognostic usefulness, it is preferable for the signature to include at least two radiomic features, each from a different group. This is because features from different groups (and therefore corresponding to different non-collinear original features) provide complementary information relating to the ROI. In particular, radiomic features from different groups will be sensitive to different phenotypic characteristics of the ROI because they are collinear with different "original" or "partner" features. For example, the initial radiomic signature may comprise at least three radiomic features, each selected from a different group. Alternatively, the initial radiomic signature may comprise at least four radiomic features, each selected from a different group. Alternatively, the initial radiomic signature may comprise at least five radiomic features, each selected from a different group. Preferably, the initial radiomic signature may comprise one radiomic feature from each group.

As mentioned above, the signature may comprise a weighted sum of the calculated values of a plurality of radiomic features. The signature may also include other terms, such as the addition or subtraction of a constant, or multiplication by a factor. However, typically the signature will be linearly related to the weighted sum of radiomic feature values in some way.

The radiomic signature may take the form of, or include the term (for example, the signature may be calculated on the basis of a function including the term):

$$\Sigma b_i r f_i + c$$

where c is a constant (which can be zero or non-zero), $b_i$ is the weighting coefficient (or beta parameter) for the radiomic feature i, and $rf_i$ is the measured value of the radiomic feature i. The constant c is not necessary but may be included to ensure that all resulting values are either positive or negative.

The Radiomic Signature

The radiomic signature of the invention is calculated on the basis of measured values of radiomic features obtained from medical imaging data. In particular, the radiomic signature is preferably calculated on the basis of at least two radiomic features.

To improve the prognostic and diagnostic value of the signature, the signature is preferably calculated on the basis of at least two different radiomic features selected from different clusters of similar or correlated original radiomic features, as described above. This reduces redundancy and improves the diversity of information included in the calculation of the signature because the features from different clusters relate to different textural aspects of the ROI.

Figure 3A:
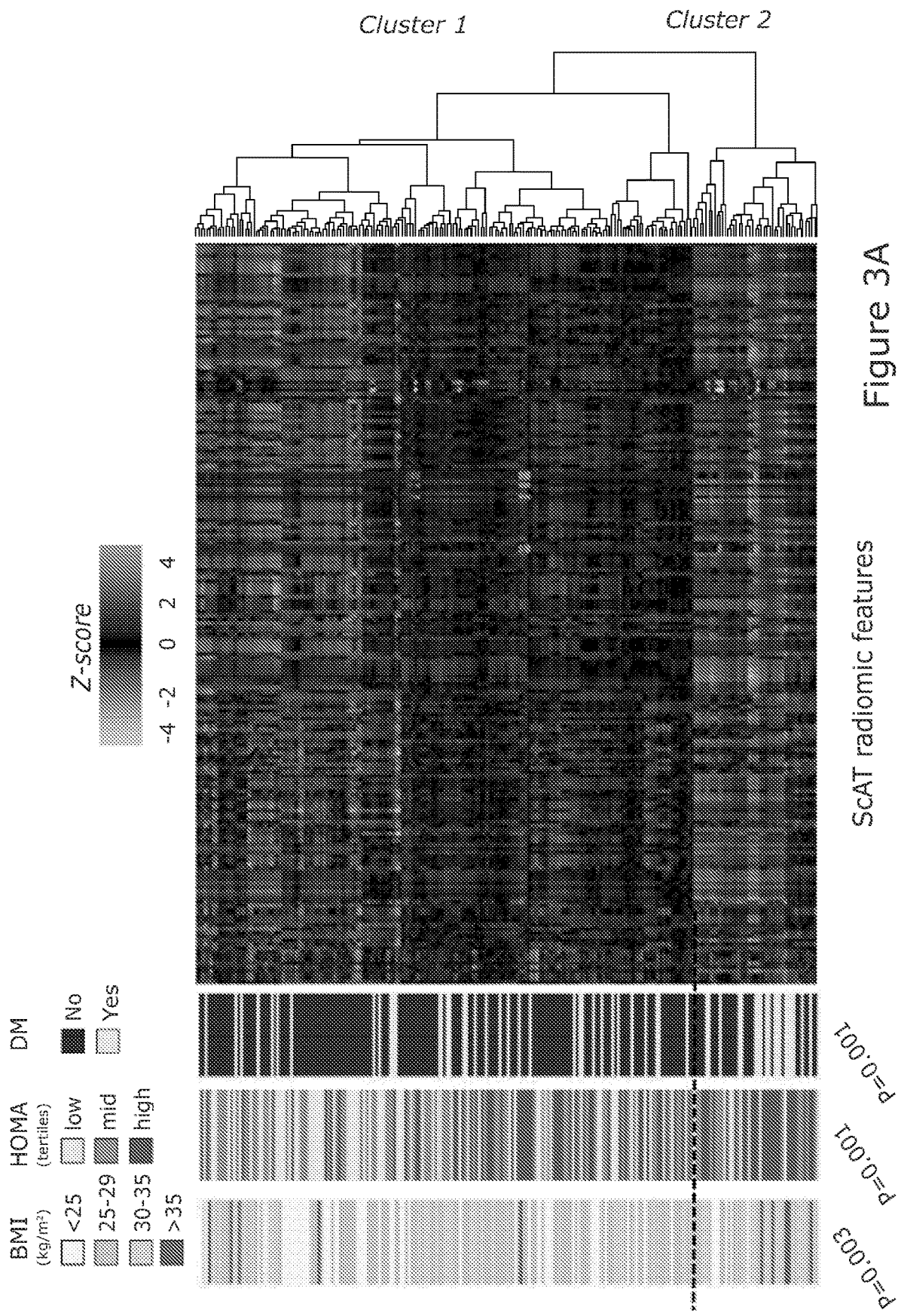
FIG. 3(a) illustrates unsupervised hierarchical clustering of the patients of Arm 1 using the 196 stable radiomic features (after stability assessment) in the population of Arm 1. Distinct radiomic features are represented on x-axis, and the number of observations (n=225 patients) on y-axis. A row dendrogram denotes the two distinct clusters of patients.
Figure 3B:
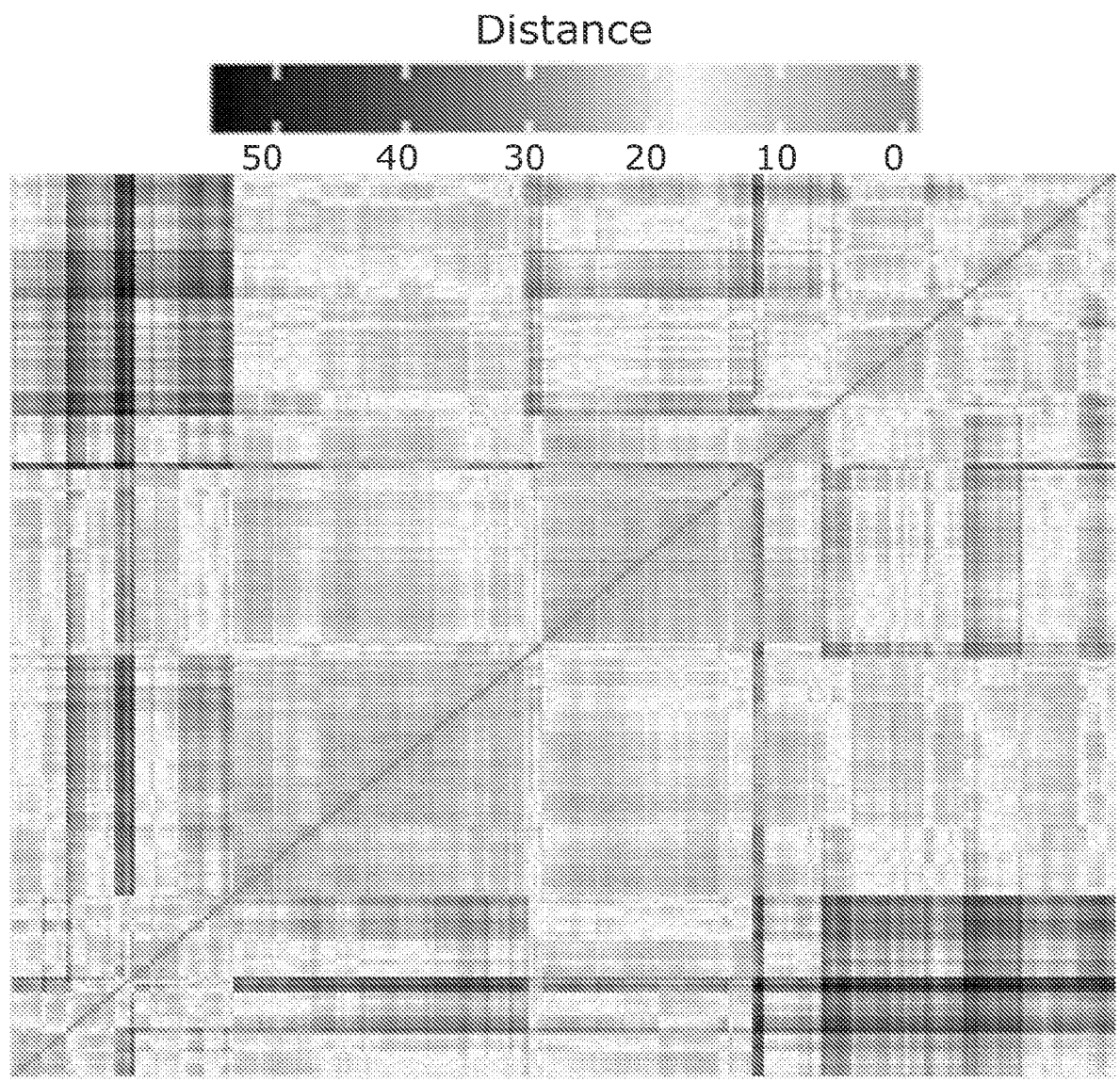
FIG. 3(b) is a similarity-dissimilarity plot showing the Euclidean distance (i.e, dissimilarity) between the selected radiomic features (n=196 after stability assessment) for visual recognition of possible clusters in the patients of the Arm 1 cohort.
Figure 3C:
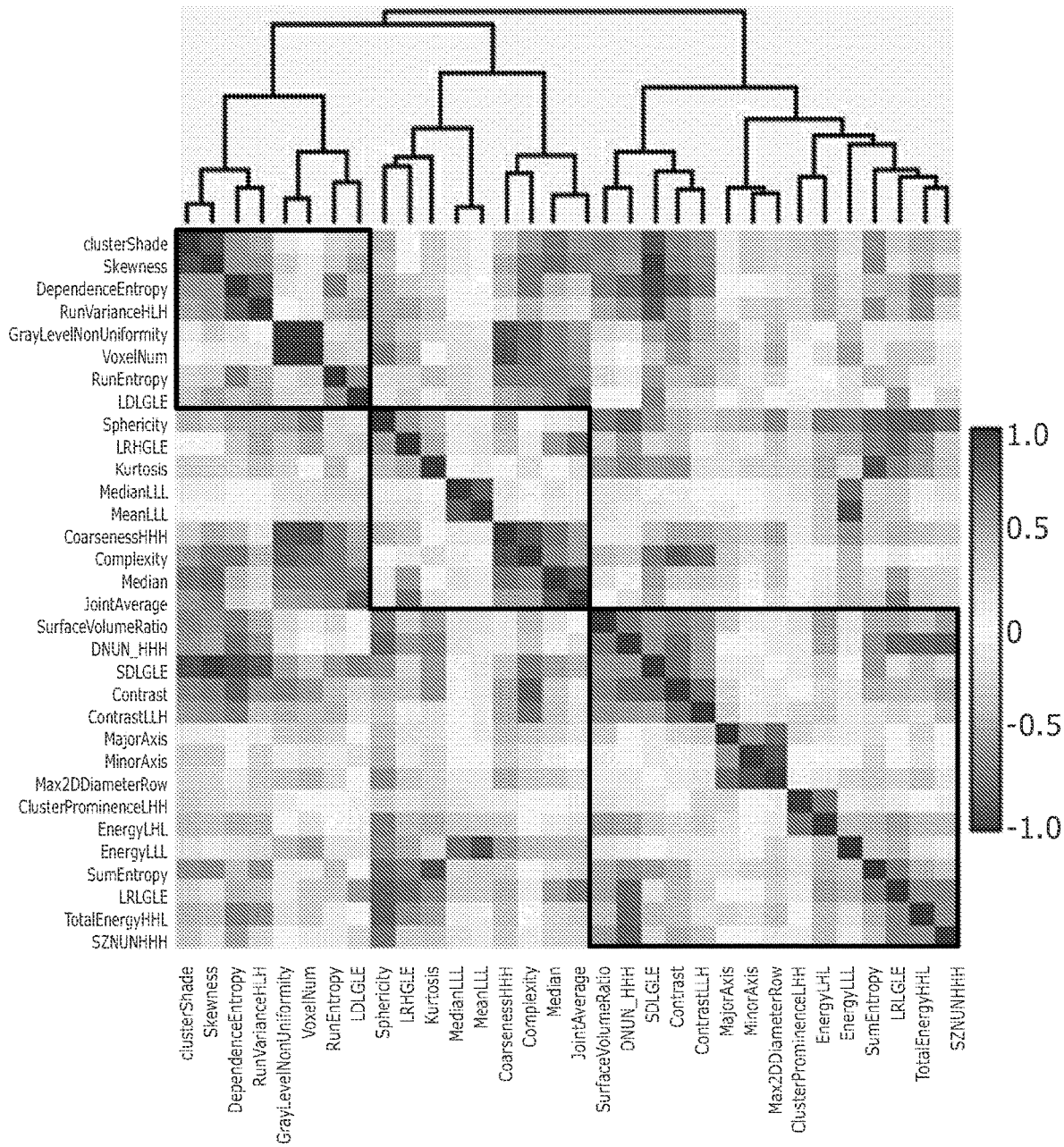
FIG. 3(c) is a correlation plot of the 32 filtered (non-collinear) radiomic features after excluding highly correlated (i.e. collinear) features (|rho|>0.90). P-values from chi-square.

Three clusters (A-C) of the "original" (i.e. non-collinear) radiomic features have been identified using a hierarchical clustering algorithm (see the Examples and FIG. 3(c)). The members of the three clusters are identified in Table 1 (and FIG. 3(c)). The radiomic signature may comprise at least two of the non-collinear radiomic features from Table 1. Advantageously, the radiomic signature may be calculated on the basis of radiomic features selected from at least two of the clusters A-C identified in Table 1, the at least two radiomic features being selected from different clusters. Preferably, the radiomic signature may be calculated on the basis of at least one radiomic feature selected from each of the clusters A-C identified in Table 1.

TABLE 1

Radiomic feature clusters

| Cluster | Radiomic features |
| --- | --- |
| A | Large Dependence Low Gray Level Emphasis |
| A | Run Entropy |
| A | Dependence Entropy |
| A | Cluster Shade |
| A | Skewness |
| A | Run Variance HLH |
| A | Voxel Number |
| A | Gray Level Non Uniformity |
| B | Mean LLL |
| B | Median LLL |
| B | Joint Average |
| B | Median |
| B | Complexity |
| B | Long Run High Gray Level Emphasis |
| B | Sphericity |
| B | Kurtosis |
| B | Coarseness HHH |
| C | Major Axis |
| C | Small Dependence High Gray Level Emphasis |
| C | Minor Axis |
| C | Energy LLL |
| C | Maximum 2D Diameter Row |
| C | Long Run Low Gray Level Emphasis |
| C | Total Energy HHL |
| C | Dependence Non Uniformity Normalized HHH |
| C | Contrast (GLCM) |
| C | Surface Volume Ratio |
| C | Sum Entropy |
| C | Size Zone Non Uniformity Normalized HHH |
| C | Cluster Prominence LHH |
| C | Contrast LLH (GLCM) |
| C | Energy LHL |

Five radiomic features were found to maximise the radiomic signature's association with AT dysfunction (see the following Examples), and these are listed in Table 2. The radiomic signature may advantageously be calculated on the basis of at least two of the radiomic features from Table 2. Preferably, the radiomic signature is calculated on the basis of at least two radiomic features from Table 2, each of the at least two radiomic features being selected from different clusters. Further preferably, the radiomic signature may be calculated on the basis of at least one radiomic feature selected from each of the clusters A-C identified in Table 2. To maximise the radiomic signature's association with AT dysfunction the radiomic signature is preferably calculated on the basis of all of the radiomic features listed in Table 2.

TABLE 2

Further optimised radiomic feature clusters

| Cluster | Radiomic features |
| --- | --- |
| A | Large Dependence Low Gray Level Emphasis |
| A | Run Entropy |

TABLE 2-continued

Further optimised radiomic feature clusters

| Cluster | Radiomic features |
|---|---|
| A | Dependence Entropy |
| B | Mean LLL |
| C | Total Energy HHL |

As previously mentioned, the "original" radiomic features of Tables 1 and 2 may be substituted with other radiomic features that are collinear with the replaced "original" radiomic feature (i.e. collinear equivalents) to obtain a signature of similar diagnostic and prognostic usefulness. The radiomic signature may therefore be calculated on the basis of (i.e. comprise) at least two of the radiomic features selected from Table 3. Each of the groups identified in Table 3 includes one of the five "original" radiomic features listed in Table 2 that have been found to maximise the association of the signature with AT dysfunction along with those radiomic features that have been calculated to be collinear with that original radiomic feature to a degree of at least |rho|=0.75, where rho is Spearman's rho. Thus, the radiomic signature may be constructed as set out above, but with one or more of the radiomic features of Table 2 being replaced with a radiomic feature that is collinear with that feature, as set out in Table 3. For example, the radiomic signature may be calculated on the basis of at least two radiomic features selected from different groups of Table 3. For example, the radiomic signature may be calculated on the basis of at least three radiomic features selected from different groups of Table 3. For example, the radiomic signature may be calculated on the basis of at least four radiomic features selected from different groups of Table 3. For example, the radiomic signature may be calculated on the basis of at least five radiomic features selected from different groups of Table 3. In particular, the radiomic signature may be calculated on the basis of at least two radiomic features that are selected from groups corresponding to original features belonging to different clusters A-C. In particular, the radiomic signature may be calculated on the basis of at least one radiomic feature selected from each of the clusters A-C identified in Table 3 below.

TABLE 3

Groups of radiomic features collinear with radiomic features of Table 2

| Radiomic features | \|rho\| with original feature |
|---|---|
| Group 1 (cluster A) | |
| Large Dependence Low Gray Level Emphasis | 1.000 |
| Sum Average | 0.779 |
| Joint Average | 0.779 |
| High Gray Level Emphasis | 0.756 |
| Short Run High Gray Level Emphasis | 0.748 |
| Autocorrelation | 0.745 |
| High Gray Level Run Emphasis | 0.738 |
| Group 2 (cluster A) | |
| Total Energy HHL | 1.000 |
| Energy HHL | 0.974 |
| Size Zone Non Uniformity HHH | 0.934 |
| Size Zone Non Uniformity HLH | 0.907 |
| Size Zone Non Uniformity LHH | 0.89 |
| Gray Level Non Uniformity Normalized HHL (GLDM) | 0.886 |
| Inverse Variance HHL | 0.88 |
| Gray Level Non Uniformity Normalized HHL (GLSZM) | 0.879 |

TABLE 3-continued

Groups of radiomic features collinear with radiomic features of Table 2

| Radiomic features | \|rho\| with original feature |
|---|---|
| Size Zone Non Uniformity LHL | 0.878 |
| Run Length Non Uniformity HHH | 0.865 |
| Size Zone Non Uniformity HLL | 0.863 |
| Dependence Non Uniformity HHL | 0.863 |
| Gray Level Non Uniformity Normalized HHH (GLDM) | 0.857 |
| Inverse Difference Moment HHH | 0.855 |
| Inverse Difference HHH | 0.855 |
| Uniformity HHH | 0.854 |
| Informational Measure of Correlation 2 | 0.851 |
| Inverse Variance HHH | 0.85 |
| Total Energy LHL | 0.85 |
| Size Zone Non Uniformity | 0.85 |
| Sphericity | 0.847 |
| Size Zone Non Uniformity LLH | 0.847 |
| Run Length Non Uniformity Normalized HHL | 0.844 |
| Gray Level Non Uniformity Normalized HHH (GLSZM) | 0.843 |
| Dependence Non Uniformity Normalized HHL | 0.843 |
| Zone Percentage HHL | 0.839 |
| Small Dependence Emphasis HHL | 0.838 |
| Size Zone Non Uniformity Normalized HHL | 0.835 |
| Small Area Emphasis HHL | 0.835 |
| Correlation | 0.831 |
| Dependence Non Uniformity LHH | 0.829 |
| Total Energy LHH | 0.826 |
| Short Run Emphasis HHH | 0.825 |
| Run Length Non Uniformity Normalized HHH | 0.825 |
| Dependence Non Uniformity LHL | 0.824 |
| Inverse Difference LHH | 0.823 |
| Inverse Difference Moment LHH | 0.823 |
| Small Dependence Emphasis HHH | 0.822 |
| Dependence Variance HLH | 0.821 |
| Run Percentage HHH | 0.821 |
| Zone Percentage HHH | 0.82 |
| Inverse Difference LHL | 0.818 |
| Dependence Non Uniformity HLH | 0.818 |
| Inverse Variance LHH | 0.817 |
| Large Dependence Emphasis HLH | 0.817 |
| Run Length Non Uniformity Normalized HLH | 0.817 |
| Short Run Emphasis HLH | 0.817 |
| Dependence Non Uniformity Normalized HLH | 0.817 |
| Difference Variance | 0.816 |
| Long Run Emphasis HLH | 0.815 |
| Energy LHL | 0.815 |
| Contrast (GLCM) | 0.815 |
| Run Percentage HLH | 0.815 |
| Joint Entropy LHH | 0.814 |
| Difference Entropy | 0.813 |
| Small Dependence Emphasis HLH | 0.813 |
| Size Zone Non Uniformity Normalized HLH | 0.813 |
| Small Area Emphasis HLH | 0.813 |
| Difference Entropy LHH | 0.812 |
| Difference Average | 0.812 |
| Run Variance HLH | 0.811 |
| Inverse Difference Moment | 0.81 |
| Inverse Difference | 0.81 |
| Inverse Variance | 0.809 |
| Run Entropy LHH | 0.809 |
| Entropy LHH | 0.808 |
| Zone Percentage HLH | 0.808 |
| Sum Entropy LHH | 0.806 |
| Inverse Difference Moment Normalized | 0.805 |
| Inverse Difference Normalized | 0.804 |
| Small Dependence Low Gray Level Emphasis | 0.804 |
| Energy LHH | 0.8 |
| Joint Entropy LHL | 0.798 |
| Small Area Low Gray Level Emphasis | 0.796 |
| Strength | 0.795 |
| Dependence Non Uniformity LLH | 0.795 |
| Run Length Non Uniformity HHL | 0.793 |
| Gray Level Non Uniformity Normalized LHL (GLDM) | 0.79 |
| Busyness | 0.79 |
| Dependence Non Uniformity Normalized LHH | 0.789 |
| Small Dependence Emphasis LHH | 0.788 |
| Coarseness | 0.787 |

TABLE 3-continued

Groups of radiomic features collinear
with radiomic features of Table 2

| Radiomic features | \|rho\| with original feature |
|---|---|
| Zone Percentage LHH | 0.786 |
| Dependence Non Uniformity Normalized LHL | 0.786 |
| Run Length Non Uniformity HLH | 0.786 |
| Small Dependence Emphasis LHL | 0.783 |
| Joint Entropy | 0.783 |
| Small Area Emphasis LHL | 0.782 |
| Size Zone Non Uniformity Normalized LHL | 0.782 |
| Short Run Emphasis HLL | 0.781 |
| Run Length Non Uniformity LHH | 0.78 |
| Run Length Non Uniformity Normalized HLL | 0.78 |
| Large Dependence Emphasis HLL | 0.779 |
| Long Run Emphasis HLL | 0.779 |
| Run Percentage HLL | 0.779 |
| Dependence Variance HLL | 0.778 |
| Dependence Non Uniformity HLL | 0.776 |
| Zone Percentage HLL | 0.776 |
| Dependence Non Uniformity | 0.771 |
| Dependence Non Uniformity HHH | 0.771 |
| Dependence Non Uniformity Normalized LLH | 0.752 |
| Low Gray Level Zone Emphasis | 0.752 |
| Short Run Low Gray Level Emphasis | 0.751 |
| Group 3 (cluster A) | |
| Dependence Entropy | 1.000 |
| Zone Entropy | 0.94 |
| Correlation | 0.892 |
| Informational Measure of Correlation 2 | 0.874 |
| Zone Percentage HHH | 0.848 |
| Small Dependence Emphasis HHH | 0.848 |
| Run Percentage HHH | 0.848 |
| Dependence Non Uniformity Normalized LHL | 0.847 |
| Small Dependence Emphasis LHL | 0.847 |
| Zone Percentage HHL | 0.847 |
| Small Dependence High Gray Level Emphasis | 0.846 |
| Small Dependence Emphasis HHL | 0.846 |
| Dependence Non Uniformity Normalized HHL | 0.846 |
| Short Run Emphasis HHH | 0.845 |
| Run Length Non Uniformity Normalized HHH | 0.845 |
| Run Length Non Uniformity Normalized HHL | 0.845 |
| Size Zone Non Uniformity Normalized LHL | 0.844 |
| Small Area Emphasis LHL | 0.844 |
| Size Zone Non Uniformity Normalized HHL | 0.842 |
| Small Area Emphasis HHL | 0.842 |
| Zone Percentage HLH | 0.84 |
| Run Variance HLH | 0.84 |
| Small Dependence Emphasis HLH | 0.839 |
| Long Run Emphasis HLH | 0.839 |
| Size Zone Non Uniformity Normalized LLH | 0.838 |
| Small Area Emphasis LLH | 0.838 |
| Size Zone Non Uniformity Normalized HLH | 0.838 |
| Small Area Emphasis HLH | 0.837 |
| Run Percentage HLH | 0.837 |
| Run Length Non Uniformity Normalized HLH | 0.836 |
| Short Run Emphasis HLH | 0.836 |
| Large Dependence Emphasis HLH | 0.836 |
| Zone Percentage LHH | 0.834 |
| Small Dependence Emphasis LLH | 0.833 |
| Small Dependence Emphasis LHH | 0.833 |
| Dependence Non Uniformity Normalized HLH | 0.833 |
| Zone Percentage LLH | 0.832 |
| Dependence Variance HLH | 0.831 |
| Dependence Non Uniformity Normalized LLH | 0.829 |
| Dependence Non Uniformity Normalized LHH | 0.826 |
| Inverse Difference LHL | 0.825 |
| Inverse Difference Moment HHH | 0.819 |
| Inverse Difference HHH | 0.819 |
| Uniformity HHH | 0.818 |
| Gray Level Non Uniformity Normalized LHL (GLSZM) | 0.817 |
| Gray Level Non Uniformity Normalized HHH (GLDM) | 0.813 |
| Gray Level Non Uniformity Normalized HHL (GLDM) | 0.813 |
| Joint Entropy LHL | 0.812 |
| Inverse Difference Normalized | 0.811 |
| Inverse Difference Moment Normalized | 0.811 |
| Long Run Emphasis HLL | 0.81 |

TABLE 3-continued

Groups of radiomic features collinear
with radiomic features of Table 2

| Radiomic features | \|rho\| with original feature |
|---|---|
| Zone Percentage HLL | 0.809 |
| Inverse Difference | 0.809 |
| Inverse Difference Moment | 0.809 |
| Difference Average | 0.808 |
| Run Percentage HLL | 0.808 |
| Large Dependence Emphasis HLL | 0.808 |
| Contrast (GLCM) | 0.807 |
| Short Run Emphasis HLL | 0.807 |
| Run Length Non Uniformity Normalized HLL | 0.807 |
| Inverse Variance | 0.807 |
| Inverse Variance HHL | 0.807 |
| Difference Entropy | 0.806 |
| Dependence Variance HLL | 0.804 |
| Inverse Difference Moment LHH | 0.803 |
| Difference Variance | 0.802 |
| Entropy LHH | 0.802 |
| Inverse Variance LHH | 0.802 |
| Inverse Difference LHH | 0.802 |
| Inverse Variance HHH | 0.801 |
| Sum Entropy LHH | 0.799 |
| Joint Entropy LHH | 0.799 |
| Gray Level Non Uniformity Normalized HHH (GLSZM) | 0.798 |
| Gray Level Non Uniformity Normalized HHL (GLSZM) | 0.798 |
| Difference Entropy LHH | 0.795 |
| Run Entropy LHH | 0.761 |
| Group 4 (cluster B) | |
| Mean LLL | 1.000 |
| Median LLL | 0.853 |
| Energy LLL | 0.843 |
| Group 5 (cluster C) | |
| Run Entropy | 1.000 |

The groups identified in Table 3 may be reduced to include only those radiomic features that are correlated with the original feature of that group (i.e. one of the five original features identified by the feature selection algorithm) to a degree of at least |rho|=0.800 (this includes the original feature itself which is, by definition, correlated with itself to a degree of rho=1). For example, the groups may be reduced to those features that are correlated with the original feature of that group to a degree of at least |rho|=0.850. For example, the groups may be reduced to those features that are correlated with the original feature of that group to a degree of at least |rho|=0.900. For example, the groups may be reduced to those features that are correlated with the original feature of that group to a degree of at least |rho|=0.950.

In addition to the radiomic signature being calculated on the basis of the at least two radiomic features from different clusters or groups, it may also be calculated on the basis of additional radiomic features. For example, the radiomic signature may include more than one radiomic feature from any given cluster or group, or may include radiomic features not included in any of the clusters or groups. Thus, it may be said that the radiomic signature is calculated on the basis of a plurality of radiomic features, and the plurality of radiomic features may comprise the at least two radiomic features referred to above.

Each of the radiomic signatures of the invention provides a straightforward means for characterising a ROI using medical imaging data and for identifying AT dysfunction. Because each of the radiomic signatures of the invention is based on a relatively small number of the total overall number of possible radiomic features that can be measured, the signature is simple to calculate and understand, and its physiological significance can be better appreciated by the clinician.

System

The methods of the invention may be performed on a system, such as a computer system. The invention therefore also provides a system that is configured or arranged to perform one or more of the methods of the invention. For example, the system may comprise a computer processor configured to perform one or more of the methods, or steps of the methods, of the invention. The system may also comprise a computer-readable memory loaded with executable instructions for performing the steps of any of the methods of the invention.

In particular, the methods of deriving the radiomic signature may be performed on such a system and such systems are therefore provided in accordance with the invention. For example, the system may be configured to receive, and optionally store, a dataset comprising the values of a plurality of radiomic features of a ROI obtained from medical imaging data for each of a plurality of individuals. The system may be configured to use such a dataset to construct (e.g. derive and validate) a radiomic signature according to the methods of the invention.

Alternatively, the system may be configured to perform the method of characterising a ROI or identifying AT dysfunction. In particular, the invention provides a system for characterising a ROI using medical imaging data of a subject. The system may be configured to calculate the value of a radiomic signature of a ROI using the medical imaging data. The radiomic signature may be calculated on the basis of measured values of at least two radiomic features of the ROI, and the measured values of the at least two radiomic features may be calculated from the medical imaging data.

The system may also be configured to calculate the radiomic features from medical imaging data, as described in more detail above. The system may therefore be configured to receive, and optionally store, medical imaging data, and to process the imaging data to calculate the radiomic features.

Definition of Radiomic Features

The definitions of the radiomic features referred to herein are generally well understood within the field of radiomics by reference to their name only. However, for ease or reference definitions of the features used herein are provided in Tables R1 to R7 below. The radiomic features in Tables R1 to R7 are defined in accordance with the radiomic features used by the Pyradiomics package (http://pyradiomics.readthedocs.io/en/latest/features.html, see van Griethuysen, J. J. M., Fedorov, A., Parmar, C., Hosny, A., Aucoin, N., Narayan, V., Beets-Tan, R. G. H., Fillon-Robin, J. C., Pieper, S., Aerts, H. J. W. L. (2017). Computational Radiomics System to Decode the Radiographic Phenotype. Cancer Research, 77(21), e104-e107. https://doi.org/10.1158/0008-5472.CAN-17-0339). Most features defined in Tables R1 to R7 are in compliance with feature definitions as described by the Imaging Biomarker Standardization Initiative (IBSI), which are available in Zwanenburg et al. (2016) (Zwanenburg, A., Leger, S., Vallieres, M., and Löck, S. (2016). Image biomarker standardisation initiative—feature definitions. In eprint arXiv:1612.07003 [cs.CV]). Where a definition provided below does not comply exactly from the IBSI definition, it should be understood that either definition could be used in accordance with the invention. Ultimately, the precise mathematical definition of the radiomic features is not crucial because slight modifications do not affect the general properties of the image that are measured by each of the features. Thus, slight modifications to the features (for example, the addition or subtraction of constants or scaling) and alternative definitions of the features are intended to be encompassed by the present invention.

a. First Order Statistics

These statistics describe the central tendency, variability, uniformity, asymmetry, skewness and magnitude of the attenuation values in a given region of interest (ROI), disregarding the spatial relationship of the individual voxels. As such, they describe quantitative and qualitative features of the whole ROI. A total of 19 features were calculated for each one of the eight wavelet transformations and the original CT image, as follows:

Let:

X be the attenuation or radiodensity values (e.g. in HU) of a set of $N_p$ voxels included in the region of interest (ROI)

P(i) be the first order histogram with $N_g$ discrete intensity levels, where $N_g$ is the number of non-zero bins, equally spaced from 0 with a width.

p(i) be the normalized first order histogram and equal to $$\frac{P(i)}{N_p}$$

c is a value that shifts the intensities to prevent negative values in X. This ensures that voxels with the lowest gray values contribute the least to Energy, instead of voxels with gray level intensity closest to 0. Since the HU range of adipose tissue (AT) within the ROI (−190 to −30 HU) does not include zero, c may be set at c=0. Therefore, higher energy corresponds to less radiodense AT, and therefore a higher lipophilic content.

$\epsilon$ is an arbitrarily small positive number (e.g. $\approx 2.2 \times 10^{-16}$)

TABLE R1

First-order radiomic features for ROI characterization

| Radiomic feature | Interpretation |
|---|---|
| $\text{Energy} = \sum_{i=1}^{N_p} (X(i) + c)^2$ | Energy is a measure of the magnitude of voxel values in an image. A larger value implies a greater sum of the squares of these values. |
| $\text{Total Energy} = V_{voxel} \sum_{i=1}^{N_p} (X(i) + c)^2$ | Total Energy is the value of Energy feature scaled by the volume of the voxel in cubic mm. |

TABLE R1-continued

First-order radiomic features for ROI characterization

| Radiomic feature | Interpretation |
| --- | --- |
| $\text{Entropy} = -\sum_{i=1}^{N_g} p(i)\log_2(p(i) + \epsilon)$ | Entropy specifies the uncertainty/randomness in the image values. It measures the average amount of information required to encode the image values |
| Minimum = min(X) | The minimum gray level intensity within the ROI. |
| The 10th percentile of X | The 10th percentile of X |
| The 90th percentile of X | The 90th percentile of X |
| Maximum = max(X) | The maximum gray level intensity within the ROI. |
| $\text{Mean} = \frac{1}{N_p}\sum_{i=1}^{N_p} X(i)$ | The average (mean) gray level intensity within the ROI. |
| Median | The median gray level intensity within the ROI. |
| Interquartile range = $P_{75}$-$P_{25}$ | Here $P_{25}$ and $P_{75}$ are the $25^{th}$ and $75^{th}$ percentile of the image array, respectively. |
| Range = max(X) - min(X) | The range of gray values in the ROI. |
| $MAD = \frac{1}{N_p}\sum_{i=1}^{N_p} [X(i) - \overline{X}]$ | Mean Absolute Deviation (MAD) is the mean distance of all intensity values from the Mean Value of the image array. |
| $rMAD = \frac{1}{N_{10-90}} \sum_{i=1}^{N_{10-90}} [X_{10-90}(i) - \overline{X}_{10-90}]$ | Robust Mean Absolute Deviation (rMAD) is the mean distance of all intensity values from the Mean Value calculated on the subset of image array with gray levels in between, or equal to the $10^{th}$ and $90^{th}$ percentile. |
| $RMS = \sqrt{\frac{1}{N_p}\sum_{i=1}^{N_p} (X(i) + c)^2}$ | Root Mean Squared (RMS) is the square-root of the mean of all the squared intensity values. It is another measure of the magnitude of the image values. This feature is volume-confounded, a larger value of c increases the effect of volume-confounding. |
| $\text{Skewness} = \frac{\mu_3}{\sigma^3} = \dfrac{\frac{1}{N_p}\sum_{i=1}^{N_p}(X(i) - \overline{X})^3}{\left(\sqrt{\frac{1}{N_p}\sum_{i=1}^{N_p}(X(i) - \overline{X})^2}\right)^3}$ | Skewness measures the asymmetry of the distribution of values about the Mean value. Depending on where the tail is elongated and the mass of the distribution is concentrated, this value can be positive or negative. (Where $\mu_3$ is the 3rd central moment). |
| $\text{Kurtosis} = \frac{\mu_4}{\sigma^4} = \dfrac{\frac{1}{N_p}\sum_{i=1}^{N_p}(X(i) - \overline{X})^4}{\left(\sqrt{\frac{1}{N_p}\sum_{i=1}^{N_p}(X(i) - \overline{X})^2}\right)^2}$ | Kurtosis is a measure of the 'peakedness' of the distribution of values in the image ROI. A higher kurtosis implies that the mass of the distribution is concentrated towards the tail(s) rather than towards the mean. A lower kurtosis implies the reverse: the mass of the distribution is concentrated towards a spike near the Mean value. (Where $\mu_4$ is the 4th central moment). |
| $\text{Variance} = \frac{1}{N_p}\sum_{i=1}^{N_p}(X(i) - \overline{X})^2$ | Variance is the mean of the squared distances of each intensity value from the Mean value. This is a measure of the spread of the distribution about the mean. |
| $\text{Uniformity} = \sum_{i=1}^{N_g} p(i)^2$ | Uniformity is a measure of the sum of the squares of each intensity value. This is a measure of the heterogeneity of the image array, where a greater uniformity implies a greater heterogeneity or a greater range of discrete intensity values. | b. Shape-Related Statistics

Shape-related statistics describe the size and shape of a given ROI, without taking into account the attenuation values of its voxels. Since they are independent of the gray level intensities, shape-related statistics were consistent across all wavelet transformation and the original CT image, and therefore were only calculated once. These were defined as follows:

Let:
V be the volume of the ROI in mm$^3$
A be the surface area of the ROI in mm$^2$

TABLE R2

Shape-related radiomic features for ROI characterization

| Radiomic feature | Interpretation |
|---|---|
| $\text{Volume} = \sum_{i=1}^{N} V_i$ | The volume of the ROI V is approximated by multiplying the number of voxels in the ROI by the volume of a single voxel $V_i$. |
| $\text{Surface Area} = \sum_{i=1}^{N} \frac{1}{2}[a_i b_i \times a_i c_i]$ | Surface Area is an approximation of the surface of the ROI in mm$^2$, calculated using a marching cubes algorithm, where N is the number of triangles forming the surface mesh of the volume (ROI), $a_i b_i$ and $a_i c_i$ are the edges of the $i^{th}$ triangle formed by points $a_i$, $b_i$ and $c_i$. |
| Surface to volume ratio = $\frac{A}{V}$ | Here, a lower value indicates a more compact (sphere-like) shape. This feature is not dimensionless, and is therefore (partly) dependent on the volume of the ROI. |
| Sphericity = $\frac{\sqrt[3]{36\pi V^2}}{A}$ | Sphericity is a measure of the roundness of the shape of the tumor region relative to a sphere. It is a dimensionless measure, independent of scale and orientation. The value range is 0 < sphericity ≤ 1, where a value of 1 indicates a perfect sphere (a sphere has the smallest possible surface area for a given volume, compared to other solids). |
| Volume Number | Total number of discrete volumes in the ROI. |
| Voxel Number | Total number of discrete voxels in the ROI. |
| Maximum 3D diameter | Maximum 3D diameter is defined as the largest pairwise Euclidean distance between surface voxels in the ROI (Feret Diameter). |
| Maximum 2D diameter (Slice) | Maximum 2D diameter (Slice) is defined as the largest pairwise Euclidean distance between ROI surface voxels in the row-column (generally the axial) plane. |
| Maximum 2D diameter (Column) | Maximum 2D diameter (Column) is defined as the largest pairwise Euclidean distance between ROI surface voxels in the row-slice (usually the coronal) plane. |
| Maximum 2D diameter (Row) | Maximum 2D diameter (Row) is defined as the largest pairwise Euclidean distance between tumor surface voxels in the column-slice (usually the sagittal) plane. |
| Major axis = $4\sqrt{\lambda_{major}}$ | $\lambda_{major}$ is the length of the largest principal component axis |

TABLE R2-continued

Shape-related radiomic features for ROI characterization

| Radiomic feature | Interpretation |
|---|---|
| Minor axis = $4\sqrt{\lambda_{minor}}$ | $\lambda_{minor}$ is the length of the second largest principal component axis |
| Least axis = $4\sqrt{\lambda_{least}}$ | $\lambda_{least}$ is the length of the smallest principal component axis |
| Elongation = $\sqrt{\frac{\lambda_{minor}}{\lambda_{major}}}$ | Here, $\lambda_{major}$ and $\lambda_{minor}$ are the lengths of the largest and second largest principal component axes. The values range between 1 (circle-like (non-elongated)) and 0 (single point or 1 dimensional line). |
| Flatness = $\sqrt{\frac{\lambda_{least}}{\lambda_{major}}}$ | Here, $\lambda_{major}$ and $\lambda_{minor}$ are the lengths of the largest and smallest principal component axes. The values range between 1 (non-flat, sphere-like) and 0 (a flat object). | c. Gray Level Co-Occurrence Matrix (GLCM)

In simple words, a GLCM describes the number of times a voxel of a given attenuation value i is located next to a voxel of J. A GLCM of size $N_g \times N_g$ describes the second-order joint probability function of an image region constrained by the mask and is defined as $P(i,j|\delta, \theta)$. The $(i,j)^{th}$ element of this matrix represents the number of times the combination of levels i and j occur in two pixels in the image, that are separated by a distance of δ pixels along angle θ. The distance δ from the center voxel is defined as the distance according to the infinity norm. For δ=1, this results in 2 neighbors for each of 13 angles in 3D (26-connectivity) and for δ=2 a 98-connectivity (49 unique angles). In order to get rotationally invariant results, statistics are calculated in all directions and then averaged, to ensure a symmetrical GLCM.

Let:
ε be an arbitrarily small positive number (e.g. ≈2.2×10$^{-16}$)
$P(i,j)$ be the co-occurrence matrix for an arbitrary δ and θ
$p(i,j)$ be the normalized co-occurrence matrix and equal to $$\frac{P(i,j)}{\sum P(i,j)}$$

$N_g$ be the number of discrete intensity levels in the image
$p_x(i) = \sum_{j=1}^{N_g} (P(i,j))$ be the marginal row probabilities
$p_y(i) = \sum_{i=1}^{N_g} (P(i,j))$ be the marginal column probabilities
$\mu_x$ be the mean gray level intensity of $p_x$ and defined as $\mu_x = \sum_{i=1}^{N_g} p_x(i)i$
$\mu_y$ be the mean gray level intensity of $p_y$ and defined as $\mu_y = \sum_{j=1}^{N_g} p_y(i)j$
$\sigma_x$ be the standard deviation of $p_x$
$\sigma_y$ be the standard deviation of $p_y$ $$p_{x+y}(k) = \sum_{i=1}^{N_g}\sum_{j=1}^{N_g} p(i,j), \text{ where } i+j=k, \text{ and } k = 2, 3, \ldots, 2N_g$$

For distance weighting, GLCM matrices are weighted by weighting factor W and then summed and normalised. Weighting factor W is calculated for the distance between neighbouring voxels by $W = e^{-\|d\|^2}$, where d is the distance for the associated angle.

TABLE R3

Gray Level Co-occurrence Matrix (GLCM) statistics for ROI characterization

| Radiomic feature | Interpretation |
|---|---|
| $\text{Autocorrelation} = \sum_{i=1}^{N_g} \sum_{j=1}^{N_g} p(i,j) ij$ | Autocorrelation is a measure of the magnitude of the fineness and coarseness of texture. |
| $\text{Joint average} = \mu_x = \sum_{i=1}^{N_g} \sum_{j=1}^{N_g} p(i,j) i$ | Returns the mean gray level intensity of the i distribution. |
| $\text{Cluster prominence} = \sum_{i=1}^{N_g} \sum_{j=1}^{N_g} (i + j - \mu_x - \mu_y)^4 p(i,j)$ | Cluster Prominence is a measure of the skewness and asymmetry of the GLCM. A higher value implies more asymmetry around the mean while a lower value indicates a peak near the mean value and less variation around the mean. |
| $\text{Cluster tendency} = \sum_{i=1}^{N_g} \sum_{j=1}^{N_g} (i + j - \mu_x - \mu_y)^2 p(i,j)$ | Cluster Tendency is a measure of groupings of voxels with similar gray level values. |
| $\text{Cluster shade} = \sum_{i=1}^{N_g} \sum_{j=1}^{N_g} (i + j - \mu_x - \mu_y)^3 p(i,j)$ | Cluster Shade is a measure of the skewness and uniformity of the GLCM. A higher cluster shade implies greater asymmetry about the mean. |
| $\text{Constrast} = \sum_{i=1}^{N_g} \sum_{j=1}^{N_g} (i - j)^2 p(i,j)$ | Contrast is a measure of the local intensity variation, favoring values away from the diagonal (i = j). A larger value correlates with a greater disparity in intensity values among neighboring voxels. |
| $\text{Correlation} = \dfrac{\sum_{i=1}^{N_g} \sum_{j=1}^{N_g} p(i,j) ij - \mu_x \mu_y}{\sigma_x(i)\sigma_y(j)}$ | Correlation is a value between 0 (uncorrelated) and 1 (perfectly correlated) showing the linear dependency of gray level values to their respective voxels in the GLCM. |
| $\text{Difference average} = \sum_{k=0}^{N_g-1} k p_{x-y}(k)$ | Difference Average measures the relationship between occurrences of pairs with similar intensity values and occurrences of pairs with differing intensity values |
| $\text{Difference entropy} = \sum_{k=0}^{N_g-1} p_{x-y}(k) \log_2 (p_{x-y}(k) + \epsilon)$ | Difference Entropy is a measure of the randomness/variability in neighborhood intensity value differences. |
| $\text{Difference variance} = \sum_{k=0}^{N_g-1} (k - DA)^2 p_{x-y}(k)$ | Difference Variance is a measure of heterogeneity that places higher weights on differing intensity level pairs that deviate more from the mean. |
| $\text{Joint energy} = \sum_{i=1}^{N_g} \sum_{j=1}^{N_g} (p(i,j))^2$ | Joint energy is a measure of homogeneous patterns in the image. A greater joint energy implies that there are more instances of intensity value pairs in the image that neighbor each other at higher frequencies. (also known as Angular Second Moment). |
| $\text{Joint entropy} = -\sum_{i=1}^{N_g} \sum_{j=1}^{N_g} p(i,j) \log_2(p(i,j) + \epsilon)$ | Joint entropy is a measure of the randomness/variability in neighborhood intensity values. |
| $IMC1 = \dfrac{HXY - HXY1}{\max\{HX, HY\}}$ $IMC\,2 = \sqrt{1 - e^{-2(HXY2 - HXY)}}$ | Informational measure of correlation 1 Informational measure of correlation 2 |
| $IDM = \sum_{i=1}^{N_g} \sum_{j=1}^{N_g} \dfrac{p(i,j)}{1 + |i - j|^2}$ | IDM (inverse difference moment a.k.a Homogeneity 2) is a measure of the local homogeneity of an image. IDM weights are the inverse of the Contrast weights (decreasing exponentially from the diagonal i = j in the GLCM). |
| $IDMN = \sum_{i=1}^{N_g} \sum_{j=1}^{N_g} \dfrac{p(i,j)}{1 + \left(\dfrac{|i - j|^2}{N_g^2}\right)}$ | IDMN (inverse difference moment normalized) is a measure of the local homogeneity of an image. IDMN weights are the inverse of the Contrast weights (decreasing exponentially from the diagonal i = j in the GLCM). Unlike Homogeneity 2, |

TABLE R3-continued

Gray Level Co-occurrence Matrix (GLCM) statistics for ROI characterization

| Radiomic feature | Interpretation |
|---|---|
| $ID = \sum_{i=1}^{N_g}\sum_{j=1}^{N_g} \frac{p(i,j)}{1+|i-j|}$ | IDMN normalizes the square of the difference between neighboring intensity values by dividing over the square of the total number of discrete intensity values. |
| | ID (inverse difference a.k.a. Homogeneity 1) is another measure of the local homogeneity of an image. With more uniform gray levels, the denominator will remain low, resulting in a higher overall value. |
| $IDN = \sum_{i=1}^{N_g}\sum_{j=1}^{N_g} \frac{p(i,j)}{1+\left(\frac{|i-j|}{N_g}\right)}$ | IDN (inverse difference normalized) is another measure of the local homogeneity of an image. Unlike Homogeneity 1, IDN normalizes the difference between the neighboring intensity values by dividing over the total number of discrete intensity values. |
| Inverse variance $= \sum_{i=1}^{N_g}\sum_{j=1}^{N_g} \frac{p(i,j)}{|i-j|^2}, i \neq j$ | |
| Maximum probability $= \max(p(i,j))$ | Maximum Probability is occurrences of the most predominant pair of neighboring intensity values (also known as Joint maximum). |
| Sum average $= \sum_{k=2}^{2N_g} p_{x+y}(k)k$ | Sum Average measures the relationship between occurrences of pairs with lower intensity values and occurrences of pairs with higher intensity values. |
| Sum entropy $= \sum_{k=2}^{2N_g} p_{x+y}(k)\log_2(p_{x+y}(k)+\epsilon)$ | Sum Entropy is a sum of neighborhood intensity value differences. |
| Sum squares $= \sum_{i=1}^{N_g}\sum_{j=1}^{N_g} (i-\mu_x)^2 p(i,j)$ | Sum of Squares or Variance is a measure in the distribution of neighboring intensity level pairs about the mean intensity level in the GLCM. (Defined by IBSI as Joint Variance). | d. Gray Level Size Zone Matrix (GLSZM)

A Gray Level Size Zone (GLSZM) describes gray level zones in a ROI, which are defined as the number of connected voxels that share the same gray level intensity. A voxel is considered connected if the distance is 1 according to the infinity norm (26-connected region in a 3D, 8-connected region in 2D). In a gray level size zone matrix P(i,j) the (i,j)$^{th}$ element equals the number of zones with gray level i and size j appear in image. Contrary to GLCM and GLRLM, the GLSZM is rotation independent, with only one matrix calculated for all directions in the ROI.

Let:

$N_g$ be the number of discreet intensity values in the image $N_s$ be the number of discreet zone sizes in the image $N_p$ be the number of voxels in the image $N_z$ be the number of zones in the ROI, which is equal to $\sum_{i=1}^{N_g}\sum_{j=1}^{N_z}P(i,j)$ and $1 \leq N_z \leq N_p$ P(i,j) be the size zone matrix p(i,j) be the normalized size zone matrix, defined as $$p(i,j) = \frac{P(i,j)}{N_g}$$

$\epsilon$ is an arbitrarily small positive number (e.g. $\approx 2.2 \times 10^{-16}$).

TABLE R4

Gray Level Size Zone Matrix (GLSZM) statistics for ROI characterization

| Radiomic feature | Interpretation |
|---|---|
| $SAE = \frac{\sum_{i=1}^{N_g}\sum_{j=1}^{N_z} \frac{p(i,j)}{j^2}}{N_z}$ | SAE (small area emphasis) is a measure of the distribution of small size zones, with a greater value indicative of smaller size zones and more fine textures. |
| $LAE = \frac{\sum_{i=1}^{N_g}\sum_{j=1}^{N_z} P(i,j)j^2}{N_z}$ | LAE (large area emphasis) is a measure of the distribution of large area size zones, with a greater value indicative of larger size zones and more coarse textures. |
| $GLN = \frac{\sum_{i=1}^{N_g}\left(\sum_{j=1}^{N_s} P(i,j)\right)^2}{N_z}$ | GLN (gray level non-uniformity) measures the variability of gray-level intensity values in the image, with a lower value indicating more homogeneity in intensity values. |
| $GLNN = \frac{\sum_{i=1}^{N_g}\left(\sum_{j=1}^{N_z} P(i,j)\right)^2}{N_z^2}$ | GLNN (gray level non-uniformity normalized) measures the variability of gray-level intensity values in the image, with a lower value indicating a greater similarity in intensity values. This is the normalized version of the GLN formula. |

TABLE R4-continued

Gray Level Size Zone Matrix (GLSZM) statistics for ROI characterization

| Radiomic feature | Interpretation |
|---|---|
| $SZN = \dfrac{\sum_{i=1}^{N_s}\left(\sum_{j=1}^{N_g} P(i,j)\right)^2}{N_z}$ | SZN (size zone non-uniformity) measures the variability of size zone volumes in the image, with a lower value indicating more homogeneity in size zone volumes. |
| $SZNN = \dfrac{\sum_{j=1}^{N_s}\left(\sum_{i=1}^{N_g} P(i,j)\right)^2}{N_z^2}$ | SZNN (size zone non-uniformity normalized) measures the variability of size zone volumes throughout the image, with a lower value indicating more homogeneity among zone size volumes in the image. This is the normalized version of the SZN formula. |
| Zone Percentage = $\dfrac{N_z}{N_p}$ | ZP (Zone Percentage) measures the coarseness of the texture by taking the ratio of number of zones and number of voxels in the ROI. Values are in range $\dfrac{1}{N_p} \le ZP \le 1$, with higher values indicating a larger portion of the ROI consists of small zones (indicates a more fine texture). |
| $GLV = \sum_{i-1}^{N_g}\sum_{j-1}^{N_s} p(i,j)(i-\mu)^2$, where $\mu = \sum_{i-1}^{N_g}\sum_{j-1}^{N_s} p(i,j)i$ | Gray level variance (GLV) measures the variance in gray level intensities for the zones. |
| $ZV = \sum_{i-1}^{N_g}\sum_{j-1}^{N_s} p(i,j)(j-\mu)^2$, where $\mu = \sum_{i-1}^{N_g}\sum_{j-1}^{N_s} p(i,j)j$ | Zone Variance (ZV) measures the variance in zone size volumes for the zones. |
| $ZE = -\sum_{i=1}^{N_g}\sum_{j=1}^{N_z} p(i,j)\log_2(p(i,j)+\epsilon)$ | Zone Entropy (ZE) measures the uncertainty/randomness in the distribution of zone sizes and gray levels. A higher value indicates more heterogeneity in the texture patterns. |
| $LGLZE = \dfrac{\sum_{i=1}^{N_g}\sum_{j=1}^{N_z}\dfrac{P(i,j)}{i^2}}{N_z}$ | LGLZE (low gray level zone emphasis) measures the distribution of lower gray-level size zones, with a higher value indicating a greater proportion of lower gray-level values and size zones in the image. |
| $HGLZE = \dfrac{\sum_{i=1}^{N_g}\sum_{j=1}^{N_z} P(i,j)i^2}{N_z}$ | HGLZE (high gray level zone emphasis) measures the distribution of the higher gray-level values, with a higher value indicating a greater proportion of higher gray-level values and size zones in the image. |
| $SALGLE = \dfrac{\sum_{i=1}^{N_g}\sum_{j=1}^{N_s}\dfrac{P(i,j)}{i^2 j^2}}{N_z}$ | SALGLE (small area low gray level emphasis) measures the proportion in the image of the joint distribution of smaller size zones with lower gray-level values. |
| $SAHGLE = \dfrac{\sum_{i=1}^{N_g}\sum_{j=1}^{N_z}\dfrac{P(i,j)i^2}{j^2}}{N_z}$ | SAHGLE (small area high gray level emphasis) measures the proportion in the image of the joint distribution of smaller size zones with higher gray-level values. |
| $LALGLE = \dfrac{\sum_{i=1}^{N_g}\sum_{j=1}^{N_s}\dfrac{P(i,j)j^2}{i^2}}{N_z}$ | LALGLE (low area low gray level emphasis) measures the proportion in the image of the joint distribution of larger size zones with lower gray-level values. |
| $LAHGLE = \dfrac{\sum_{i=1}^{N_g}\sum_{j=1}^{N_s} P(i,j)i^2 j^2}{N_z}$ | LAHGLE (low area high gray level emphasis) measures the proportion in the image of the joint distribution of larger size zones with higher gray-level values. | e. Gray Level Run Length Matrix (GLRLM)

A Gray Level Run Length Matrix (GLRLM) describes gray level runs, which are defined as the length in number of pixels, of consecutive pixels that have the same gray level value. In a gray level run length matrix $P(i,j|\theta)$, the $(i,j)^{th}$ element describes the number of runs with gray level i and length j occur in the image (ROI) along angle θ.

Let:

$N_g$ be the number of discreet intensity values in the image $N_r$ be the number of discreet run lengths in the image $N_p$ be the number of voxels in the image $N_z(\theta)$ be the number of runs in the image along angle θ, which is equal to $\sum_{i=1}^{N_g}\sum_{j=1}^{N_r} P(i,j|\theta)$ and $1 \le N_z(\theta) \le N_p$ $P(i,j|\theta)$ be the run length matrix for an arbitrary direction θ

$p(i,j|\theta)$ be the normalized run length matrix, defined as $$p(i,j|\theta) = \dfrac{P(i,j|\theta)}{N_z(\theta)}$$

$\epsilon$ is an arbitrarily small positive number (e.g. $\approx 2.2\times 10^{-16}$).

By default, the value of a feature is calculated on the GLRLM for each angle separately, after which the mean of these values is returned. If distance weighting is enabled, GLRLMs are weighted by the distance between neighbouring voxels and then summed and normalised. Features are then calculated on the resultant matrix. The distance between neighbouring voxels is calculated for each angle using the norm specified in 'weightingNorm'

TABLE R5

Gray Level Run Length Matrix (GLRLM) statistics for ROI characterization

| Radiomic feature | Interpretation |
|---|---|
| $SRE = \dfrac{\sum_{i=1}^{N_g}\sum_{j=1}^{N_r}\dfrac{P(i,j|\theta)}{j^2}}{N_z(\theta)}$ | SRE (Short Run Emphasis) is a measure of the distribution of short run lengths, with a greater value indicative of shorter run lengths and more fine textural textures. |
| $LRE = \dfrac{\sum_{i=1}^{N_g}\sum_{j=1}^{N_r} P(i,j|\theta)j^2}{N_z(\theta)}$ | LRE (Long Run Emphasis) is a measure of the distribution of long run lengths, with a greater value indicative of longer run lengths and more coarse structural textures. |

TABLE R5-continued

Gray Level Run Length Matrix (GLRLM) statistics for ROI characterization

| Radiomic feature | Interpretation |
|---|---|
| $GLN = \dfrac{\sum_{i=1}^{N_g}\left(\sum_{j=1}^{N_r} P(i,j\mid\theta)\right)^2}{N_z(\theta)}$ | GLN (Gray Level Non-uniformity) measures the similarity of gray-level intensity values in the image, where a lower GLN value correlates with a greater similarity in intensity values. |
| $GLNN = \dfrac{\sum_{i=1}^{N_g}\left(\sum_{j=1}^{N_r} P(i,j\mid\theta)\right)^2}{N_z(\theta)^2}$ | GLNN (Gray Level Non-uniformity Normalized) measures the similarity of gray-level intensity values in the image, where a lower GLNN value correlates with a greater similarity in intensity values. This is the normalized version of the GLN formula. |
| $RLN = \dfrac{\sum_{j=1}^{N_r}\left(\sum_{i=1}^{N_g} P(i,j\mid\theta)\right)^2}{N_z(\theta)}$ | RLN (Run Length Non-uniformity) measures the similarity of run lengths throughout the image, with a lower value indicating more homogeneity among run lengths in the image. |
| $RLNN = \dfrac{\sum_{j=1}^{N_r}\left(\sum_{i=1}^{N_g} P(i,j\mid\theta)\right)^2}{N_z(\theta)^2}$ | RLNN (Run Length Non-uniformity) measures the similarity of run lengths throughout the image, with a lower value indicating more homogeneity among run lengths in the image. This is the normalized version of the RLN formula. |
| $RP = \dfrac{N_z(\theta)}{N_p}$ | RP (Run Percentage) measures the coarseness of the texture by taking the ratio of number of runs and number of voxels in the ROI. Values are in range $\dfrac{1}{N_p} \leq RP \leq 1$, with higher values indicating a larger portion of the ROI consists of short runs (indicates a more fine texture). |
| $GLV = \sum_{i=1}^{N_g}\sum_{j=1}^{N_r} p(i,j\mid\theta)(i-\mu)^2$, where $\mu = \sum_{i=1}^{N_g}\sum_{j=1}^{N_r} p(i,j\mid\theta)i$ | GLV (Gray Level Variance) measures the variance in gray level intensity for the runs. |
| $RV = \sum_{i=1}^{N_g}\sum_{j=1}^{N_r} p(i,j\mid\theta)(j-\mu)^2$, where $\mu = \sum_{i=1}^{N_g}\sum_{j=1}^{N_r} p(i,j\mid\theta)j$ | RV (Run Variance) is a measure of the variance in runs for the run lengths. |
| $RE = -\sum_{i=1}^{N_g}\sum_{j=1}^{N_r} p(i,j\mid\theta)\log_2(p(i,j\mid\theta)+\epsilon)$ | RE (Run Entropy) measures the uncertainty/randomness in the distribution of run lengths and gray levels. A higher value indicates more heterogeneity in the texture patterns. |
| $LGLRE = \dfrac{\sum_{i=1}^{N_g}\sum_{j=1}^{N_r}\dfrac{P(i,j\mid\theta)}{i^2}}{N_z(\theta)}$ | LGLRE (low gray level run emphasis) measures the distribution of low gray-level values, with a higher value indicating a greater concentration of low gray-level values in the image. |
| $HGLRE = \dfrac{\sum_{i=1}^{N_g}\sum_{j=1}^{N_r} P(i,j\mid\theta)i^2}{N_z(\theta)}$ | HGLRE (high gray level run emphasis) measures the distribution of the higher gray-level values, with a higher value indicating a greater concentration of high gray-level values in the image. |
| $SRLGLE = \dfrac{\sum_{i=1}^{N_g}\sum_{j=1}^{N_r}\dfrac{P(i,j\mid\theta)}{i^2 j^2}}{N_z(\theta)}$ | SRLGLE (short run low gray level emphasis) measures the joint distribution of shorter run lengths with lower gray-level values. |
| $SRHGLE = \dfrac{\sum_{i=1}^{N_g}\sum_{j=1}^{N_r}\dfrac{P(i,j\mid\theta)i^2}{j^2}}{N_z(\theta)}$ | SRHGLE (short run high gray level emphasis) measures the joint distribution of shorter run lengths with higher gray-level values. |
| $LRLGLRE = \dfrac{\sum_{i=1}^{N_g}\sum_{j=1}^{N_r}\dfrac{P(i,j\mid\theta)j^2}{i^2}}{N_z(\theta)}$ | LRLGLRE (long run low gray level emphasis) measures the joint distribution of long run lengths with lower gray-level values. |
| $LRHGLRE = \dfrac{\sum_{i=1}^{N_g}\sum_{j=1}^{N_r} P(i,j\mid\theta)i^2 j^2}{N_z(\theta)}$ | LRHGLRE (long run high gray level run emphasis) measures the joint distribution of long run lengths with higher gray-level values. | f. Neighbouring Gray Tone Difference Matrix (NGTDM) Features

A Neighbouring Gray Tone Difference Matrix quantifies the difference between a gray value and the average gray value of its neighbours within distance δ. The sum of absolute differences for gray level i is stored in the matrix. Let $x_{gl}$ be a set of segmented voxels and $x_{gi}(j_x,j_y,j_z) \in x_{gl}$ be the gray level of a voxel at position $(j_x,j_y,j_z)$, then the average gray level of the neighbourhood is:

$$\overline{A_i} = \overline{A}(j_x, j_y, j_z) = \frac{1}{W}\sum_{k_x=-\delta}^{\delta}\sum_{k_y=-\delta}^{\delta}\sum_{k_z=-\delta}^{\delta} x_{gi}(j_x+k_x, j_y+k_y, j_z+k_z).$$

where $(k_x,k_y,k_z) \neq (0,0,0)$ and $x_{gi}(j_x+k_x,j_y+k_y, j_z+k_z) \in x_{gl}$ Here, W is the number of voxels in the neighbourhood that are also in $X_{gl}$.

Let:
$n_i$ be the number of voxels in $X_{gl}$ with gray level i
$N_{v,p}$ be the total number of voxels in $X_{gl}$ and equal to $\Sigma n_i$ (i.e. the number of voxels with a valid region; at least 1 neighbor). $N_{v,p} \leq N_p$, where $N_p$ is the total number of voxels in the ROI.
$p_i$ be the gray level probability and equal to $n_i/N_v$ $$s_i = \begin{cases} \sum_{i=1}^{n_i} |i - \overline{A}_i| & \text{for } n_i \neq 0 \\ 0 & \text{for } n_i = 0 \end{cases} \qquad 5$$

be the sum of absolute differences for gray level i
$N_g$ be the number of discreet gray levels
$N_{g,p}$ be the number of gray levels where $p_i \neq 0$

TABLE R6

Neigbouring Gray Tone Difference Matrix (NGTDM) for ROI characterization

| Radiomic feature | Interpretation |
| --- | --- |
| $\text{Coarseness} = \dfrac{1}{\sum_{i=1}^{N_g} p_i s_i}$ | Coarseness is a measure of average difference between the center voxel and its neighbourhood and is an indication of the spatial rate of change. A higher value indicates a lower spatial change rate and a locally more uniform texture. |
| $\text{Contrast} = \left( \dfrac{1}{N_{g,p}(N_{g,p}-1)} \sum_{i=1}^{N_g} \sum_{j=1}^{N_g} p_i p_j (i-j)^2 \right) \left( \dfrac{1}{N_{v,p}} \sum_{i=1}^{N_g} s_i \right),$ where $p_i \neq 0, p_j \neq 0$ | Contrast is a measure of the spatial intensity change, but is also dependent on the overall gray level dynamic range. Contrast is high when both the dynamic range and the spatial change rate are high, i.e. an image with a large range of gray levels, with large changes between voxels and their neighbourhood. |
| $\text{Busyness} = \dfrac{\sum_{i=1}^{N_g} p_i s_i}{\sum_{i=1}^{N_g} \sum_{j=1}^{N_g} |i p_i - j p_j|},$ where $p_i \neq 0, p_j \neq 0$ | A measure of the change from a pixel to its neighbour. A high value for busyness indicates a 'busy' image, with rapid changes of intensity between pixels and its neighbourhood. |
| $\text{Complexity} = \dfrac{1}{N_{v,p}} \sum_{i=1}^{N_g} \sum_{j=1}^{N_g} |i-j| \dfrac{p_i s_i + p_j s_j}{p_i + p_j},$ where $p_i \neq 0, p_j \neq 0$ | An image is considered complex when there are many primitive components in the image, i.e. the image is non-uniform and there are many rapid changes in gray level intensity. |

TABLE R6-continued

Neigbouring Gray Tone Difference Matrix (NGTDM) for ROI characterization

| Radiomic feature | Interpretation |
|---|---|
| $\text{Strength} = \dfrac{\sum_{i=1}^{N_g}\sum_{j=1}^{N_g}(p_i+p_j)(i-j)^2}{\sum_{i=1}^{N_g} s_i}$, where $p_i \neq 0, p_j \neq 0$ | Strength is a measure of the primitives in an image. Its value is high when the primitives are easily defined and visible, i.e. an image with slow change in intensity but more large coarse differences in gray level intensities. | e. Gray Level Dependence Matrix (GLDM)

A Gray Level Dependence Matrix (GLDM) quantifies gray level dependencies in an image. A gray level dependency is defined as the number of connected voxels within distance δ that are dependent on the center voxel. A neighbouring voxel with gray level j is considered dependent on center voxel with gray level i if $|i-j| \leq \alpha$. In a gray level dependence matrix P(i,j) the $(i,j)^{th}$ element describes the number of times a voxel with gray level i with j dependent voxels in its neighbourhood appears in image.

$N_g$ be the number of discreet intensity values in the image $N_d$ be the number of discreet dependency sizes in the image $N_z$ be the number of dependency zones in the image, which is equal to $\sum_{i=1}^{N_g} \sum_{j=1}^{N_d} P(i,j)$ P(i,j) be the dependence matrix p(i,j) be the normalized dependence matrix, defined as $$p(i,j) = \frac{P(i,j)}{N_z}$$

TABLE R7

Gray Level Dependence Matrix (GLDM) statistics for ROI characterization

| Radiomic feature | Interpretation |
|---|---|
| $SDE = \dfrac{\sum_{i=1}^{N_g}\sum_{j=1}^{N_d}\frac{P(i,j)}{i^2}}{N_z}$ | SDE (Small Dependence Emphasis): A measure of the distribution of small dependencies, with a greater value indicative of smaller dependence and less homogeneous textures. |
| $LDE = \dfrac{\sum_{i=1}^{N_g}\sum_{j=1}^{N_d} P(i,j)j^2}{N_z}$ | LDE (Large Dependence Emphasis): A measure of the distribution of large dependencies, with a greater value indicative of larger dependence and more homogeneous textures. |
| $GLN = \dfrac{\sum_{i=1}^{N_g}\left(\sum_{j=1}^{N_d} P(i,j)\right)^2}{\sum_{i=1}^{N_g}\sum_{j=1}^{N_d} P(i,j)}$ | (Gray Level Non Uniformity): Measures the similarity of gray-level intensity values in the image, where a lower GLN value correlates with a greater similarity in intensity values. |

TABLE R7-continued

Gray Level Dependence Matrix (GLDM) statistics for ROI characterization

| Radiomic feature | Interpretation |
|---|---|
| $DN = \dfrac{\sum_{j=1}^{N_d}\left(\sum_{i=1}^{N_g} P(i,j)\right)^2}{N_z}$ | DN (Dependence Non-Uniformity): Measures the similarity of dependence throughout the image, with a lower value indicating more homogeneity among dependencies in the image. |
| $DNN = \dfrac{\sum_{j=1}^{N_d}\left(\sum_{i=1}^{N_g} P(i,j)\right)^2}{N_z^2}$ | DNN (Dependence Non-Uniformity Normalized): Measures the similarity of dependence throughout the image, with a lower value indicating more homogeneity among dependencies in the image. This is the normalized version of the DLN formula. |
| $GLV = \sum_{i=1}^{N_g}\sum_{j=1}^{N_d} p(i,j)(i-\mu)^2$, where $\mu = \sum_{i=1}^{N_g}\sum_{j=1}^{N_d} ip(i,j)$ | GLV (Gray Level Variance): Measures the variance in grey level in the image. |
| $DV = \sum_{i=1}^{N_g}\sum_{j=1}^{N_d} p(i,j)(i-\mu)^2$, where $\mu = \sum_{i=1}^{N_g}\sum_{j=1}^{N_d} jp(i,j)$ | DV (Dependence Variance): Measures the variance in dependence size in the image. |
| $DE = -\sum_{i=1}^{N_g}\sum_{j=1}^{N_d} p(i,j)\log_2(p(i,j)+\epsilon)$ | DE (Dependence Entropy): Measures the entropy in dependence size in the image. |
| $LGLE = \dfrac{\sum_{i=1}^{N_g}\sum_{j=1}^{N_d}\frac{P(i,j)}{i^2}}{N_z}$ | LGLE (Low Gray Level Emphasis): Measures the distribution of low gray-level values, with a higher value indicating a greater concentration of low gray-level values in the image. |

TABLE R7-continued

Gray Level Dependence Matrix (GLDM) statistics for ROI characterization

| Radiomic feature | Interpretation |
|---|---|
| $HGLE = \dfrac{\sum_{i=1}^{N_g} \sum_{j=1}^{N_d} P(i,j) i^2}{N_z}$ | HGLE (High Gray Level Emphasis): Measures the distribution of the higher gray-level values, with a higher value indicating a greater concentration of high gray-level values in the image. |
| $SDLGLE = \dfrac{\sum_{i=1}^{N_g} \sum_{j=1}^{N_d} \dfrac{P(i,j)}{i^2 j^2}}{N_z}$ | SDLGLE (Small Dependence Low Gray Level Emphasis): Measures the joint distribution of small dependence with lower gray-level values. |
| $SDHGLE = \dfrac{\sum_{i=1}^{N_g} \sum_{j=1}^{N_d} \dfrac{P(i,j) i^2}{j^2}}{N_z}$ | SDHGLE (Small Dependence High Gray Level Emphasis): Measures the joint distribution of small dependence with higher gray-level values. |
| $LDLGLE = \dfrac{\sum_{i=1}^{N_g} \sum_{j=1}^{N_d} \dfrac{P(i,j) j^2}{i^2}}{N_z}$ | LDLGLE (Large Dependence Low Gray Level Emphasis): Measures the joint distribution of large dependence with lower gray-level values. |
| $LDHGLE = \dfrac{\sum_{i=1}^{N_g} \sum_{j=1}^{N_d} P(i,j) i^2 j^2}{N_z}$ | LDLGLE (Large Dependence High Gray Level Emphasis): Measures the joint distribution of large dependence with higher gray-level values. |

EXAMPLES

Methods
Study Design

Study Arm 1 consisted of 225 patients undergoing coronary artery bypass grafting surgery (CABG) from the Oxford Heart Vessels and Fat (OxHVF) cohort. Exclusion criteria were any inflammatory, infectious, liver/renal disease or malignancy. Patients receiving non-steroidal anti-inflammatory drugs were also excluded. All patients underwent a non-contrast enhanced CT scan, as described below, the aim being to explore whether non-invasive radiomic phenotyping of adipose tissue (AT) can offer information on AT biology and metabolic risk. In Group A (n=167) adipose tissue samples were harvested from subcutaneous fat (from the site of the chest incision) during surgery. Samples were snap-frozen for gene expression studies as described below.

Study Arm 2 consisted of 40 patients undergoing 18-fluorodeoxyglucose positron emission tomography/computed tomography (PET/CT) imaging for a clinical indication. This arm was used for the external validation of selected radiomic features as biomarkers of adipose tissue inflammation against the gold-standard imaging modality for quantification of tissue inflammation in vivo, i.e. $^{18F}$FDG PET/CT.

Gene Expression Studies

Samples of adipose (or adipocytes) and aortic tissue were snap frozen in QIAzol (Qiagen) and stored at −80° C. RNA was extracted using the RNeasy Micro or Mini kit (Qiagen) and ribonucleic acid was converted into complementary DNA (Quantitect Rev. Transcription kit—Qiagen). The cDNA was then subjected to quantitative polymerase chain reaction (qPCR) using TaqMan probes (Applied Biosystems) for FABP4 (Assay ID: Hs00609791_m1), PREF1 (Assay ID: Hs00171584_m1), TNFA (Assay ID Hs01113624_g1), IL6 (Assay ID Hs00985639_m1), Col1A1 (Assay ID Hs00164004_m1), and Sfrp5 (Assay ID Hs00169366_m1). Cyclophilin A (PPIA) was used as housekeeping gene (Assay ID Hs04194521_s1). The reactions were performed in triplicate in 384-well plates, using 5 ng of cDNA per reaction, on an ABI 7900HT Fast Real-Time PCR System (Applied Biosystems). The efficiency of the reaction in each plate was determined based on the slope of the standard curve; expression of each gene of interest relative to its housekeeping gene was calculated using the Pfaffl method.

Computerised Tomography Studies

Participants in Study Arms 1 and 2 underwent CT imaging using a 64-slice scanner (LightSpeed Ultra, General Electric). Heart rate was optimised using intravenous injection of beta-blockers and sublingual glyceryl-trinitrate (800 μg) was also administered to achieve maximum coronary vasodilatation. A non-contrast, prospectively ECG triggered axial acquisition CT scan was obtained (0.35 s rotation time, 2.5 mm axial slice thickness, 20 mm detector coverage, tube energy of 120 kV and 200 mA) with the carina and the diaphragm used as cranial and caudal landmarks respectively. The lung field of view was extended to cover the entire thoracic soft tissue (for adipose tissue analysis). For the analysis of adipose tissue radiomic features raw dicom images were transferred to a dedicated workstation and further post-processed by using 3D Slicer (see below).

Coronary Calcium Score

Coronary calcium score (CCS) was measured on Aquarius Workstation® for all coronary arteries (RCA quantified separately), by calculating the Agatston score.

Radiomic Feature Extraction of Adipose Tissue

Calculation of radiomic features in subcutaneous adipose tissue was performed in CT scans using the 3D Slicer software (v.4.9.0-2017-12-18 r26813, available at http://www.slicer.org; Fedorov, A. et al. 3D Slicer as an image computing platform for the Quantitative Imaging Network. Magn Reson Imaging 30, 1323-1341, doi:10.1016/j.mri.2012.05.001 (2012)). Segmentation of adipose tissue was performed by selecting an axial slice of 2.5 mm thickness at the level of the caudal edge of the sternum. All voxels located externally to the chest rib were tracked by manual contouring and by using a −190 to −30 Hounsfield Units (HU) mask for fat identification. The segmented adipose tissue was subsequently used to calculate and extract a series of radiomic features, using the SlicerRadiomics extension of 3D Slicer, which incorporates the Pyradiomics library into 3D Slicer (see van Griethuysen, J. J. M. et al. Computational Radiomics System to Decode the Radiographic Phenotype. Cancer Res 77, e104-e107, doi: 10.1158/0008-5472.CAN-17-0339 (2017)). Shape-related and first-order radiomic features were calculated using the raw HU values of the segmented adipose tissue. For calculation of texture features (GLCM, GLDM, GLRLM, GLSZM, and NGTDM), AT voxels were discretized into 16 bins of equal width (width of 10 HU), to reduce noise while allowing a sufficient resolution to detect biologically significant spatial changes in adipose tissue attenuation. To enforce symmetrical, rotationally-invariant results, texture statistics (GLCM etc.) were calculated in all four directions and then averaged.

Wavelet transformation: First order and texture-based statistics were also calculated for three-dimensional wavelet transformations of the original image resulting in eight additional sets of radiomic features.

Positron Emission Tomography/Computerised Tomography Imaging Studies

Selected radiomic features of adipose tissue were validated against $^{18F}$FDG uptake using PET/CT which is the gold standard modality to assess tissue inflammation in vivo. $^{18F}$FDG uptake in paired PET and CT images from 40 subjects (25 males/15 females) who had an $^{18F}$FDG PET/CT scan performed under a clinical indication. PET/CT examinations were performed on a 3D mode time of flight (ToF) GE Discovery 690 PET/CT system (GE Healthcare). The patients fasted for at least 6 hours prior to their scan. Their blood glucose was measured prior to intravenous injection, with 4 MBq/kg of $^{18F}$FDG. Imaging commenced 90 min post-injection (93±7 min) and covered the skull base to upper thighs. The PET/CT images were acquired under normal tidal respiration for 4 min per bed position. The CT was performed using a pitch of 0.984, 120 kV, auto mA with a noise index of 25. PET images were reconstructed using two different algorithms both of which used the CT for attenuation correction and the same normalisation correction factors. The standard of care PET reconstruction algorithm used is ToF OSEM (VPFX, GE Healthcare). This was used with two iterations, 24 subsets and 6.4 mm Gaussian filter. The sinograms generated at the time of scanning were retrospectively processed using the new ToF BPL reconstruction algorithm (Q.Clear, GE Healthcare). Acquired PET images were then analyzed using the Terarecon Aquarius iNtuition V.4.4.11 software. Circular regions of interest (ROI) were drawn at the midline anteriorly to the sternum to calculate mean SUV in subcutaneous adipose tissue. To calculate the target-to-background ratio (TBR), the mean SUV of adipose tissue was normalized against the mean SUV of the pulmonary artery lumen (at the level of PA bifurcation).

Statistical Analysis

Principal components analysis: In Arm 1, all 843 calculated AT radiomic features were included in principal component analysis to identify principal components (PC) that describe most of the phenotypic variation in the study population. A scree plot of PC against their eigenvalues was constructed. The three first components (PC1, PC2, PC3) were used to explore associations with demographic, biochemical and adipose tissue gene expression data in relevant correlation plots.

Feature selection and stability assessment: In order to limit the analysis to radiomic features that would be of most value as imaging biomarkers, a stability assessment of all 843 different radiomic features was performed. For this purpose 30 paired scans from the RIDER dataset (RIDER: The Reference Image Database to Evaluate Therapy Response; obtained online from https://wiki.cancerimagingarchive.net/display/Public/RIDER+Collections; jsessionid=C78203F71E49C7EA3A43E0D213CE5555) were used to assess the scan-rescan ICC of each radiomic feature. Then the ICC of all radiomic features for multiple delineation of the region of interest was also explored in 20 patients from the OxHVF cohort (delineated by two independent operators). Only those radiomic features with scan-rescan and multiple delineation intraclass correlation coefficient (ICC)≥0.90 were included in further analysis (n=196).

Unsupervised clustering of the study population by adipose tissue radiomic features: The 196 selected radiomic features of AT in Arm 1 were transformed to Z-scores for further analysis. Then all 196 radiomic features were used to perform hierarchical clustering of the observations in Arm 1 (using the Ward method and the squared Euclidean distance, hclust R package). The variation of each of the 196 different radiomic features across the n=225 observations of Arm 1 cohort was represented in a relevant heat map with a row dendrogram indicating the clustering of patients. Differences in the distribution of risk factors, biochemical or AT gene expression data between the two clusters of patients was then explored by use of chi-square or independent t-test as appropriate.

Feature selection and associations with AT biology: The relationships between the 196 stable radiomic features were visually inspected in a similarity-dissimilarity plot. Next a stepwise approach was applied and highly intercorrelated radiomic features (|rho|>0.9) were removed from further analysis by application of a known automated algorithm (see Kuhn, M. & Johnson, K. Applied predictive modeling. (Springer, 2013)). This function (function caret::findCorrelation, R package) searches through a correlation matrix and returns a vector of integers corresponding to columns to remove to reduce pair-wise correlations. The absolute values of pair-wise correlations are considered. If two variables have a high correlation, the function looks at the mean absolute correlation of each variable and removes the variable with the largest mean absolute correlation.

Particular radiomic features as imaging biomarkers to describe adipose tissue biology were then identified. The final 32 radiomic features (listed in Table 1) that survived the steps described above were included in logistic regression models to seek independent associations with the expression levels of target genes (TNFA, FABP4) in human AT that were used as surrogates for features of adipose tissue biology (inflammation, adipocyte differentiation, fibrosis, adipogenesis capacity and adipokine expression). Target genes' expression levels were split into groups (based on highest tertile) and used as categorical variables in multivariate logistic regression models. The final 31 radiomic features (1 feature was excluded from the models after testing for collinearity by Variance Inflation Factor) were fed into logistic regression models with the target gene of interest as the dependent variable. The baseline model was adjusted for classic risk factors (age, sex, diabetes, hypertension, smoking), HOMA-IR, body mass index and subcutaneous fat area (Model 1); Model 2 was further adjusted for radiomic features selected by backward selection (entry level: 0.05, removal level: 0.10). The discriminatory value of the nested models for identifying features of AT biology was compared by means of their respective C-statistics and the change in the area under the curve (A[AUC]).

Machine learning and internal cross-validation: Machine learning was used for the internal cross-validation of the filtered radiomic features and final feature selection. Machine learning with a random forest algorithm (rfecontrol, caret package R) with 5-fold cross-validation was used to select the top features able to classify dysfunctional adipose tissue (i.e., high adipose tissue inflammation plus low adipocyte differentiation, based on the median value of TNFA and FABP4 gene expression levels respectively). The top five radiomic features (Mean LLL, TotalEnergy HHL, Large Dependence Low Gray Level Emphasis, Dependence Entropy, and Run Entropy) identified from this algorithm validation process were used to calculate a composite radiomic signature (referred to as FatHealth) as a metric of adipose tissue health (FatHealth=$\Sigma$ $b_i$ $x_i$+c, where c is a constant, $x_i$ is the measured value of radiomic feature i, and $b_i$ the beta coefficient of feature i from a logistic regression model using the five radiomic features as independent predictors of adipose tissue health). Continuous variables between two groups were compared by Student's t-test, whereas categorical variables are compared using Pearson's Chi-square test. The analysis was performed using R v3.1.4 (packages: caret, hclust) and SPSS version 25.0. All tests were two-sided and a was set at 0.05, unless specified otherwise.

Results

Radiomic Feature Extraction and Principal Component Analysis

Figure 2B:
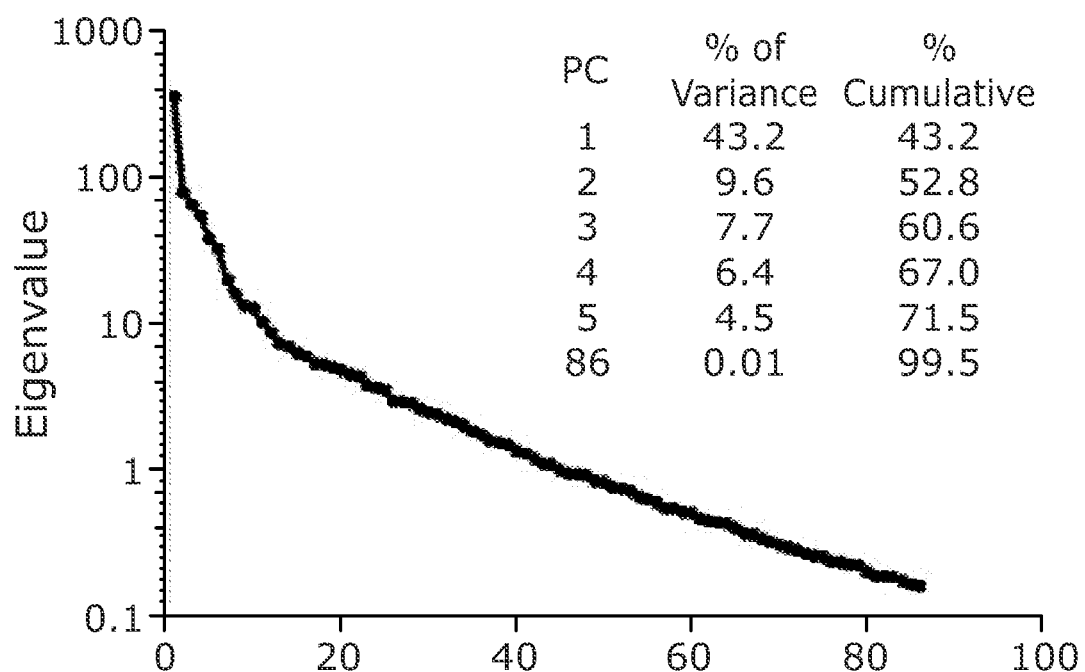
FIG. 2(b) is a component plot of the three major principal components.
Figure 2B:
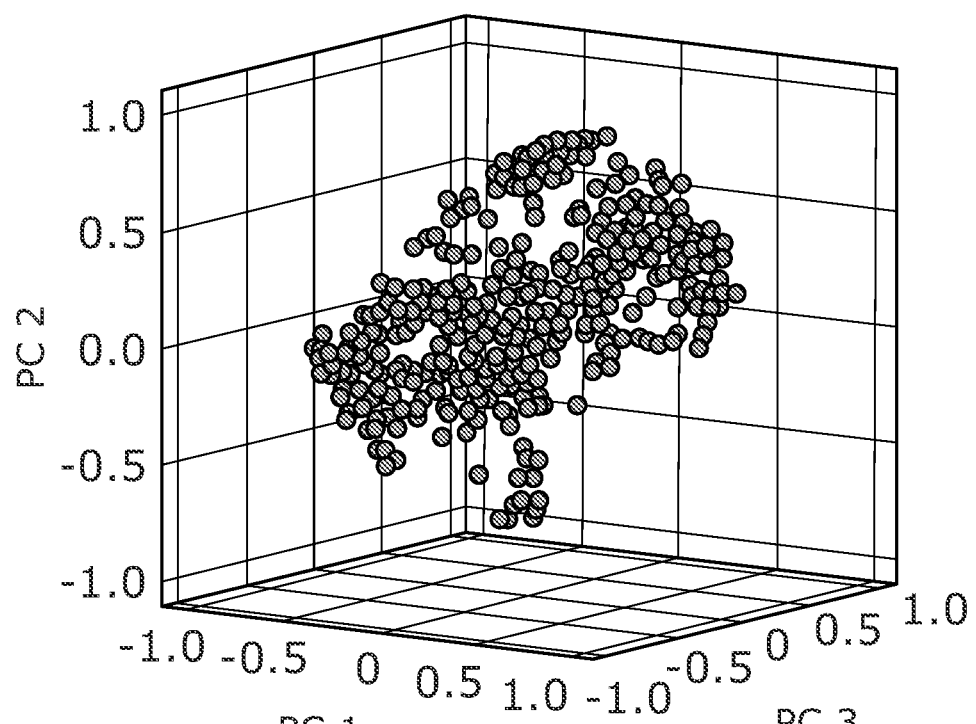
Figure 2C:
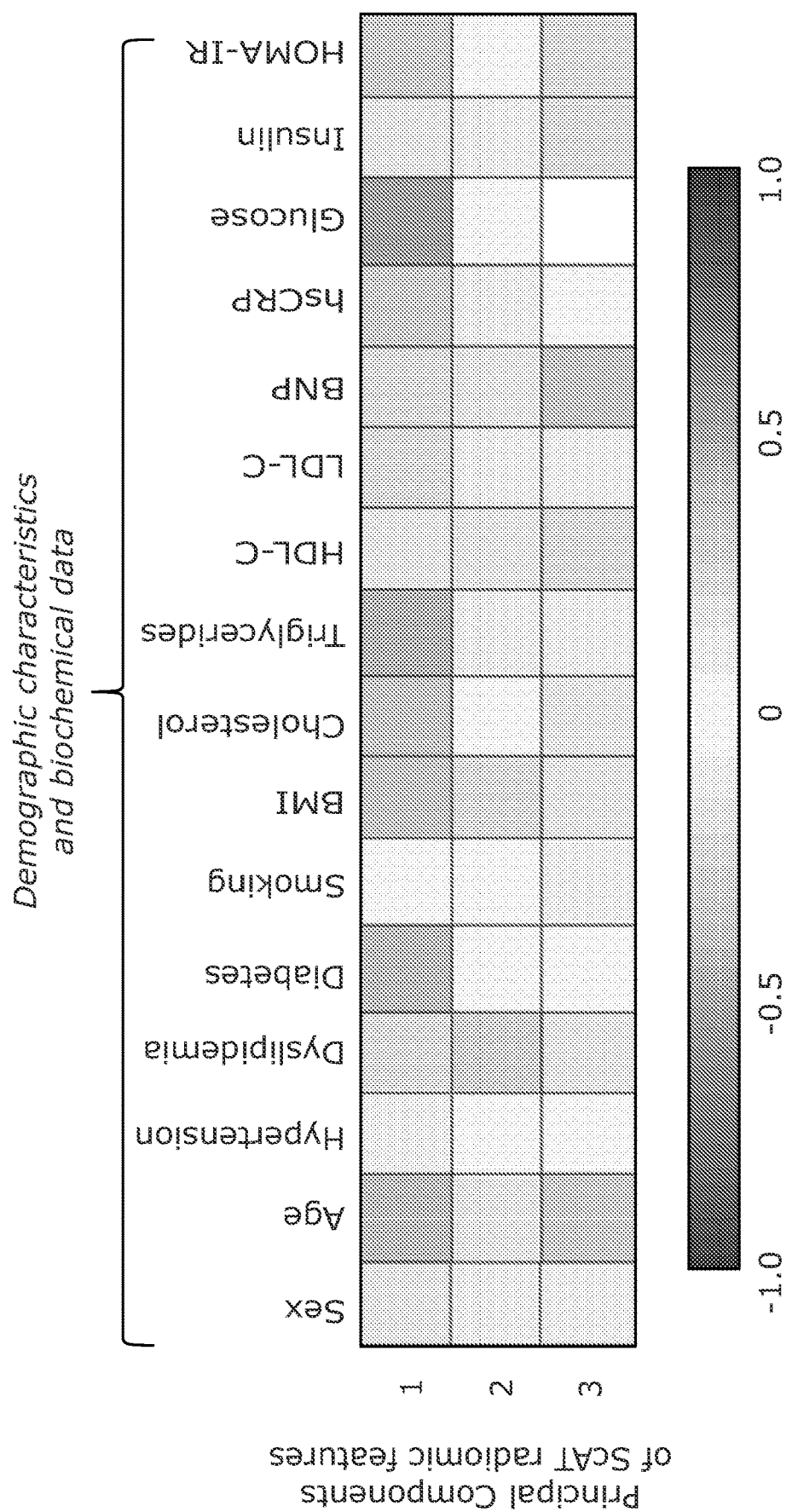
FIG. 2(c) is a correlation plot of the first three components with demographics, biochemical characteristics (n=225) and gene expression profile patterns (n=167) in adipose tissue from the patients of Arm 1.

The study design is summarized in FIG. 1. CT scans from 225 patients undergoing coronary artery bypass grafting were used to calculate a total of 843 radiomic features by segmentation of subcutaneous adipose tissue. These included 15 shape-related features, 18 first order statistics, 15 Gray Level Co-occurrence Matrix (GLCM), 18 Gray Level Dependence Matrix (GLDM), 16 Gray Level Run-Length Matrix (GLRLM), 16 Gray Level Size Zone Matrix (GLSZM), and 5 Neighbouring Gray Tone Difference Matrix (NGTDM) features, as defined in Tables R1 to R7, as well as eight wavelet transformations for each one of them. Initially an exploratory data analysis was performed by reducing the original radiomic dataset of possibly correlated features to its principal components. A total of 86 components accounted for the 99.5% of variation in the study population (scree plot, FIG. 2(a)), while the first 3 components explained 60.6% of the observed variation (FIG. 2(b)). The first 3 components were variably associated with clinical demographic, biochemical characteristics and gene expression patterns in the subcutaneous adipose tissue of Arm 1 patients (FIG. 2(c)), suggesting that standard non-contrast enhanced CT images of human fat contain rich extractable information associated with distinct biological phenotypes of adipose tissue and features of metabolic risk.

Unsupervised Clustering Based on the Radiomic Phenotyping of Adipose Tissue

Since principal components are inherent to the sample population studied and not of transferrable value as quantifiable biomarkers, an analysis of the radiomic features per se was performed. From the initial pool of 843 measured radiomic features, a stability assessment was performed and the intraclass correlation coefficients (ICC) for scan-rescan (RIDER dataset) and for multiple delineation (OxHVF cohort, FIG. 1) were calculated. Only those radiomic features with ICC≥0.90 (n=196) were included in further analyses. This set of 196 radiomic features was then used to perform unsupervised hierarchical clustering of the population in Arm 1 (FIG. 3a). Hierarchical clustering based on the radiomic features of adipose tissue identified two distinct clusters of patients, which significantly differed in the prevalence of metabolic risk factors and insulin resistance status (FIG. 3(a)). These findings demonstrate that the radiomic features of fat depots, for example a subcutaneous fat depot, should be useful for the non-invasive phenotyping of its biology, and for metabolic risk assessment.

Incremental Value of Radiomic Signatures for Detection of Adipose Tissue Dysfunction Having demonstrated the proof-of-concept that the radiomic features of adipose tissue are linked with its biology, next a radiomic signature that could be used as a biomarker of metabolic risk was identified. Construction of a similarity-dissimilarity plot (FIG. 3(b)) demonstrated that adipose tissue radiomic features are clustered in distinct groups of highly similar intra-cluster features. These 196 stable radiomic features were variably associated with homeostatic model assessment insulin resistance (HOMA-IR). In order to ensure a higher amount of information diversity in the final signature, an automated algorithm was applied that removed highly correlated features in stepwise manner. The final set of filtered 32 radiomic features (listed in Table 1), their inter-correlations and clusters are presented on a correlation matrix (FIG. 3(b)).

Figure 4B:
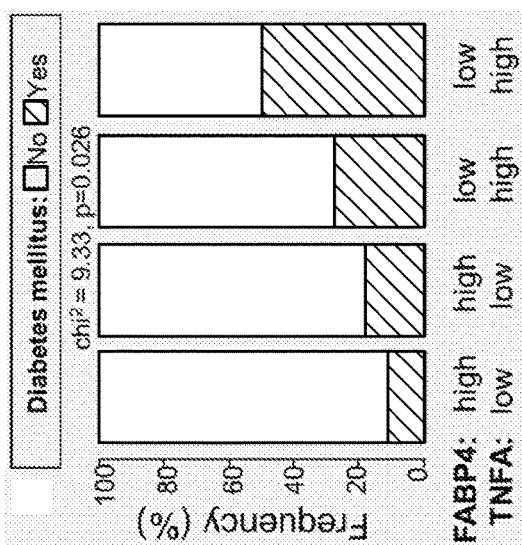
FIG. 4 illustrates the detection of adipose tissue dysfunction by radiomic phenotyping using a radiomic signature.
FIGS. 4(c) and (d) illustrate the sensitivity of multivariate logistic regression models for high FABP4 and TNFA expression in adipose tissue of the same patients, respectively, demonstrating the incremental discriminatory value of radiomic signatures for detecting adipocyte differentiation and adipose tissue inflammation status, respectively.
FIG. 4(e) illustrates aspects of the construction of a radiomic signature by machine learning using recursive feature elimination (RFE) with fivefold cross-validation and selection of the top radiomic features to detect adipose tissue dysfunction.
FIG. 4(f) demonstrates the incremental diagnostic value of the top radiomic features to detect adipose tissue dysfunction over clinical risk factors, obesity indices, and homeostasis model of insulin resistance (HOMA-IR).

Adipocyte differentiation status and inflammation of adipose are central features in adipose tissue dysfunction and insulin resistance development. First the association of gene expression profile of TNFA and FABP4 in subcutaneous adipose tissue with clinical phenotypes was explored. The patients were stratified based on the median levels of TNFA and FABP4 into four subgroups. The subgroup with low FABP4 and high TNFA expression had the higher prevalence of diabetes (FIG. 4a) as well as insulin resistance among non-diabetic patients (FIG. 4(b)). Therefore, it was next explored whether radiomic features of adipose tissue could be used to capture adipose tissue biology, namely its differentiation and inflammation status.

Figure 4C:
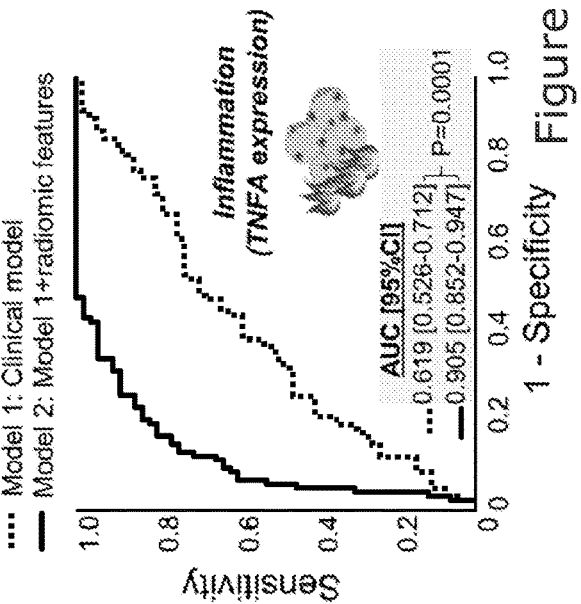
Figure 4D:
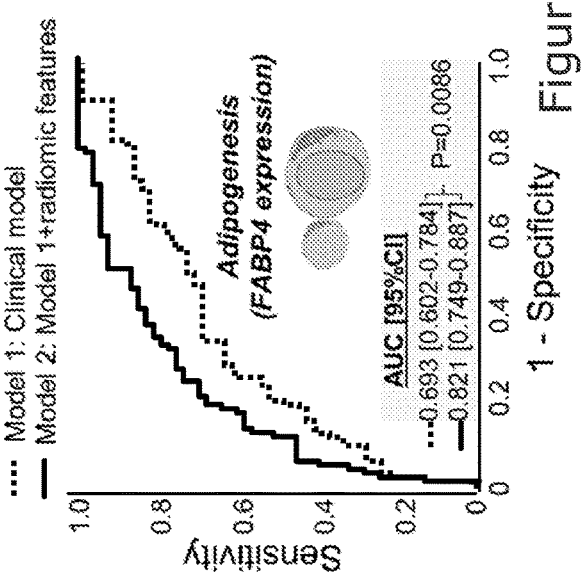

To this aim, radiomic features of subcutaneous adipose tissue were included by a backward selection process into multivariate logistic regression models by using as dependent variables the highest tertile of FABP4 and TNFA gene expression, respectively. Inclusion of radiomic features in multivariate models, significantly improved the discrimination of the baseline models for adipocyte differentiation (Δ[AUC]=0.121, p=0.0086, FIG. 4(c)) and adipose tissue inflammation (Δ[AUC]=0.287, p=0.0001, FIG. 4(d)) status beyond and above clinical risk factors, HOMA-IR or obesity measurements.

Figure 4F:
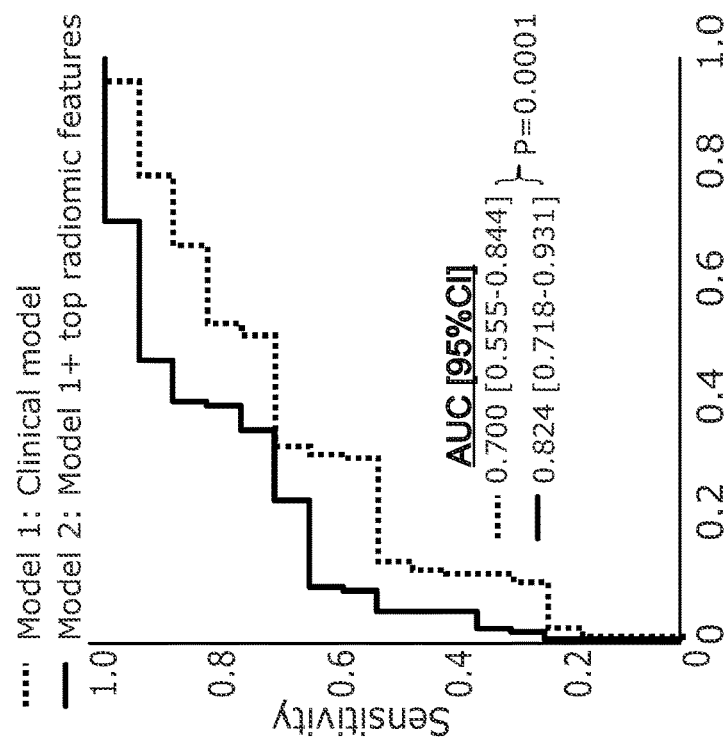
Figure 4E:
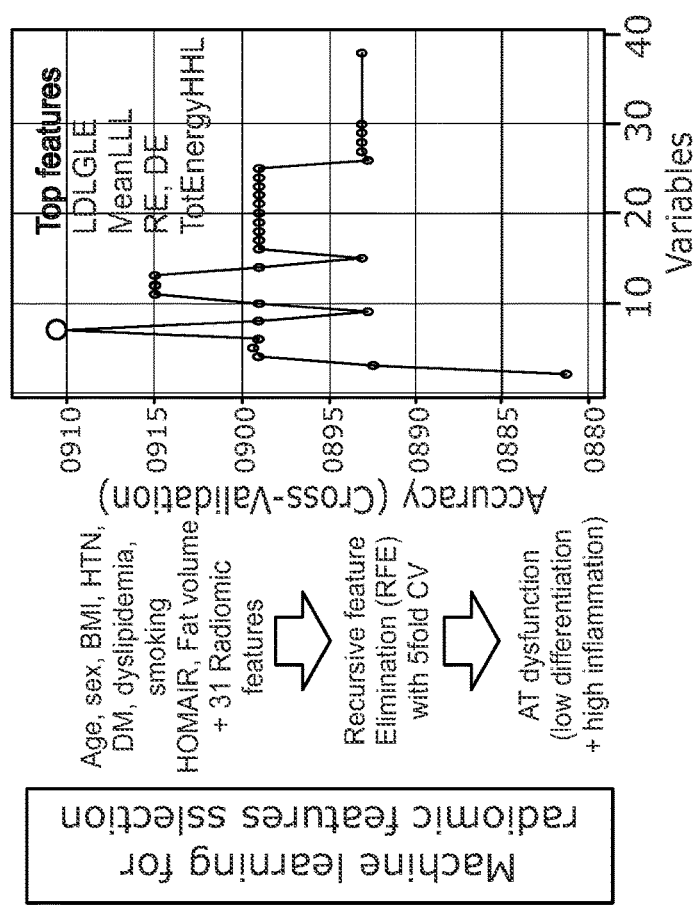

Internal Validation and Construction of a Radiotranscriptomic Score of Metabolic Risk The filtered radiomic features together with clinical profile characteristics (age, sex, diabetes mellitus, dyslipidemia, hypertension, HOMA-IR, body mass index and subcutaneous fat area) were then fed into a machine learning algorithm to identify the top radiomic features able to capture adipose tissue dysfunction (defined as high TNFA plus low FABP4 expression, based on their median values). A recursive feature elimination algorithm with five-fold cross-validation identified a set of 7 variables that maximized the accuracy of the model for adipose tissue dysfunction (FIG. 4(e)). These top predictors included age and body mass index plus a set of five radiomic features: Large Dependence Low Gray Level Emphsis (LDLGLE, a GLDM texture feature, which measures the joint distribution of large dependence with lower gray-level values), Mean LLL (the mean attenuation calculated on the LLL wavelet transformation), Run Entropy (RE, a GLRM feature and an index of heterogeneity in adipose tissue texture pattern), Dependence Entropy (DE, a GLDM feature quantifying gray level dependencies in an image), and Total Energy HHL (a first order feature in which lowest gray values contribute the least calculated on the HHL wavelet transformation). The combination of these five radiomic features (listed in Table 2) increased the c-statistic of the baseline clinical model for identification of dysfunctional adipose tissue ((Δ[AUC]=0.124, p=0.001, FIG. 4(f)). The exact form of the radiomic signature (FatHealth) was as follows:

Signature (FatHealth)=((((−1264629630*(LargeDependenceLowGrayLevelEmphasis)+
(259259.2593*Mean_$LLL$)+(101629629.6*DependenceEntropy)+(−
121148148.1*RunEntropy)+
(TotalEnergy_$HHL$)+37222222.22)/1000000)+
350)/10, where "*" represents multiplication (x).

These five radiomic features were then used to construct a radiotransriptomic signature of adipose tissue health i.e. FatHealth (FIG. 5(a)). FatHealth was independent of body mass index (r=0.068, p=0.307), and was positively associated with circulating levels of C-reactive protein (CRP, r=0.315, p=0.0006). In the derivation cohort—with available adipose tissue biopsies—FatHealth was significantly associated with the presence of risk factors (smoking, arterial hypertension and diabetes), reflecting their cumulative detrimental effect on adipose tissue biology (FIG. 5(c)). This association was significant also in the test cohort, demonstrating that FatHealth may be used as a non-invasive metric of adipose tissue health (FIG. 5(d)).

Validation of the Radiomic Score for Adipose Tissue Inflammation Against Positron Emission Tomography In an independent cohort of 40 patients undergoing PET/CT imaging, $^{18}$F-FDG uptake by subcutaneous adipose tissue was measured and associations with FatHealth calculated by the radiomic feature extraction of subcutaneous fat on CT scans were explored. FatHealth was strongly positively associated with adipose tissue FDG uptake as assessed by the target-to-background ratio (TBR, FIG. 5(e)) and had excellent diagnostic accuracy for high adipose tissue inflammation (i.e. TBR in the highest tertile, FIG. 5(f)). The validation of FatHealth against $^{18}$F-FDG PET/CT imaging, the gold-standard modality to assess tissue inflammation in-vivo, confirmed its value as a non-invasive biomarker of adipose tissue inflammation.

Validating Alternative Radiomic Signatures of the Invention

The discussion above demonstrates that the radiomic signature calculated on the basis of the five radiomic features listed in Table 2 (i.e. FatHealth) is an effective metric of adipose tissue dysfunction. To validate the performance of alternative radiomic signatures of the invention that include different selections of radiomic features, a series of several different radiomic signatures were tested for their ability to identify adipose tissue dysfunction (defined as previously as high inflammation and low differentiation status, i.e. high TNFA expression combined with low FABP4 expression). The results are shown in Tables 4 and 5 below, in which Nagelkerke's pseudo-$R^2$ provides a measure of the discrimination of the model for adipose tissue dysfunction.

In Tables 4 and 5, model performances for the Group A cohort are presented. In each of Examples 1-3, the current state of the art model (including age, sex, hypertension, dyslipidemia, smoking, diabetes mellitus, body mass index, HOMA-IR index, and subcutaneous fat volume) was progressively supplemented by radiomic signatures including progressively more radiomic features from the different groups of Table 3. Thus, each progressive row for each example corresponds to the inclusion of the indicated radiomic feature to the radiomic signature in addition to those listed in the previous rows. The models of Example 1 include only the "original" radiomic features listed in Table 2. In Example 2, each of the original radiomic features has been substituted by the radiomic feature that is most collinear with it, and in Example 3 each of the original radiomic features has been substituted by the radiomic feature that is least collinear with it (see Table 3). As can be seen from Table 4, substituting the original radiomic features for collinear equivalents still produces radiomic signatures that provide incremental value beyond the current state of the art in discriminating for adipose tissue dysfunction.

In Example 4, each of the "original" radiomic features of Table 2 has been replaced by an alternative radiomic feature from the same cluster, as identified using the hierarchical clustering algorithm (see Table 1). Again, Example 4 demonstrates that substituting each of the original radiomic features with an alternative radiomic feature from the same cluster still produces radiomic signatures that provide incremental value beyond the current state of the art in discriminating for adipose tissue dysfunction.

TABLE 4

Performance of alternative signatures constructed from collinear equivalents

| | | Nagelkerke's pseudo-$R^2$ (delta from previous step) |
|---|---|---|
| Current state-of-the-art | | 0.122 (—) |
| Example 1: Original radiomic features | | |
| +Group 1 | Large Dependence Low Gray Level Emphasis | 0.252 (+0.130) |
| +Group 2 | Dependence Entropy | 0.258 (+0.006) |
| +Group 3 | Run Entropy | 0.278 (+0.020) |
| +Group 4 | Mean LLL | 0.293 (+0.015) |
| +Group 5 | Total Energy HHL | 0.296 (+0.003) |
| Example 2: Most collinear alternative radiomic feature | | |
| +Group 1 | Sum Average | 0.198 (+0.076) |
| +Group 2 | Zone Entropy | 0.203 (+0.005) |
| +Group 3 | Run Entropy | 0.244 (+0.041) |
| +Group 4 | Median LLL | 0.253 (+0.009) |
| +Group 5 | Energy HHL | 0.254 (+0.001) |
| Example 3: Least collinear alternative radiomic feature | | |
| +Group 1 | High Gray Level Run Emphasis | 0.192 (+0.070) |
| +Group 2 | Run Entropy LHH | 0.204 (+0.012) |
| +Group 3 | Run Entropy | 0.256 (+0.052) |
| +Group 4 | Energy LLL | 0.289 (+0.033) |
| +Group 5 | Short Run Low Gray Level Emphasis | 0.297 (+0.008) |

TABLE 5

Performance of an alternative signature constructed from different features from the same clusters

| | | Nagelkerke's pseudo-$R^2$ (delta from previous step) |
|---|---|---|
| Current state-of-the-art | | 0.122 (—) |
| Example 4: Alternative features from clusters A-C | | |
| +Cluster A | Skewness | 0.132 (+0.010) |
| +Cluster A | Run Variance HLH | 0.141 (+0.009) |
| +Cluster A | Cluster Shade | 0.146 (+0.005) |
| +Cluster B | Coarseness HHH | 0.187 (+0.041) |
| +Cluster C | Energy LHL | 0.233 (+0.046) |

The data presented in Tables 4 and 5 thus demonstrate that regardless of which features are selected from each of the identified clusters or groups the radiomic signature of the invention provides improved discrimination for adipose tissue dysfunction over the current state of the art.

Radiomic signatures of the invention were also derived for other fat depots, in particular for thoracic and visceral adipose tissue, which are also useful targets for identifying adipose tissue dysfunction related to metabolic health. The optimised radiomic signature for thoracic and visceral adipose tissue is as follows:

Signature=(((−1264629630*LargeDependenceLowGrayLevelEmphasis)+(259259.2593*Mean_*LLL*)+(101629629.6*DependenceEntropy)+(−121148148.1*RunEntropy)+(TotalEnergy_*HHL*))/100000000)+50, where "*" represents multiplication (×). Thus, the radiomic signature of the invention is also applicable to other fat depots such as thoracic and visceral adipose tissue.

Summary of Findings

The radiomic signature of the invention is capable of non-invasively identifying adipose tissue dysfunction itself and characteristics of adipose tissue dysfunction, such as fibrosis and inflammation. The radiomic signature of the invention may therefore be used for predicting the risk of developing metabolic disorders, such as diabetes mellitus, which are associated with adipose tissue dysfunction.

Surprisingly, the radiomic signature need not be constructed from the radiomic features that are most strongly independently associated with adipose tissue dysfunction. Instead, it is actually advantageous to include a selection of radiomic features from different "clusters" of correlated or similar radiomic features instead of merely including those radiomic features that are individually most associated with AT dysfunction. Furthermore, the "original" radiomic features may be substituted with collinear equivalents while still providing an effective signature that is indicative of adipose tissue dysfunction.

A particularly attractive aspect of the invention is that it can be performed on historic medical imaging data that have been collected previously. The signature of the invention may be derived and calculated based on historic imaging data and the invention therefore provides a convenient tool for assessing a large number of patients without the need to perform further scans. The method of the invention need not therefore include the step of collecting the medical imaging data and can be performed based on a post-hoc analysis of existing medical imaging data.

The invention claimed is:

1. A method for characterising a region of interest comprising adipose tissue, the method comprising calculating the value of a radiomic signature of the region of interest using medical imaging data;
   wherein the radiomic signature is calculated on the basis of measured values of a plurality of radiomic features of the region of interest, the measured values of the radiomic features being calculated from the medical imaging data;
   wherein the medical imaging data are computed tomography data; and
   wherein the radiomic signature provides a measure of the texture of the adipose tissue of the region of interest.

2. The method of claim 1, wherein at least one of the radiomic features provides a measure of the texture of the region of interest.

3. The method of any preceding claim, wherein the radiomic signature is indicative of adipose tissue dysfunction.

4. The method of any preceding claim, wherein the radiomic signature is predictive of the likelihood of the subject developing a metabolic disorder.

5. The method of any preceding claim, wherein the plurality of radiomic features comprises at least two radiomic features selected from the radiomic features of groups 1 to 5, wherein the at least two radiomic features are each selected from different groups, and wherein:

group 1 consists of Large Dependence Low Gray Level Emphasis, Sum Average, Joint Average, High Gray Level Emphasis, Short Run High Gray Level Emphasis, Autocorrelation, and High Gray Level Run Emphasis;

group 2 consists of Total Energy HHL, Energy HHL, Size Zone Non Uniformity HHH, Size Zone Non Uniformity HLH, Size Zone Non Uniformity LHH, Gray Level Non Uniformity Normalized HHL (GLDM), Inverse Variance HHL, Gray Level Non Uniformity Normalized HHL (GLSZM), Size Zone Non Uniformity LHL, Run Length Non Uniformity HHH, Size Zone Non Uniformity HLL, Dependence Non Uniformity HHL, Gray Level Non Uniformity Normalized HHH (GLDM), Inverse Difference Moment HHH, Inverse Difference HHH, Uniformity HHH, Informational Measure of Correlation 2, Inverse Variance HHH, Total Energy LHL, Size Zone Non Uniformity, Sphericity, Size Zone Non Uniformity LLH, Run Length Non Uniformity Normalized HHL, Gray Level Non Uniformity Normalized HHH (GLSZM), Dependence Non Uniformity Normalized HHL, Zone Percentage HHL, Small Dependence Emphasis HHL, Size Zone Non Uniformity Normalized HHL, Small Area Emphasis HHL, Correlation, Dependence Non Uniformity LHH, Total Energy LHH, Short Run Emphasis HHH, Run Length Non Uniformity Normalized HHH, Dependence Non Uniformity LHL, Inverse Difference LHH, Inverse Difference Moment LHH, Small Dependence Emphasis HHH, Dependence Variance HLH, Run Percentage HHH, Zone Percentage HHH, Inverse Difference LHL, Dependence Non Uniformity HLH, Inverse Variance LHH, Large Dependence Emphasis HLH, Run Length Non Uniformity Normalized HLH, Short Run Emphasis HLH, Dependence Non Uniformity Normalized HLH, Difference Variance, Long Run Emphasis HLH, Energy LHL, Contrast (GLCM), Run Percentage HLH, Joint Entropy LHH, Difference Entropy, Small Dependence Emphasis HLH, Size Zone Non Uniformity Normalized HLH, Small Area Emphasis HLH, Difference Entropy LHH, Difference Average, Run Variance HLH, Inverse Difference Moment, Inverse Difference, Inverse Variance, Run Entropy LHH, Entropy LHH, Zone Percentage HLH, Sum Entropy LHH, Inverse Difference Moment Normalized, Inverse Difference Normalized, Small Dependence Low Gray Level Emphasis, Energy LHH, Joint Entropy LHL, Small Area Low Gray Level Emphasis, Strength, Dependence Non Uniformity LLH, Run Length Non Uniformity HHL, Gray Level Non Uniformity Normalized LHL (GLDM), Busyness, Dependence Non Uniformity Normalized LHH, Small Dependence Emphasis LHH, Coarseness, Zone Percentage LHH, Dependence Non Uniformity Normalized LHL, Run Length Non Uniformity HLH, Small Dependence Emphasis LHL, Joint Entropy, Small Area Emphasis LHL, Size Zone Non Uniformity Normalized LHL, Short Run Emphasis HLL, Run Length Non Uniformity LHH, Run Length Non Uniformity Normalized HLLL, Large Dependence Emphasis HLL, Long Run Emphasis HLL, Run Percentage HLL, Dependence Variance HLL, Dependence Non Uniformity HLL, Zone Percentage HLL, Dependence Non Uniformity, Dependence Non Uniformity HHH, Dependence Non Uniformity Normalized LLH, Low Gray Level Zone Emphasis, and Short Run Low Gray Level Emphasis;

group 3 consists of Dependence Entropy, Zone Entropy, Correlation, Informational Measure of Correlation 2, Zone Percentage HHH, Small Dependence Emphasis HHH, Run Percentage HHH, Dependence Non Uniformity Normalized LHL, Small Dependence Emphasis LHL, Zone Percentage HHL, Small Dependence High Gray Level Emphasis, Small Dependence Emphasis HHL, Dependence Non Uniformity Normalized HHL, Short Run Emphasis HHH, Run Length Non Uniformity Normalized HHH, Run Length Non Uniformity Normalized HHL, Size Zone Non Uniformity Normalized LHL, Small Area Emphasis LHL, Size Zone Non Uniformity Normalized HHL, Small Area Emphasis HHL, Zone Percentage HLH, Run Variance HLH, Small Dependence Emphasis HLH, Long Run Emphasis HLH, Size Zone Non Uniformity Normalized LLH, Small Area Emphasis LLH, Size Zone Non Uniformity Normalized HLH, Small Area Emphasis HLH, Run Percentage HLH, Run Length Non Uniformity Normalized HLH, Short Run Emphasis HLH, Large Dependence Emphasis HLH, Zone Percentage LHH, Small Dependence Emphasis LLH, Small Dependence Emphasis LHH, Dependence Non Uniformity Normalized HLH, Zone Percentage LLH, Dependence Variance HLH, Dependence Non Uniformity Normalized LLH, Dependence Non Uniformity Normalized LHH, Inverse Difference LHL, Inverse Difference Moment HHH, Inverse Difference HHH, Uniformity HHH, Gray Level Non Uniformity Normalized LHL (GLSZM), Gray Level Non Uniformity Normalized HHH (GLDM), Gray Level Non Uniformity Normalized HHL (GLDM), Joint Entropy LHL, Inverse Difference Normalized, Inverse Difference Moment Normalized, Long Run Emphasis HLL, Zone Percentage HLL, Inverse Difference, Inverse Difference Moment, Difference Average, Run Percentage HLL, Large Dependence Emphasis HLL, Contrast (GLCM), Short Run Emphasis HLL, Run Length Non Uniformity Normalized HLL, Inverse Variance, Inverse Variance HHL, Difference Entropy, Dependence Variance HLL, Inverse Difference Moment LHH, Difference Variance, Entropy LHH, Inverse Variance LHH, Inverse Difference LHH, Inverse Variance HHH, Sum Entropy LHH, Joint Entropy LHH, Gray Level Non Uniformity Normalized HHH (GLSZM), Gray Level Non Uniformity Normalized HHL (GLSZM), Difference Entropy LHH, and Run Entropy LHH;

group 4 consists of Mean LLL, Median LLL, and Energy LLL; and group 5 consists of Run Entropy.

6. The method of claim 5, wherein the at least two radiomic features comprise at least two of Large Dependence Low Gray Level Emphasis, Total Energy HHL, Dependence Entropy, Mean LLL, and Run Entropy, optionally wherein the at least two radiomic features consists of Large Dependence Low Gray Level Emphasis, Total Energy HHL, Dependence Entropy, Mean LLL, and Run Entropy.

7. The method of claim 5, wherein the at least two radiomic features are selected from the radiomic features of clusters A to C, wherein the at least two radiomic features are each selected from different clusters, and wherein:
cluster A consists of the radiomic features of groups 1 to 3;
cluster B consists of the radiomic features of group 4; and
cluster C consists of the radiomic features of group 5.

8. The method of any one of claims 1 to 4, wherein the plurality of radiomic features comprises at least two radiomic features selected from the radiomic features of clusters A to C, wherein the at least two radiomic features are each selected from different clusters, and wherein:
cluster A consists of Large Dependence Low Gray Level Emphasis, Run Entropy, Dependence Entropy, Cluster Shade, Skewness, Run Variance HLH, Voxel Number, and Gray Level Non Uniformity;
cluster B consists of Mean LLL, Median LLL, Joint Average, Median, Complexity, Long Run High Gray Level Emphasis, Sphericity, Kurtosis, and Coarseness HHH; and
cluster C consists of Major Axis, Small Dependence High Gray Level Emphasis, Minor Axis, Energy LLL, Maximum 2D Diameter Row, Long Run Low Gray Level Emphasis, Total Energy HHL, Dependence Non Uniformity Normalized HHH, Contrast (GLCM), Surface Volume Ratio, Sum Entropy, Size Zone Non Uniformity Normalized HHH, Cluster Prominence LHH, Contrast LLH (GLCM), and Energy LHL.

9. The method of any one of claims 1 to 6, wherein the at least two radiomic features comprises at least five radiomic features.

10. The method of any preceding claim, further comprising predicting the risk of the subject developing a metabolic disorder based at least on at least the calculated value of the radiomic signature, optionally wherein the metabolic disorder is diabetes or insulin resistance.

11. The method of any preceding, further comprising determining whether the subject has adipose tissue dysfunction based on at least the calculated value of the radiomic signature.

12. A method for deriving a radiomic signature indicative of adipose tissue dysfunction, the method comprising using a radiomic dataset to construct a radiomic signature indicative of adipose tissue dysfunction, the radiomic signature being calculated on the basis of a second plurality of radiomic features;
wherein the dataset comprises the values of a first plurality of radiomic features obtained from medical imaging data of a region of interest comprising adipose tissue for each of a plurality of individuals, the plurality of individuals comprising a first group of individuals identified as having adipose tissue dysfunction and a second group of individuals identified as not having adipose tissue dysfunction;
wherein the medical imaging data are computed tomography data;
wherein the second plurality of radiomic features is selected from amongst the first plurality of radiomic features; and
wherein the radiomic signature is constructed to provide a measure of the texture of the adipose tissue of the region of interest.

13. The method according to claim 12, wherein each of the individuals is identified as having or not having adipose tissue dysfunction based at least in part on a marker of adipose tissue dysfunction, optionally wherein the radiomic dataset further comprises the marker of adipose tissue dysfunction.

14. The method of claim 13, wherein the marker comprises the presence or absence of a metabolic disorder, or wherein the marker comprises a phenotypic characteristic of adipose tissue associated with adipose tissue dysfunction, or wherein the marker comprises a surrogate marker of a phenotypic characteristic of adipose tissue associated with adipose tissue dysfunction.

15. The method of any one of claims 12 to 14, further comprising identifying a first subset of the first plurality of radiomic features that are not collinear with each other, the second plurality of radiomic features comprising at least two radiomic features that are each selected to be, or to be collinear with, different radiomic features belonging to the first subset.

16. The method of claim 15, further comprising using a feature selection algorithm to identify a second subset of radiomic features from amongst the first subset, wherein the at least two radiomic features are selected to be, or to be collinear with, different radiomic features belonging to the second subset.

17. The method of any one of claim 15 or 16, wherein each of the at least two radiomic features is selected to be stable, optionally wherein all unstable radiomic features are removed from the first plurality of radiomic features prior to selecting the second plurality of radiomic features.

18. The method of any one of claims 12 to 17, wherein the radiomic signature is constructed to be associated with adipose tissue dysfunction.

19. The method of any one of claims 12 to 18, wherein the step of constructing the radiomic signature is performed using a machine learning algorithm.

20. The method of any one of claims 12 to 19, wherein at least one of the second plurality of radiomic features provides a measure of the texture of the region of interest.

21. The method of any one of claims to 12 to 20, further comprising configuring a system for calculating the value of the radiomic signature for a patient.

22. The method of any one of claims 12 to 21, further comprising characterising a region of interest of a patient by calculating the value of the radiomic signature for the region of interest of the patient, wherein the region of interest of the patient comprises adipose tissue.

23. The method of any preceding claim, wherein the adipose tissue is subcutaneous adipose tissue, visceral adipose tissue, or thoracic adipose tissue.

24. The method of any preceding claim, wherein the adipose tissue comprises non-cardiovascular adipose tissue.

25. A system configured to perform the method of any one of claims 1 to 24.

* * * * *